(12) United States Patent
Bosse et al.

(10) Patent No.: US 10,772,840 B2
(45) Date of Patent: *Sep. 15, 2020

(54) SUMATRIPTAN PROMETHAZINE PHARMACEUTICAL COMPOSITIONS

(71) Applicant: Charleston Laboratories, Inc., Jupiter, FL (US)

(72) Inventors: Paul Bosse, Jupiter, FL (US); John Ameling, Jupiter, FL (US); William Kozarek, Jensen Beach, FL (US); Bernard Schachtel, Jupiter, FL (US); John Higgins, Independence, MO (US)

(73) Assignee: CHARLESTON LABORATORIES, INC., Jupiter, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 16/149,619

(22) Filed: Oct. 2, 2018

(65) Prior Publication Data

US 2019/0029964 A1 Jan. 31, 2019

Related U.S. Application Data

(63) Continuation of application No. 15/449,798, filed on Mar. 3, 2017, now Pat. No. 10,179,109.

(Continued)

(51) Int. Cl.
*A61K 9/48* (2006.01)
*A01N 43/42* (2006.01)
(Continued)

(52) U.S. Cl.
CPC .......... *A61K 9/4808* (2013.01); *A01N 43/42* (2013.01); *A61K 9/1611* (2013.01);
(Continued)

(58) Field of Classification Search
CPC ...... A01N 43/42; A61K 31/44; A61K 9/4808; A61K 9/5078; A61K 9/1676;
(Continued)

(56) References Cited

U.S. PATENT DOCUMENTS

| 3,048,526 A | 8/1962 | Boswell |
| 3,108,046 A | 10/1963 | Harbit |

(Continued)

FOREIGN PATENT DOCUMENTS

| CA | 2262267 A1 | 8/1999 |
| CN | 1291092 A | 4/2001 |

(Continued)

OTHER PUBLICATIONS

[Yakkyoku] Yamashita, R. et al. Mechanism of action of preventive drugs for headache acute treatment. The Journal of Practical Pharmacy, 2007, vol. 58, No. 7, pp. 20-26.

(Continued)

*Primary Examiner* — Carlos A Azpuru
(74) *Attorney, Agent, or Firm* — Wilson Sonsini Goodrich & Rosati, P.C.

(57) ABSTRACT

Pharmaceutical compositions and methods are provided to treat headache, headache-associated symptoms, photophobia, or adverse effects associated with the headache. Also provided herein are small smooth particulates comprising a $5HT_{1B/1D}$ receptor agonist. Compositions for oral administration are described herein wherein the compositions comprise a combination of active agents, such as a $5HT_{1B/1D}$ receptor agonist and one or more antiemetics.

4 Claims, 3 Drawing Sheets

Related U.S. Application Data

(60) Provisional application No. 62/304,074, filed on Mar. 4, 2016, provisional application No. 62/415,991, filed on Nov. 1, 2016.

(51) Int. Cl.
  *A61K 31/44* (2006.01)
  *A61K 9/50* (2006.01)
  *A61K 9/16* (2006.01)
  *A61K 31/4045* (2006.01)
  *A61K 31/5415* (2006.01)

(52) U.S. Cl.
  CPC .......... *A61K 9/1623* (2013.01); *A61K 9/1652* (2013.01); *A61K 9/1676* (2013.01); *A61K 9/5078* (2013.01); *A61K 9/5084* (2013.01); *A61K 31/4045* (2013.01); *A61K 31/44* (2013.01); *A61K 31/5415* (2013.01)

(58) Field of Classification Search
  CPC .. A61K 9/5084; A61K 9/1652; A61K 9/1623; A61K 9/1611; A61P 43/00; A61P 25/06; A61P 25/04; A61P 25/00
  See application file for complete search history.

(56) References Cited

U.S. PATENT DOCUMENTS

| | | |
|---|---|---|
| 3,536,809 A | 10/1970 | Norman |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,113,866 A | 9/1978 | Lednicer |
| 4,265,875 A | 5/1981 | Byrne et al. |
| 4,478,822 A | 10/1984 | Haslam et al. |
| 4,532,126 A | 7/1985 | Ebert et al. |
| 4,588,580 A | 5/1986 | Gale et al. |
| 4,624,665 A | 11/1986 | Nuwayser |
| 4,625,494 A | 12/1986 | Iwatschenko et al. |
| 4,626,539 A | 12/1986 | Aungst et al. |
| 4,671,953 A | 6/1987 | Stanley et al. |
| 4,685,911 A | 8/1987 | Konno et al. |
| 4,786,505 A | 11/1988 | Lovgren et al. |
| 4,800,083 A | 1/1989 | Hom et al. |
| 4,820,522 A | 4/1989 | Radebaugh et al. |
| 4,834,978 A | 5/1989 | Nuwayser |
| 4,853,211 A | 8/1989 | Kurobe et al. |
| 4,871,353 A | 10/1989 | Thomsen |
| 4,904,479 A | 2/1990 | Illum |
| 4,906,463 A | 3/1990 | Cleary et al. |
| 4,919,939 A | 4/1990 | Baker |
| 4,925,444 A | 5/1990 | Orkin et al. |
| 4,935,243 A | 6/1990 | Borkan et al. |
| 4,950,484 A | 8/1990 | Olthoff et al. |
| 5,013,726 A | 5/1991 | Ivy et al. |
| 5,055,461 A | 10/1991 | Kelleher et al. |
| 5,059,595 A | 10/1991 | Le Grazie |
| 5,073,543 A | 12/1991 | Marshall et al. |
| 5,120,548 A | 6/1992 | McClelland et al. |
| 5,266,331 A | 11/1993 | Oshlack et al. |
| 5,298,520 A | 3/1994 | Baker et al. |
| 5,354,556 A | 10/1994 | Sparks et al. |
| 5,373,022 A | 12/1994 | Fawzi et al. |
| 5,376,672 A | 12/1994 | Pilgrim |
| 5,393,773 A | 2/1995 | Craig et al. |
| 5,425,950 A | 6/1995 | Dandiker et al. |
| 5,445,529 A | 8/1995 | Yamamoto |
| 5,445,829 A | 8/1995 | Paradissis et al. |
| 5,464,864 A | 11/1995 | King et al. |
| 5,468,504 A | 11/1995 | Schaeffer |
| 5,478,577 A | 12/1995 | Sackler et al. |
| 5,484,406 A | 1/1996 | Wong et al. |
| 5,508,042 A | 4/1996 | Oshlack et al. |
| 5,536,249 A | 7/1996 | Castellano et al. |
| 5,549,912 A | 8/1996 | Oshlack et al. |
| 5,554,639 A | 9/1996 | Craig et al. |
| 5,591,767 A | 1/1997 | Mohr et al. |
| 5,602,162 A | 2/1997 | Baker et al. |
| 5,610,184 A | 3/1997 | Shahinian, Jr. |
| 5,629,333 A | 5/1997 | Young |
| 5,635,204 A | 6/1997 | Gevirtz et al. |
| 5,637,611 A | 6/1997 | King et al. |
| 5,639,476 A | 6/1997 | Oshlack et al. |
| 5,656,295 A | 8/1997 | Oshlack et al. |
| 5,674,533 A | 10/1997 | Santus et al. |
| 5,705,506 A | 1/1998 | Merlet et al. |
| 5,705,520 A | 1/1998 | Craig et al. |
| 5,712,302 A | 1/1998 | Young |
| 5,733,556 A | 3/1998 | Schrier et al. |
| 5,738,874 A | 4/1998 | Conte et al. |
| 5,741,510 A | 4/1998 | Rolf et al. |
| 5,827,852 A | 10/1998 | Russell et al. |
| 5,827,871 A | 10/1998 | King et al. |
| 5,837,284 A | 11/1998 | Mehta et al. |
| 5,840,731 A | 11/1998 | Mayer et al. |
| 5,854,270 A | 12/1998 | Gambhir |
| 5,863,559 A | 1/1999 | Phillips et al. |
| 5,863,922 A | 1/1999 | Mayer et al. |
| 5,866,161 A | 2/1999 | Childers et al. |
| 5,871,776 A | 2/1999 | Mehta |
| 5,891,885 A | 4/1999 | Caruso |
| 5,902,632 A | 5/1999 | Mehta |
| 5,919,479 A | 7/1999 | Zhang et al. |
| 5,929,059 A | 7/1999 | Sanger et al. |
| 5,954,700 A | 9/1999 | Kovelman |
| 5,962,494 A | 10/1999 | Young |
| 5,968,551 A | 10/1999 | Oshlack et al. |
| 6,020,001 A | 2/2000 | Phillips et al. |
| 6,063,802 A | 5/2000 | Winterborn |
| 6,077,539 A | 6/2000 | Plachetka et al. |
| 6,146,361 A | 11/2000 | Dibiasi et al. |
| 6,160,020 A | 12/2000 | Ohannesian et al. |
| 6,228,863 B1 | 5/2001 | Palermo et al. |
| 6,255,502 B1 | 7/2001 | Penkler et al. |
| 6,258,380 B1 | 7/2001 | Overholt |
| 6,261,595 B1 | 7/2001 | Stanley et al. |
| 6,287,600 B1 | 9/2001 | Ouali et al. |
| 6,303,142 B1 | 10/2001 | Zhang et al. |
| 6,335,033 B2 | 1/2002 | Oshlack et al. |
| 6,341,387 B1 | 1/2002 | Zars |
| 6,368,627 B1 | 4/2002 | Phillips et al. |
| 6,372,254 B1 | 4/2002 | Ting et al. |
| 6,376,550 B1 | 4/2002 | Raber et al. |
| 6,465,006 B1 | 10/2002 | Zhang et al. |
| 6,469,227 B1 | 10/2002 | Cooke et al. |
| 6,475,494 B2 | 11/2002 | Kaiko et al. |
| 6,482,435 B1 | 11/2002 | Stratton et al. |
| 6,491,945 B1 | 12/2002 | Childers et al. |
| 6,572,871 B1 | 6/2003 | Church et al. |
| 6,572,885 B2 | 6/2003 | Oshlack et al. |
| 6,613,350 B1 | 9/2003 | Zhang et al. |
| 6,649,183 B2 | 11/2003 | Rubin et al. |
| 6,699,502 B1 | 3/2004 | Fanara et al. |
| 6,733,783 B2 | 5/2004 | Oshlack et al. |
| 6,756,053 B2 | 6/2004 | Zhang et al. |
| 6,773,783 B2 | 8/2004 | Saito et al. |
| 6,780,426 B2 | 8/2004 | Zhang et al. |
| 6,855,332 B2 | 2/2005 | Gizurarson et al. |
| 6,913,768 B2 | 7/2005 | Couch et al. |
| 7,029,698 B2 | 4/2006 | Waranis et al. |
| RE39,221 E | 8/2006 | Raffa et al. |
| 7,094,228 B2 | 8/2006 | Zhang et al. |
| 7,157,103 B2 | 1/2007 | Sackler |
| 7,172,767 B2 | 2/2007 | Kaiko et al. |
| 7,201,920 B2 | 4/2007 | Kumar et al. |
| 7,214,385 B2 | 5/2007 | Gruber |
| 7,214,711 B2 | 5/2007 | Hochman |
| 7,332,183 B2 | 2/2008 | Plachetka et al. |
| 7,342,028 B2 | 3/2008 | Hagan et al. |
| 7,585,493 B2 | 9/2009 | Hale et al. |
| 7,666,337 B2 | 2/2010 | Yang et al. |
| 7,744,916 B2 | 6/2010 | Pauletti et al. |

(56) References Cited

U.S. PATENT DOCUMENTS

| | | |
|---|---|---|
| 7,863,296 B2 | 1/2011 | Weiner et al. |
| 8,022,095 B2 | 9/2011 | Plachetka |
| 8,124,126 B2 | 2/2012 | Bosse et al. |
| 8,268,791 B2 | 9/2012 | Maggio |
| 8,653,066 B2 | 2/2014 | Bosse |
| 8,654,066 B2 | 2/2014 | Jung et al. |
| 8,728,522 B2 | 5/2014 | Bosse et al. |
| 9,198,867 B2 | 12/2015 | Bosse et al. |
| 9,226,901 B2 | 1/2016 | Bosse et al. |
| 9,415,362 B2 | 8/2016 | Stoyanov et al. |
| 9,433,625 B2 | 9/2016 | Bosse et al. |
| 9,622,980 B2 | 4/2017 | Grenier et al. |
| 9,629,805 B2 | 4/2017 | Karakatsani et al. |
| 9,775,837 B2 | 10/2017 | Bosse et al. |
| 9,855,264 B2 | 1/2018 | Bosse |
| 10,016,368 B2 | 7/2018 | Bosse |
| 10,179,109 B2 * | 1/2019 | Bosse .................. A61K 9/1623 |
| 2003/0008892 A1 | 1/2003 | Coe et al. |
| 2003/0044458 A1 | 3/2003 | Wright et al. |
| 2003/0124185 A1 | 7/2003 | Oshlack et al. |
| 2003/0133982 A1 | 7/2003 | Heimlich et al. |
| 2003/0181462 A1 | 9/2003 | Doods et al. |
| 2003/0225002 A1 | 12/2003 | Livingstone |
| 2004/0019080 A1 | 1/2004 | Sheftell et al. |
| 2004/0043071 A1 | 3/2004 | Pauletti et al. |
| 2004/0047907 A1 | 3/2004 | Oshlack et al. |
| 2004/0136913 A1 | 7/2004 | Dugger et al. |
| 2004/0136914 A1 | 7/2004 | Dugger et al. |
| 2004/0152713 A1 | 8/2004 | Petrie |
| 2004/0156859 A1 | 8/2004 | Ezrin et al. |
| 2004/0156903 A1 | 8/2004 | Abrams et al. |
| 2004/0167200 A1 | 8/2004 | Coe et al. |
| 2004/0170680 A1 | 9/2004 | Oshlack et al. |
| 2004/0185096 A1 | 9/2004 | Oshlack et al. |
| 2004/0195413 A1 | 10/2004 | Reed et al. |
| 2004/0213828 A1 | 10/2004 | Smith |
| 2004/0241159 A1 | 12/2004 | De Cellery D'allens |
| 2004/0248956 A1 | 12/2004 | Hagmann et al. |
| 2004/0266807 A1 | 12/2004 | Oshlack et al. |
| 2005/0074493 A1 | 4/2005 | Mehta et al. |
| 2005/0080012 A1 | 4/2005 | Mickle et al. |
| 2005/0084530 A1 | 4/2005 | Rao et al. |
| 2005/0106249 A1 | 5/2005 | Hwang et al. |
| 2005/0147710 A1 | 7/2005 | Teckoe et al. |
| 2005/0158382 A1 | 7/2005 | Cruz et al. |
| 2005/0163856 A1 | 7/2005 | Maloney et al. |
| 2005/0232986 A1 | 10/2005 | Brown et al. |
| 2005/0232987 A1 | 10/2005 | Srinivasan et al. |
| 2005/0232993 A1 | 10/2005 | Brown et al. |
| 2005/0266032 A1 | 12/2005 | Srinivasan et al. |
| 2005/0266072 A1 | 12/2005 | Oshlack et al. |
| 2005/0272810 A1 | 12/2005 | Davis et al. |
| 2005/0281875 A1 | 12/2005 | Srinivasan et al. |
| 2005/0282879 A1 | 12/2005 | Salehani |
| 2006/0009512 A1 | 1/2006 | Curwen et al. |
| 2006/0029664 A1 | 2/2006 | Srinivasan et al. |
| 2006/0057205 A1 | 3/2006 | Srinivasan et al. |
| 2006/0073189 A1 | 4/2006 | Pinney et al. |
| 2006/0110327 A1 | 5/2006 | Emigh et al. |
| 2006/0127479 A1 | 6/2006 | Kumaraperumal et al. |
| 2006/0134207 A1 | 6/2006 | Srinivasan et al. |
| 2006/0142273 A1 | 6/2006 | Rudolf et al. |
| 2006/0165604 A1 | 7/2006 | Dugger, III |
| 2006/0177380 A1 | 8/2006 | Emigh et al. |
| 2006/0183693 A1 | 8/2006 | Doods et al. |
| 2006/0198790 A1 | 9/2006 | Dugger, III |
| 2006/0204578 A1 | 9/2006 | Vergez et al. |
| 2006/0240105 A1 | 10/2006 | Devane et al. |
| 2007/0003622 A1 | 1/2007 | Srinivasan et al. |
| 2007/0025040 A1 | 2/2007 | Tsai et al. |
| 2007/0059254 A1 | 3/2007 | Singh |
| 2007/0099849 A1 | 5/2007 | Livingstone |
| 2007/0148097 A1 | 6/2007 | Finn et al. |
| 2007/0166336 A1 | 7/2007 | Delmarre et al. |
| 2007/0191462 A1 | 8/2007 | Hettiarachchi et al. |
| 2007/0231268 A1 | 10/2007 | Emigh et al. |
| 2007/0259040 A1 | 11/2007 | Cherukuri |
| 2008/0044482 A1 | 2/2008 | Oshlack et al. |
| 2008/0074208 A1 | 3/2008 | Lee |
| 2008/0075781 A1 | 3/2008 | Oshlack et al. |
| 2008/0103134 A1 | 5/2008 | Rudolf et al. |
| 2008/0131517 A1 | 6/2008 | Fawzy et al. |
| 2008/0181941 A1 | 7/2008 | Oshlack et al. |
| 2008/0213343 A1 | 9/2008 | Obermeier et al. |
| 2008/0292699 A1 | 11/2008 | Brown et al. |
| 2009/0004281 A1 | 1/2009 | Nghiem et al. |
| 2009/0068269 A1 | 3/2009 | Oshlack et al. |
| 2009/0118170 A1 | 5/2009 | Dugger, III |
| 2009/0124554 A1 | 5/2009 | Dugger, III |
| 2009/0156581 A1 | 6/2009 | Dillon et al. |
| 2009/0162297 A1 | 6/2009 | Dugger, III et al. |
| 2009/0162298 A1 | 6/2009 | Dugger, III et al. |
| 2009/0163451 A1 | 6/2009 | Porreca et al. |
| 2009/0175939 A1 | 7/2009 | Bosse et al. |
| 2009/0232898 A1 | 9/2009 | Pettersson et al. |
| 2009/0311335 A1 | 12/2009 | Jenkins et al. |
| 2010/0008995 A1 | 1/2010 | Duncalf et al. |
| 2010/0047343 A1 | 2/2010 | Haslam et al. |
| 2010/0112050 A1 | 5/2010 | Ryoo et al. |
| 2010/0143469 A1 | 6/2010 | Bosse |
| 2010/0159007 A1 | 6/2010 | Staniforth |
| 2010/0160378 A1 | 6/2010 | Maggio |
| 2010/0196471 A1 | 8/2010 | Jain et al. |
| 2010/0227879 A1 | 9/2010 | Mudumba et al. |
| 2010/0291201 A1 | 11/2010 | Shah et al. |
| 2011/0066100 A1 | 3/2011 | Sebree et al. |
| 2011/0077272 A1 | 3/2011 | Main |
| 2011/0118189 A1 | 5/2011 | Farr et al. |
| 2011/0262539 A1 | 10/2011 | Bosse et al. |
| 2012/0202866 A1 | 8/2012 | Dugger, III et al. |
| 2014/0073678 A1 | 3/2014 | Dadey et al. |
| 2014/0134248 A1 | 5/2014 | Bosse |
| 2014/0308349 A1 | 10/2014 | Bosse et al. |
| 2015/0290211 A1 | 10/2015 | Bosse et al. |
| 2016/0303102 A1 | 10/2016 | Albayrak |
| 2016/0310428 A1 | 10/2016 | Wening et al. |
| 2016/0310437 A1 | 10/2016 | Wening et al. |
| 2016/0317447 A1 | 11/2016 | Bosse |
| 2016/0375013 A1 | 12/2016 | Bosse |
| 2016/0375014 A1 | 12/2016 | Bosse |
| 2017/0000783 A1 | 1/2017 | Devane et al. |
| 2017/0173037 A1 | 6/2017 | Bosse |
| 2017/0202801 A1 | 7/2017 | Karakatsani et al. |
| 2017/0354603 A1 | 12/2017 | Bosse |
| 2018/0228797 A1 | 8/2018 | Bosse |
| 2018/0325892 A1 | 11/2018 | Bosse et al. |
| 2018/0333360 A1 | 11/2018 | Bosse |

FOREIGN PATENT DOCUMENTS

| | | |
|---|---|---|
| DE | 102005013726 A1 | 9/2006 |
| EP | 2124556 A2 | 12/2009 |
| EP | 2240022 A2 | 10/2010 |
| EP | 3090743 A1 | 11/2016 |
| FR | 2787713 A1 | 6/2000 |
| GB | 2325161 A | 11/1998 |
| JP | 2000507614 A | 6/2000 |
| JP | 2008525509 A | 7/2008 |
| JP | 2008534562 A | 8/2008 |
| JP | 2013237727 A | 11/2013 |
| JP | 2015121474 A | 7/2015 |
| WO | WO-9718801 A1 | 5/1997 |
| WO | WO-9942095 A1 | 8/1999 |
| WO | WO-02067987 A2 | 9/2002 |
| WO | WO-02080953 A3 | 12/2002 |
| WO | WO-03024456 A1 | 3/2003 |
| WO | WO-2005007135 A1 | 1/2005 |
| WO | WO-2006072413 A1 | 7/2006 |
| WO | WO-2006103407 A2 | 10/2006 |
| WO | WO-2006103418 A1 | 10/2006 |
| WO | WO-2006022996 A3 | 12/2006 |
| WO | WO-2007035573 A3 | 6/2007 |
| WO | WO-2007070504 A2 | 6/2007 |
| WO | WO-2007130507 A2 | 11/2007 |

(56) References Cited

FOREIGN PATENT DOCUMENTS

| WO | WO-2008027350 A3 | 5/2008 |
|---|---|---|
| WO | WO-2008074419 A1 | 6/2008 |
| WO | WO-2008124081 A2 | 10/2008 |
| WO | WO-2008070268 A3 | 11/2008 |
| WO | WO-2009089494 A3 | 1/2010 |
| WO | WO-2011006012 A1 | 1/2011 |
| WO | WO-2010062688 A3 | 5/2012 |
| WO | WO-2014043346 A2 | 3/2014 |
| WO | WO-2015157738 A1 | 10/2015 |
| WO | WO-2017152130 A8 | 10/2017 |

OTHER PUBLICATIONS

Apr. 16, 2019 Non-Final Office Action for U.S. Appl. No. 15/683,646.
Alexander, et al. Comparison of ondansetron and droperidol in reducing postoperative nausea and vomiting associated with patient-controlled analgesia. Anaesthesia. Dec. 1995;50(12):1086-8.
Anonymous: Strong Efficacy Data Promp Charleston Laboratories to Halt Phase 3 Study of CL-108 in Patients with Moderate to Severe Acute Pain, Oct. 29, 2013. {Retrieved from the internet: URL:http://Charlestonlabs.com/wp-content/uploads/CL-108-Ph3-Top-Line-Al.pdf [Retrieved on Oct. 23, 2017, pp. 1-2].
Apfel, et al. A factorial trial of six interventions for the prevention of postoperative nausea and vomiting. N. Engl J Med. Jun. 10, 2004;350(24):2441-51.
Asadollahi, et al. Promethazine plus sumatriptan in the treatment of migraine: a randomized clinical trial. Headache. Jan. 2014;54(1):94-108. Epub Nov. 1, 2013.
Braude, et al. Ondansetron versus promethazine to treat acute undifferentiated nausea in the emergency department: a randomized, double-blind, noninferiority trial. Acad Emerg Med. Mar. 2008;15(3):209-15.
Charleston Laboratories' Investigational New Drug Application, pp. 93-94, filed with the U.S. Food and Drug Administration on Sep. 5, 2008. Charleston Laboratories is the assignee of the present application.
Chia, et al. (Abstract of Acta Anaesthesiol Scand. 2004:48(5):625-630) 2 pages (year: 2004).
Chia, et al. The effect of promethazine on postoperative pain: a comparison of preoperative, postoperative, and placebo administration in patients following total abdominal hysterectomy. Acta Anaesthesiol Scand. May 2004;48(5):625-30.
Chinese Application No. 2015206947715 Office Action dated Jun. 3, 2016.
Codapane Forte Paracetamol and codeine phosphate Product Information pp. 1-10 Jul. 6, 2016.
Dissolution Testing, Wikipedia, May 27, 2014 [retrieved from internet on Jul. 19, 2017]< URL: https://en.wikipedia.org/w/index.php?title=Dissolution_testing&oldid=610334789>.
Eletriptan Hydrobromide. Orange book: approved drug products with therapeutic equivalence evaluations. FDA. www.accessdata.fda.gov. Updated Aug. 21, 2014.
European search report dated Nov. 19, 2014 for EP Application No. 14177981.9.
Farshchi, Amir, et al., Antinociceptive Effect Promethazine in Mice Introduction, Iranian Journal of Basic Medical Sciences, vol. 12, No. 3-4, Jan. 1, 2009, pp. 140-145.
Final Rejection dated Apr. 17, 2019 for U.S. Appl. No. 15/452,628.
Fishman, et al. Bonica's Management of Pain, 4th Edition, Chapter 43: Cancer Pain: Principles of Management and Pharmacotherapy, pp. 582 & 588 (2010).
Flovatriptan Succinate. Orange book: approved drug products with therapeutic equivalence evaluations. FDA. www.accessdata.fda.gov. Updated Aug. 21, 2014.
Foster, et al. Complicated pain management in a CYP450 2D6 poor metabolizer. Pain Pract. Dec. 2007;7(4):352-6.
Great Britain Application No. 1515866.0 Search and Examination Report dated Jun. 13, 2016.
Headache Disorders: A Management Guide for Practitioners, by A. Rapoport and F. Sheftell (W. B. Saunders, Philadelphia, 1996), the International Headache Society (IHS), which were published as a supplement to the journal Cephalalgia (Cephalalgia. 2004;24 Suppl 1:9-160).
Headache in Clinical Practice (edited by S. Silberstein et al., Oxford Univ. Press, 1998); The Headaches, by J. Olesen.
Hong Kong Application No. 10105451.9 (see WO 08/070268 A2).
Imitrex prescribing information. Dec. 2004. http://www.fda.gov/ohrms/dockets/ac/05/briefing/2005-4180b_09_05_imitrex%20label%20tablet%2012-04%20sponsor.pdf.
International Application No. PCT/US2015/025481 International Preliminary Report on Patentability dated Oct. 12, 2016.
International Application No. PCT/US2015/048999 International Preliminary Report on Patentability dated Mar. 14, 2017.
International Application No. PCT/US2016/056910 International Search Report and Written Opinion dated Dec. 22, 2016.
International Application No. PCT/US2016/056910, International Preliminary Report on Patentability dated Apr. 17, 2018.
International Application No. PCT/US2017/020797 International Preliminary Report on Patentability dated Sep. 13, 2018.
International Application No. PCT/US2017/036801 International Search Report and Written Opinion dated Aug. 16, 2017.
International preliminary report on patentability dated Jul. 22, 2010 for PCT Application No. PCT/US09/30662.
International search report dated May 22, 2009 for Application No. US2009/30662.
International search report dated Sep. 1, 2010 for PCT Application No. PCT/US2010/41433.
International search report dated Sep. 23, 2008 for Application No. PCT/US2007/80831.
Japanese Application No. 2009-531645 (see WO 08/070268 A2).
Japanese Application No. 2010-542386 (see WO 09/089494 A2).
Kamerman, Peter R., et al., Interactions between Metoclopramide and Morphine Enhanced Anticiception and Motor Dysfunction in Rats, Clinical and Experimental Pharmacology and Physiology, vol. 34, No. 1-2, Jan. 2007 (Jan. 1, 2007), pp. 106-112, XP055572892, AU ISSN: 0305-1870, DOI: 10.1111/j. 1440-1681.2007.04533.
Kawahara, Y. et al. Headache medication / Dizziness treatment. The Journal of Practical Pharmacy (Yakkyoku), 2007, vol. 58, No. 4, pp. 605-616.
Kovac, A. Prophylaxis of postoperative nausea and vomiting: controversies in the use of serotonin 5-hydroxytryptamine subtype 3 receptor antagonists. J Clin Anesth. Jun. 2006;18(4):304-18.
Lainez MJ, et al. Optimal management of severe nausea and vomiting in migraine: improving patient outcomes. Patient Relat Outcome Meas. 2013;4:61-73.
Lipton RB, Stewart WF, Diamond S, Diamond ML, Reed M. Prevalence and burden of migraine in the United States: data from the American Migraine Study II. Headache. 2001;41(7):646-657.
Mayo Clinic Website. Cough and Cold Combination (Oral Route). Available at www.mayoclinic.com/health/drug-infomation/DR602361. Accessed Oct. 2, 2007.
Migraine Information Page. National Institute of Neurological Disorders and Stroke: https://www.ninds.nih.gov/Disorders/All-Disorders/Migraine-Information-Page. Accessed Jun. 9, 2017. [Retrieved Jan. 29, 2018].
Moser, et al. No more than necessary: Safety and efficacy of low-dose promethazine. Annals of Pharmacotherapy. 2006; 40:45-48.
Naratriptan Hydrochloride. Orange book: approved drug products with therapeutic equivalence evaluations. FDA. www.accessdata.fda.gov. Updated Aug. 21, 2014.
Noh, et al. Brain 21 (2005) vol. 8, No. 4, pp. 62-67.
Notice of allowance dated Oct. 5, 2015 for U.S. Appl. No. 13/347,552.
Office action dated Feb. 29, 2012 for U.S. Appl. No. 12/967,423.
Office action dated Feb. 7, 2013 for U.S. Appl. No. 12/444,521.
Office action dated Jun. 29, 2012 for U.S. Appl. No. 12/444,521.
Office action dated Jul. 17, 2014 for U.S. Appl. No. 13/347,552.
Office action dated Sep. 6, 2012 for U.S. Appl. No. 12/967,423.
Office action dated Sep. 20, 2010 for U.S. Appl. No. 12/351,704.

(56) References Cited

OTHER PUBLICATIONS

Promethazine Hydrochloride. Orange book: approved drug products with therapeutic equivalence evaluations. FDA. www.accessdata.fda.gov. Updated Aug. 21, 2014.
Promethazine, Description and Brand Names Drug Information by Micromedex Retrieved Mar. 27, 2017 from: http://www.mayoclinic.org/drugs-supplements/promethazine-oral-route/description/drg-20070609?p=1; pp. 1-17.
Prosolve Data Sheet [online] retrieved on Feb. 27, 2012 from: http://www.jrspharma.de/Pharma/wEnglisch/produktinfo/prosolv_smcc/prosolv_smcc_grades.shtml; 2 pages.
Ragg, et al. Comparison of the efficacy of paracetamol versus paracetamol, codeine and promethazine (Painstop) for premedication and analgesia for myringotomy in children. Anaesth Intensive Care. Feb. 1997;25(1):29-32.
Rizatriptan Benzoate. Orange book: approved drug products with therapeutic equivalence evaluations. FDA. www.accessdata.fda.gov. Updated Aug. 21, 2014.
Silverman, et al. Influence of promethazine on symptom-therapy scores for nausea during patient-controlled analgesia with morphine. Anesth Analg. May 1992;74(5):735-8.
Strenkoski-Nix, et al. Pharmacokinetics of promethazine hydrochloride after administration of rectal suppositories and oral syrup to healthy subjects. Am J Health Syst Pharm. Aug. 15, 2000;57(16):1499-505.
Sumatriptan Succinate. Orange book: approved drug products with therapeutic equivalence evaluations. FDA. www.accessdata.fda.gov. Updated Aug. 21, 2014.
Suzuki Takahiro. Utilize codeine phosphate. Journal of Pain and Clinical Medicine (2006), vol. 6, No. 1, p. 77-82. (in Japanese with English translation).
Takahiro, S. et al. Journal of Pain and Clinical Medicine, 2006, vol. 6, No. 1, p. 77-82.
Tarkkila, et al. Premedication with promethazine and transdermal scopolamine reduces the incidence of nausea and vomiting after intrathecal morphine. Acta Anaesthesiol Scand. Oct. 1995;39(7):983-6.
Tfelt-Hansen, et al. Triptans in migraine: a comparative review of pharmacology, pharmacokinetics and efficacy. Drugs. Dec. 2000;60(6):1259-87.
U.S. Appl. No. 14/099,432 Non-Final Office Action dated Feb. 22, 2017.
U.S. Appl. No. 14/683,886 Final Office Action dated Jun. 6, 2018.
U.S. Appl. No. 14/789,883 Office Action dated Sep. 9, 2016.
U.S. Appl. No. 14/925,669 Office Action dated Nov. 18, 2016.
U.S. Appl. No. 14/925,669 Supplemental Notice of Allowability dated Jul. 21, 2017.
U.S. Appl. No. 14/930,496 Office Action dated Dec. 2, 2016.
U.S. Appl. No. 15/206,955 Notice of Allowability dated Nov. 10, 2016.
U.S. Appl. No. 15/206,955 Office Action dated Aug. 11, 2016.
U.S. Appl. No. 15/263,230 Non-final Office Action dated Feb. 7, 2017.
U.S. Appl. No. 15/263,235 Final Office Action dated Nov. 28, 2018.
U.S. Appl. No. 15/263,235 Non-Final Office Action dated Dec. 30, 2016.
U.S. Appl. No. 15/263,235 Non-Final Office Action dated Feb. 23, 2018.
U.S. Appl. No. 15/263,243 Office Action dated Dec. 19, 2016.
U.S. Appl. No. 15/449,798 Non-Final Office Action dated Feb. 23, 2018.
U.S. Appl. No. 15/449,798 Notice of Allowance dated Jul. 12, 2018.
U.S. Appl. No. 15/452,628 Non-Final Office Action dated Jun. 29, 2018.
U.S. Appl. No. 15/618,998 Non-Final Office Action dated Dec. 5, 2018.
U.S. Appl. No. 15/676,761 Non-Final Office Action dated Aug. 10, 2018.
U.S. Appl. No. 15/683,635 Non-Final Office Action dated Oct. 6, 2017.
U.S. Appl. No. 15/683,643 Non-Final Office Action dated Oct. 5, 2017.
U.S. Appl. No. 15/683,646 Final Office Action dated Jul. 3, 2018.
U.S. Appl. No. 15/683,646 Non-Final Office Action dated Oct. 6, 2017.
U.S. Appl. No. 16/038,099 Non-Final Office Action dated Sep. 17, 2018.
Vinson, D.R. Treatment patterns of isolated benign headache in US emergency departments. Ann Emerg Med. Mar. 2002;39(3):215-22. (Abstract).
Vollbracht, et al. New treatments for headache. Neurol Sci. May 2014;35 Suppl 1:89-97.
Watcha, et al. Postoperative nausea and vomiting. Its etiology, treatment, and prevention. Anesthesiology. Jul. 1992;77(1):162-84.
Wyeth Phenergan (promethazine HCl) Label (2004) pp. 1-10.
Yaghmour, et al. Multimodal Anesthesia and Analgesia Facilitates Ambulatory Discharge of Patients Undergoing Osseous Reconstructive Ankle Surgery (RAS). Anesthesiology 2003; 99: A19 URL:http://www.asaabstracts.com/strands/asaabstracts/abstract.htm;jsessionid=D8FB91F2211878C2D0D08A062AA48B1E?year=2003&index=1&absnum=1516.
Zolmitriptan. Orange book: approved drug products with therapeutic equivalence evaluations. FDA. www.accessdata.fda.gov. Updated Aug. 21, 2014.
European Search report for EP Appl. No. 17760951.8 dated Aug. 13, 2019.
Final Office Action dated May 31, 2019, for U.S. Appl. No. 16/038,099.
Olver, Ian et al., Nanomedicines in the treatment of emesis during chemotherapy: focus on aprepitant, International Journal of Nanomedi, Dov Medical Press, Ltd., Auckland, NZ, vol. 2, No. 1, May 1, 2007, pp. 13-18, XP009152304.

* cited by examiner

SUMATRIPTAN PROMETHAZINE PHARMACEUTICAL COMPOSITIONS

CROSS REFERENCE

This application is a continuation of U.S. patent application Ser. No. 15/449,798, filed Mar. 3, 2017, which claims the benefit of U.S. Provisional Application Ser. No. 62/304,074 filed Mar. 4, 2016 and U.S. Provisional Application Ser. No. 62/415,991 filed Nov. 1, 2016, the contents of which are hereby incorporated by reference in their entireties.

BACKGROUND

Available pain medications are typically provided in individual doses. The therapeutic effects of these medications may be improved by combining them with other medications capable of providing relief for ailments other than pain, such as nausea and vomiting. In some cases, subjects suffering pain experience these additional ailments. Accordingly, combination therapies may also address the need for effective therapeutics for pain relief.

BRIEF SUMMARY

Provided herein is a particulate, the particulate comprising: a $5HT_{1B/1D}$ receptor agonist, wherein the particulate has an average diameter of less than about 500 μm, and wherein at least about 80% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddles) rotating at 50 rpm. In some embodiments, the particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, the particulate is in the form of a homogeneous mixture. In some embodiments, the particulate comprises about 60% of the $5HT_{1B/1D}$ receptor agonist (w/w). In some embodiments, the particulate has an average diameter of between about 100 μm and about 500 μm. In some embodiments, at least about 81% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 89% of the $5HT_{1B/1D}$ receptor agonist is released within about 10 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 15 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the $5HT_{1B/1D}$ receptor agonist is released within about 20 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the pharmaceutically acceptable salt of sumatriptan comprises sumatriptan succinate.

Provided herein is a particulate, the particulate comprising: a $5HT_{1B/1D}$ receptor agonist, wherein the particulate comprises from about 55% to about 65% of the $5HT_{1B/1D}$ receptor agonist (w/w), and wherein at least about 80% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddles) rotating at 50 rpm. In some embodiments, the particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, the particulate is in the form of a homogeneous mixture. In some embodiments, the particulate comprises about 60% of the $5HT_{1B/1D}$ receptor agonist (w/w). In some embodiments, the particulate has an average diameter of between about 100 μm and about 500 μm. In some embodiments, at least about 81% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 89% of the $5HT_{1B/1D}$ receptor agonist is released within about 10 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 15 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the $5HT_{1B/1D}$ receptor agonist is released within about 20 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the pharmaceutically acceptable salt of sumatriptan comprises sumatriptan succinate.

Provided herein is a particulate, the particulate comprising: a $5HT_{1B/1D}$ receptor agonist wherein (a) the particulate has an average diameter of less than about 500 µm; and (b) the particulate comprises from about 55% to about 65% of the $5HT_{1B/1D}$ receptor agonist (w/w). In some embodiments, the particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, the particulate is in the form of a homogeneous mixture. In some embodiments, the particulate comprises about 60% of the $5HT_{1B/1D}$ receptor agonist (w/w). In some embodiments, the particulate has an average diameter of between about 100 µm and about 500 µm. In some embodiments, at least about 81% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 89% of the $5HT_{1B/1D}$ receptor agonist is released within about 10 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 15 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the $5HT_{1B/1D}$ receptor agonist is released within about 20 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the pharmaceutically acceptable salt of sumatriptan comprises sumatriptan succinate.

Provided herein is a pharmaceutical composition comprising: a plurality of first particulates, wherein each first particulate comprises: a $5HT_{1B/1D}$ receptor agonist wherein: (a) each first particulate has an average diameter of less than about 500 µm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopramide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm.

Provided herein is an oral dosage form comprising a pharmaceutical composition comprising: a plurality of first particulates, wherein each first particulate comprises: a $5HT_{1B/1D}$ receptor agonist wherein: (a) each first particulate has an average diameter of less than about 500 µm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm.

Provided herein is a capsule comprising a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, the second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopramide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 32% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 63% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 79% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 88% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 56% of the $5HT_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 81% of the $5HT_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm.

Provided herein is a capsule comprising a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic; wherein the dissolution profile of the capsule stored at 40° C. for one month is: at least about 47% of the $5HT_{1B/1D}$ receptor agonist is released within about 5 minutes, or at least about 69% of the $5HT_{1B/1D}$ receptor agonist is released within about 15 minutes, or at least about 80% of the $5HT_{1B/1D}$ receptor agonist is released within about 30 minutes, or at least about 86% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm; and at least about 35% of the antiemetic is released within about 5 minutes, or at least about 63% of the antiemetic is released within about 15 minutes, or at least about 74% of the antiemetic agonist is released within about 30 minutes, or at least about 84% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 60% of the $5HT_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 81% of the $5HT_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 88% of the $5HT_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 93% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 43% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 73% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 92% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm.

Provided herein is a capsule comprising a pharmaceutical composition comprising: a plurality of first particulates, wherein each first particulate comprises: (i) about 100 mg to about 140 mg of sumatriptan succinate; and (ii) about 50 mg to about 150 mg of microcrystalline cellulose; and a plurality of second particulates, wherein each second particulate comprises: (i) about 10 mg to about 60 mg of promethazine hydrochloride; (ii) about 30 mg to about 150 mg of a sugar sphere; (iii) about 2.5 mg to about 15 mg of hydroxypropyl methylcellulose (HPMC); (iv) about 0.5 mg to about 10 mg of talc; (v) about 0.5 mg to about 10 mg of low-substituted hydroxypropyl cellulose (L-HPC); and (vi) about 5 mg to about 30 mg of a coating. In some embodiments, each first particulate has an average diameter of less than about 500 μm.

Provided herein is a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 μm; and a plurality of second particulates, wherein each second particulate comprises: (i) about 25 mg of promethazine hydrochloride; (ii) about 66.6 mg of a sugar sphere; (iii) about 6.6 mg of hydroxypropyl methylcellulose (HPMC); (iv) about 1.2 mg of talc; (v) about 2.5 mg of low-substituted hydroxypropyl cellulose (L-HPC); and (vi) about 10.2 mg of a coating.

Provided herein is a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 μm; and a plurality of second particulates, wherein each second particulate comprises: (i) about 50 mg of promethazine hydrochloride; (ii) about 133.2 mg of a sugar sphere; (iii) about 13.2 mg of hydroxypropyl methylcellulose (HPMC); (iv) about 2.4 mg of talc; (v) about 5 mg of low-substituted hydroxypropyl cellulose (L-HPC); and (vi) about 20.4 mg of a coating.

Provided herein is a method of treating a headache in a subject in need thereof, comprising administering to the subject a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the headache is acute or prophylactic. In some embodiments, the headache is a migraine headache. In some embodiments, the headache is an acute migraine headache or a chronic migraine headache. In some embodiments, the headache is a migraine headache with or without an aura. In some embodiments, the headache is a cluster headache. In some embodiments, the pharmaceutical composition, oral dosage, or capsule is used for treatment of nausea associated with a headache and vomiting associated with a headache. In some embodiments, the pharmaceutical composition, oral dosage, or capsule is suitable for use at one, two, or three times daily. In some embodiments, the pharmaceutical composition, oral dosage, or capsule is suitable for use at about every 4 to about every 6 hours. In some embodiments, a second dose of the pharmaceutical composition, oral dosage, or capsule is used after response to a first dose in a subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a headache in a subject in need thereof, comprising administering to the subject an oral dosage form comprising a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 μm and about 500 μm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprise from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 μm and about 1200 μm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the headache is acute or prophylactic. In some embodiments, the headache is a migraine headache. In some embodiments, the headache is an acute migraine headache or a chronic migraine headache. In some embodiments, the headache is a migraine headache with or without an aura. In some embodiments, the headache is a cluster headache. In some embodiments, the pharmaceutical composition, oral dosage, or capsule is used for treatment of nausea associated with a headache and vomiting associated with a headache. In some embodiments, the pharmaceutical composition, oral dosage, or capsule is suitable for use at one, two, or three times daily. In some embodiments, the pharmaceutical composition, oral dosage, or capsule is suitable for use at about every 4 to about every 6 hours. In some embodiments, a second dose of the pharmaceutical composition, oral dosage, or capsule is used after response to a first dose in a subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a headache in a subject in need thereof, comprising administering to the subject a capsule comprising a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 μm and about 500 μm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, the second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 32% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 63% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 79% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 88% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 56% of the $5HT_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 81% of the $5HT_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the headache is acute or prophylactic. In some embodiments, the headache is a migraine headache. In some embodiments, the headache is an acute migraine headache or a chronic migraine headache. In some embodiments, the headache is a migraine headache with or without an aura. In some embodiments, the headache is a cluster headache. In some embodiments, the pharmaceutical composition, oral dosage, or capsule is used for treatment of nausea associated with a headache and vomiting associated with a headache. In some embodiments, the pharmaceutical composition, oral dosage, or capsule is suitable for use at one, two, or three times daily. In some embodiments, the pharmaceutical composition, oral dosage, or capsule is suitable for use at about every 4 to about every 6 hours. In some embodiments, a second dose of the pharmaceutical composition, oral dosage, or capsule is used after response to a first dose in a subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a headache in a subject in need thereof, comprising administering to the subject a capsule comprising a pharmaceutical composition comprising: a plurality of first particulates, wherein each first particulate comprises: (i) about 100 mg to about 140 mg of sumatriptan succinate; and (ii) about 50 mg to about 150 mg of microcrystalline cellulose; and a plurality of second particulates, wherein each second particulate comprises: (i) about 10 mg to about 60 mg of promethazine hydrochloride; (ii) about 30 mg to about 150 mg of a sugar sphere; (iii) about 2.5 mg to about 15 mg of hydroxypropyl methylcellulose (HPMC); (iv) about 0.5 mg to about 10 mg of talc; (v) about 0.5 mg to about 10 mg of low-substituted hydroxypropyl cellulose (L-HPC); and (vi) about 5 mg to about 30 mg of a coating. Provided herein is a method of treating a headache in a subject in need thereof, comprising administering to the subject a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 µm; and a plurality of second particulates, wherein each second particulate comprises: (i) about 25 mg of promethazine hydrochloride; (ii) about 66.6 mg of a sugar sphere; (iii) about 6.6 mg of hydroxypropyl methylcellulose (HPMC); (iv) about 1.2 mg of talc; (v) about 2.5 mg of low-substituted hydroxypropyl cellulose (L-HPC); and (vi) about 10.2 mg of a coating. Provided herein is a method of treating a headache in a subject in need thereof, comprising administering to the subject a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 µm; and a plurality of second particulates, wherein each second particulate comprises: (i) about 50 mg of promethazine hydrochloride; (ii) about 133.2 mg of a sugar sphere; (iii) about 13.2 mg of hydroxypropyl methylcellulose (HPMC); (iv) about 2.4 mg of talc; (v) about 5 mg of low-substituted hydroxypropyl cellulose (L-HPC); and (vi) about 20.4 mg of a coating. In some embodiments, each first particulate has an average diameter of less than about 500 µm. In some embodiments, the treatment of the headache is acute or prophylactic. In some embodiments, the headache is a migraine headache. In some embodiments, the headache is an acute migraine headache or a chronic migraine headache. In some embodiments, the headache is a migraine headache with or without an aura. In some embodiments, the headache is a cluster headache. In some embodiments, the pharmaceutical composition, oral dosage, or capsule is used for treatment of nausea associated with a headache and vomiting associated with a headache. In some embodiments, the pharmaceutical composition, oral dosage, or capsule is suitable for use at one, two, or three times daily.

In some embodiments, the pharmaceutical composition, oral dosage, or capsule is suitable for use at about every 4 to about every 6 hours. In some embodiments, a second dose of the pharmaceutical composition, oral dosage, or capsule is used after response to a first dose in a subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a headache in a subject in need thereof, comprising administering to the subject a capsule comprising a pharmaceutical composition comprising: a plurality of first particulates, wherein each first particulate comprises: a $5HT_{1B/1D}$ receptor agonist wherein: (a) each first particulate has an average diameter of less than about 500 µm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic; wherein the dissolution profile of the capsule stored at 40° C. for one month is: at least about 47% of the $5HT_{1B/1D}$ receptor agonist is released within about 5 minutes, or at least about 69% of the $5HT_{1B/1D}$ receptor agonist is released within about 15 minutes, or at least about 80% of the $5HT_{1B/1D}$ receptor agonist is released within about 30 minutes, or at least about 86% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm; and at least about 35% of the antiemetic is released within about 5 minutes, or at least about 63% of the antiemetic is released within about 15 minutes, or at least about 74% of the antiemetic agonist is released within about 30 minutes, or at least about 84% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 60% of the $5HT_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 81% of the $5HT_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 88% of the $5HT_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 93% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 43% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 73% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 92% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the headache is acute or prophylactic. In some embodiments, the headache is a migraine headache. In some embodiments, the headache is an acute migraine headache or a chronic migraine headache. In some embodiments, the headache is a migraine headache with or without an aura. In some embodiments, the headache is a cluster headache. In some embodiments, the pharmaceutical composition, oral dosage, or capsule is used for treatment of nausea associated with a headache and vomiting associated with a headache. In some embodiments, the pharmaceutical composition, oral dosage, or capsule is suitable for use at one, two, or three times daily. In some embodiments, the pharmaceutical composition, oral dosage, or capsule is suitable for use at about every 4 to about every 6 hours. In some embodiments, a second dose of the pharmaceutical composition, oral dosage, or capsule is used after response to a first dose in a subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a photophobia in a subject in need thereof, comprising administering to the subject a pharmaceutical composition comprising: a plurality of first particulates, wherein each first particulate comprises: a $5HT_{1B/1D}$ receptor agonist wherein: (a) each first particulate has an average diameter of less than about 500 μm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 μm and about 500 μm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 μm and about 1200 μm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the photophobia is acute or prophylactic. In some embodiments, the pharmaceutical composition, oral dosage, or capsule is used for treatment of a light sensitivity. In some embodiments, the pharmaceutical composition, oral dosage, or capsule treats nausea associated with a headache or vomiting associated with a headache. In some embodiments, the pharmaceutical composition, oral dosage, or capsule treats nausea associated with a headache and vomiting associated with a headache. In some embodiments, the administering is one, two, or three times daily. In some embodiments, the administering is about every 4 to about every 6 hours. In some embodiments, the administering is about every 8 to about every 12 hours. In some embodiments, a second dose of the pharmaceutical composition, oral dosage, or capsule is administered after response to a first dose in the subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a photophobia in a subject in need thereof, comprising administering to the subject an oral dosage form comprising a pharmaceutical composition comprising: a plurality of first particulates, wherein each first particulate comprises: a $5HT_{1B/1D}$ receptor agonist wherein: (a) each first particulate has an average diameter of less than about 500 µm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, each second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, the promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 85% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 30 minutes following contact of the particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 96% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 75% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 98% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the photophobia is acute or prophylactic. In some embodiments, the pharmaceutical composition, oral dosage, or capsule is used for treatment of a light sensitivity. In some embodiments, the pharmaceutical composition, oral dosage, or capsule treats nausea associated with a headache or vomiting associated with a headache. In some embodiments, the pharmaceutical composition, oral dosage, or capsule treats nausea associated with a headache and vomiting associated with a headache. In some embodiments, the administering is one, two, or three times daily. In some embodiments, the administering is about every 4 to about every 6 hours. In some embodiments, the administering is about every 8 to about every 12 hours. In some embodiments, a second dose of the pharmaceutical composition, oral dosage, or capsule is administered after response to a first dose in the subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a photophobia in a subject in need thereof, comprising administering to the subject a capsule comprising a pharmaceutical composition comprising: a plurality of first particulates, wherein each first particulate comprises: a $5HT_{1B/1D}$ receptor agonist wherein: (a) each first particulate has an average diameter of less than about 500 µm; or (b) each first particulate comprises from about 55% to about 65% of the $5HT_{1B/1D}$ receptor agonist (w/w); and a plurality of second particulates, wherein each second particulate comprises: (i) a core; and (ii) a layer enclosing the core, wherein said layer comprises an antiemetic. In some embodiments, each first particulate further comprises a pharmaceutically acceptable excipient. In some embodiments, the pharmaceutically acceptable excipient is a non-pharmaceutically active ingredient. In some embodiments, the non-pharmaceutically active ingredient comprises at least one component selected from the group consisting of microcrystalline cellulose, dicalcium phosphate, calcium sulfate, talc, an alkali metal stearate, silicon dioxide, calcium carbonate, and any combinations thereof. In some embodiments, the at least one component is microcrystalline cellulose. In some embodiments, each first particulate comprises about 60% of the $5HT_{1B/1D}$ receptor agonist (w/w). In some embodiments, each first particulate comprises about 40% of the non-pharmaceutically active ingredient (w/w). In some embodiments, each first particulate has an average diameter of between about 100 µm and about 500 µm. In some embodiments, the layer enclosing the core in each second particulate is directly adjacent to the core. In some embodiments, the core in each second particulate does not comprise an antiemetic. In some embodiments, the core in each second particulate comprises a sugar sphere. In some embodiments, the layer enclosing the core in each second particulate comprises one or more pharmaceutically acceptable excipients. In some embodiments, the one or more pharmaceutically acceptable excipients is selected from hydroxypropyl methylcellulose (HPMC), low-substituted hydroxypropyl cellulose (L-HPC), talc, and any combinations thereof. In some embodiments, each second particulate comprises from about 2% to about 10% of hydroxypropyl methylcellulose (HPMC) (w/w). In some embodiments, each second particulate comprises from about 0.1% to about 2% of talc (w/w). In some embodiments, each second particulate comprises from about 1% to about 3% of low-substituted hydroxypropyl cellulose (L-HPC) (w/w). In some embodiments, each second particulate comprises from about 10% to about 40% of the antiemetic (w/w). In some embodiments, each second particulate comprises from about 50% to about 70% of a core (w/w). In some embodiments, each second particulate has an average diameter from about 700 µm and about 1200 µm. In some embodiments, each first particulate further comprises a first coating. In some embodiments, each second particulate further comprises a second coating. In some embodiments, the second particulate comprises from about 5% to about 15% of a second coating (w/w). In some embodiments, the first or second coating comprises polyvinyl alcohol, cellulose acetate phthalate, polyvinyl acetate phthalate, methacrylic acid copolymer, cellulose acetate trimellitate, hydroxypropyl methylcellulose phthalate, hydroxypropyl methylcellulose, hydroxypropyl methyl cellulose acetate succinate, shellac, sodium alginate, zein, or any combinations thereof. In some embodiments, the coating comprises polyvinyl alcohol. In some embodiments, the coating is polyvinyl alcohol. In some embodiments, the $5HT_{1B/1D}$ receptor agonist comprises a triptan or a pharmaceutically acceptable salt thereof. In some embodiments, the triptan or the pharmaceutically acceptable salt thereof comprises sumatriptan, almotriptan, frovatriptan, eletriptan, rizatriptan, naratriptan, or a pharmaceutically acceptable salt thereof. In some embodiments, the triptan or the pharmaceutically acceptable salt thereof comprises sumatriptan or a pharmaceutically acceptable salt thereof. In some embodiments, the sumatriptan or the pharmaceutically acceptable salt thereof is present in an amount therapeutically equivalent from about 70 mg to about 110 mg of sumatriptan free base. In some embodiments, the sumatriptan or the pharmaceutically acceptable salt thereof is present in an amount therapeutically equivalent to about 90 mg of sumatriptan free base. In some embodiments, the pharmaceutically acceptable salt of the sumatriptan comprises sumatriptan succinate. In some embodiments, the sumatriptan succinate is present in an amount from about 100 mg to about 140 mg. In some embodiments, the sumatriptan succinate is present in an amount of about 126 mg. In some embodiments, the antiemetic comprises promethazine, ondansetron, aprepitant, dronabinol, perphenazine, palonosetron, trimethyobenzamide, metoclopromide, domperidone, prochlorperazine, chlorpromazine, trimethobenzamide, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, or a pharmaceutically acceptable salt thereof. In some embodiments, the antiemetic comprises promethazine or a pharmaceutically acceptable salt thereof. In some embodiments, promethazine or the pharmaceutically acceptable salt thereof is present in an amount therapeutically equivalent from about 10 mg to about 60 mg promethazine free base. In some embodiments, the promethazine or the pharmaceutically acceptable salt thereof is present in an amount therapeutically equivalent to about 11 mg, about 22 mg, or about 44 mg of promethazine free base. In some embodiments, the pharmaceutically acceptable salt of promethazine comprises promethazine hydrochloride. In some embodiments, the promethazine hydrochloride is present in an amount from about 10 mg to about 60 mg. In some embodiments, the promethazine hydrochloride is present in an amount of about 12.5 mg, about 25 mg, or about 50 mg. In some embodiments, a ratio by weight of the $5HT_{1B/1D}$ receptor agonist to the antiemetic is from about 1:2 to about 15:1. In some embodiments, the ratio by weight of the $5HT_{1B/1D}$ receptor agonist to the antiemetic is from about 3:2 to about 11:1. In some embodiments, the ratio by weight of the $5HT_{1B/1D}$ receptor agonist to the antiemetic is from about 3:1 to about 7:1 or from about 1:1 to about 5:1. In some embodiments, the ratio by weight of the $5HT_{1B/1D}$ receptor agonist to the antiemetic is from about 9:2 to about 11:2 or from about 4:2 to about 6:2. In some embodiments, the ratio by weight of the $5HT_{1B/1D}$ receptor agonist to the antiemetic is about 5:1 or about 2.5:1. In some embodiments, at least about 32% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 63% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 79% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 88% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 56% of the $5HT_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 81% of the $5HT_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the photophobia is acute or prophylactic. In some embodiments, the pharmaceutical composition, oral dosage, or capsule is used for treatment of a light sensitivity. In some embodiments, the pharmaceutical composition, oral dosage, or capsule treats nausea associated with a headache or vomiting associated with a headache. In some embodiments, the pharmaceutical composition, oral dosage, or capsule treats nausea associated with a headache and vomiting associated with a headache. In some embodiments, the administering is one, two, or three times daily. In some embodiments, the administering is about every 4 to about every 6 hours. In some embodiments, the administering is about every 8 to about every 12 hours. In some embodiments, a second dose of the pharmaceutical composition, oral dosage, or capsule is administered after response to a first dose in the subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the $5HT_{1B/1D}$ receptor agonist does not exceed 50 mg in a subject with mild to moderate hepatic impairment.

Provided herein is a method of treating a photophobia in a subject in need thereof, comprising administering to the subject a capsule comprising a pharmaceutical composition comprising: a plurality of first particulates, wherein each first particulate comprises: (i) about 100 mg to about 140 mg of sumatriptan succinate; and (ii) about 50 mg to about 150 mg of microcrystalline cellulose; and a plurality of second particulates, wherein each second particulate comprises: (i) about 10 mg to about 60 mg of promethazine hydrochloride; (ii) about 30 mg to about 150 mg of a sugar sphere; (iii) about 2.5 mg to about 15 mg of hydroxypropyl methylcellulose (HPMC); (iv) about 0.5 mg to about 10 mg of talc; (v) about 0.5 mg to about 10 mg of low-substituted hydroxypropyl cellulose (L-HPC); and (vi) about 5 mg to about 30 mg of a coating. In some embodiments, each first particulate has an average diameter of less than about 500 µm. Provided herein is a method of treating a photophobia in a subject in need thereof, comprising administering to the subject a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 µm; and a plurality of second particulates, wherein each second particulate comprises: (i) about 25 mg of promethazine hydrochloride; (ii) about 66.6 mg of a sugar sphere; (iii) about 6.6 mg of hydroxypropyl methylcellulose (HPMC); (iv) about 1.2 mg of talc; (v) about 2.5 mg of low-substituted hydroxypropyl cellulose (L-HPC); and (vi) about 10.2 mg of a coating. Provided herein is a method of treating a photophobia in a subject in need thereof, comprising administering to the subject a capsule comprising a pharmaceutical composition comprising: a plurality of first particulates, wherein each first particulate comprises: (i) about 126 mg of sumatriptan succinate; and (ii) about 84 mg of microcrystalline cellulose; wherein each first particulate has an average diameter of less than about 500 µm; and a plurality of second particulates, wherein each second particulate comprises: (i) about 50 mg of promethazine hydrochloride; (ii) about 133.2 mg of a sugar sphere; (iii) about 13.2 mg of hydroxypropyl methylcellulose (HPMC); (iv) about 2.4 mg of talc; (v) about 5 mg of low-substituted hydroxypropyl cellulose (L-HPC); and (vi) about 20.4 mg of a coating. In some embodiments, the treatment of the photophobia is acute or prophylactic. In some embodiments, the pharmaceutical composition, oral dosage, or capsule is used for treatment of a light sensitivity. In some embodiments, the pharmaceutical composition, oral dosage, or capsule treats nausea associated with a headache or vomiting associated with a headache. In some embodiments, the pharmaceutical composition, oral dosage, or capsule treats nausea associated with a headache and vomiting associated with a headache. In some embodiments, the administering is one, two, or three times daily. In some embodiments, the administering is about every 4 to about every 6 hours. In some embodiments, the administering is about every 8 to about every 12 hours. In some embodiments, a second dose of the pharmaceutical composition, oral dosage, or capsule is administered after response to a first dose in the subject. In some embodiments, doses after a first dose of the pharmaceutical composition, oral dosage, or capsule are separated by at least 2 hours. In some embodiments, a maximum dose of the $5HT_{1B/1D}$ receptor agonist over 24 hour does not exceed 200 mg. In some embodiments, a maximum single dose of the 5HT$_{1B/1D}$ receptor agonist does not exceed 50 mg in a subject with mild to moderate hepatic impairment.

Provided herein is a method of treating a photophobia in a subject in need thereof, comprising administering to the subject a capsule comprising a pharmaceutical composition comprising: a plurality of first particulates, wherein each first particulate comprises: a 5HT$_{1B/1D}$ receptor agonist wherein: (a) each first particulate has an average diameter of less than about 500 µm; or (b) each first particulate comprises from about 55% to about 65% of the 5HT$_{1B/1D}$ receptor agonist (w/w); and a plurality of second particulates, wherein each second particulate comprises: (i) a core; and (ii) a layer enclosing the core, wherein said layer comprises an antiemetic; wherein the dissolution profile of the capsule stored at 40° C. for one month is: at least about 47% of the 5HT$_{1B/1D}$ receptor agonist is released within about 5 minutes, or at least about 69% of the 5HT$_{1B/1D}$ receptor agonist is released within about 15 minutes, or at least about 80% of the 5HT$_{1B/1D}$ receptor agonist is released within about 30 minutes, or at least about 86% of the 5HT$_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm; and at least about 35% of the antiemetic is released within about 5 minutes, or at least about 63% of the antiemetic is released within about 15 minutes, or at least about 74% of the antiemetic agonist is released within about 30 minutes, or at least about 84% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 60% of the 5HT$_{1B/1D}$ receptor agonist is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 81% of the 5HT$_{1B/1D}$ receptor agonist is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 88% of the 5HT$_{1B/1D}$ receptor agonist is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 93% of the 5HT$_{1B/1D}$ receptor agonist is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 43% of the antiemetic is released within about 5 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 73% of the antiemetic is released within about 15 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the antiemetic is released within about 30 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 92% of the antiemetic is released within about 60 minutes following contact of the capsule with 500 mL of a dissolution fluid (0.1N HCl, pH 1.1) at 37+/−0.5° C. as measured by an Apparatus 2 (Paddle Apparatus) rotating at 50 rpm. In some embodiments, the treatment of the photophobia is acute or prophylactic. In some embodiments, the pharmaceutical composition, oral dosage, or capsule is used for treatment of a light sensitivity. In some embodiments, the pharmaceutical composition, oral dosage, or capsule treats nausea associated with a headache or vomiting associated with a headache. In some embodiments, the pharmaceutical composition, oral dosage, or capsule treats nausea associated with a headache and vomiting associated with a headache. In some embodiments, the administering is one, two, or three times daily. In some embodiments, the administering is about every 4 to about every 6 hours. In some embodiments, the administering is about every 8 to about every 12 hours. In some embodiments, a second dose of the pharmaceutical composition, oral dosage, or capsule is administered after response to a first dose in the subject. In some embodiments, doses after a first dose of the pharmaceutical composition, oral dosage, or capsule are separated by at least 2 hours. In some embodiments, a maximum dose of the 5HT$_{1B/1D}$ receptor agonist over 24 hour does not exceed 200 mg. In some embodiments, a maximum single dose of the 5HT$_{1B/1D}$ receptor agonist does not exceed 50 mg in a subject with mild to moderate hepatic impairment.

Provided herein are particulates, compositions, and capsules comprising an antiemetic, wherein the antiemetic is in a rapid release matrix. In some embodiments, the antiemetic is promethazine or a pharmaceutically acceptable salt thereof. In some embodiments, the promethazine is promethazine hydrocholoride. In some embodiments, the promethazine is present in an amount of from about 12.5 mg to about 60 mg. In some embodiments, the promethazine hydrochloride is present in an amount of from about 12.5 mg to about 60 mg. In some embodiments, the promethazine hydrochloride is present in an amount of 25 mg or 50 mg. In some embodiments, the promethazine base is present in an amount of 22 mg or 44 mg. In some embodiments, a capsule comprises from about 50 mg to about 150 mg of sumatriptan or a pharmaceutically acceptable salt thereof and from about 12.5 to about 60 mg of promethazine or a pharmaceutically acceptable salt thereof. In some embodiments, the capsule comprises from about 50 mg to about 150 mg of sumatriptan succinate and from about 12.5 to about 60 mg of promethazine hydrochloride. In some embodiments, the capsule comprises about 126 mg of sumatriptan succinate and about 50 mg of promethazine hydrochloride.

INCORPORATION BY REFERENCE

Figure 1:
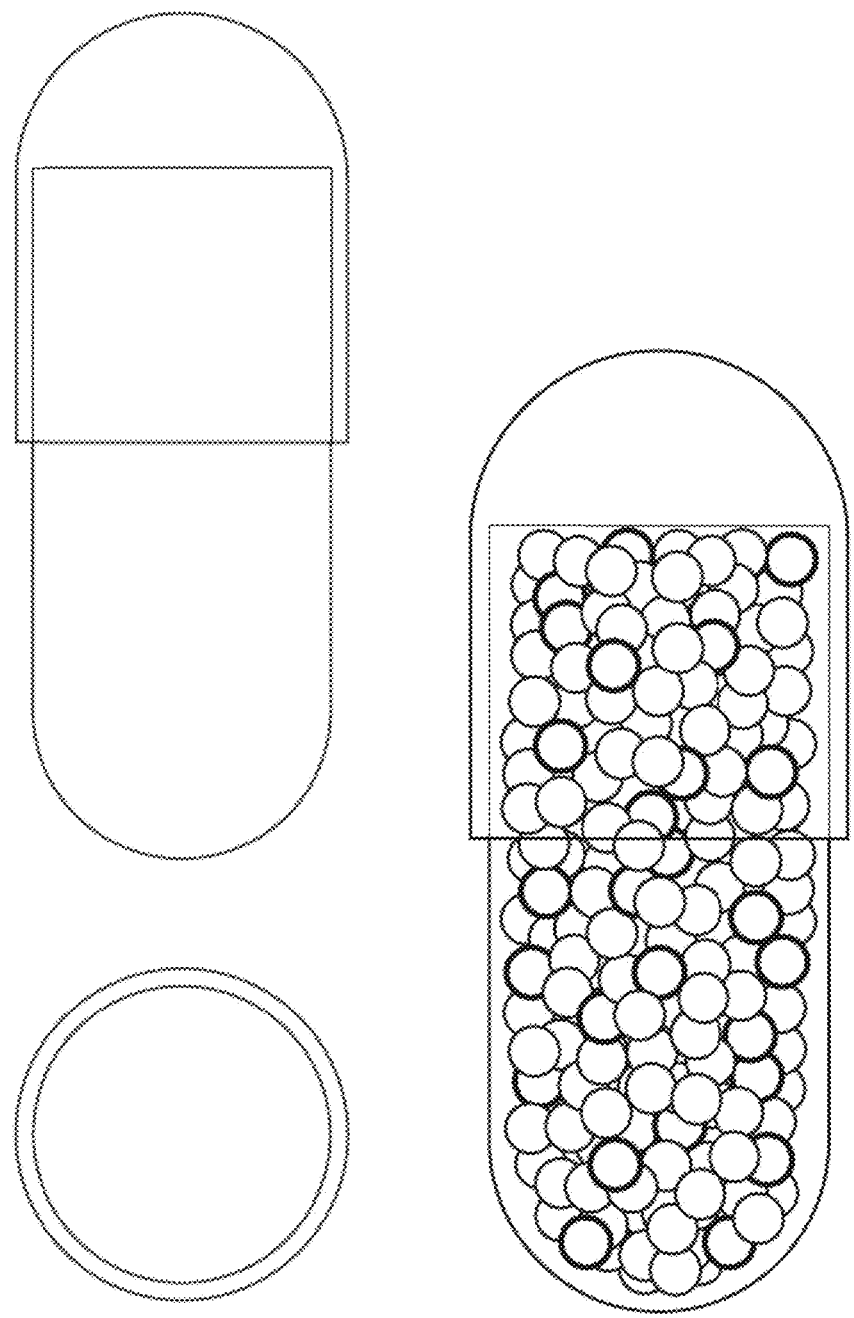
FIG. 1 illustrates an exemplary capsule, unfilled (left, in side and bottom view) or filled (right) with particulates. Particulates are not drawn to scale.

All publications, patents, and patent applications described herein are incorporated by reference to the same extent as if each individual publication, patent, or patent application was specifically and individually indicated to be incorporated by reference. In the event of a conflict between a term disclosed herein and a term in an incorporated reference, the term herein controls.

DETAILED DESCRIPTION

This disclosure is generally directed to compositions comprising multiple pharmaceutically active agents for the alleviation, abatement or elimination of one or more conditions in a subject in need thereof, as further described herein below.

Definitions

A "therapeutically effective amount" when used in connection with a pharmaceutical composition described herein is an amount of one or more pharmaceutically active agent(s) sufficient to produce a therapeutic result in a subject in need thereof. For example, a therapeutic result includes, but is not limited to, treating pain, migraine headache, nausea, vomiting, photophobia, phonophobia or osmophobia by a subject.

"Therapeutically equivalent" when used in connection with a pharmaceutical composition described herein refers to an amount or quantity of a pharmaceutically acceptable salt of a pharmaceutically active agent that is equivalent to the therapeutically effective amount of the free base of the pharmaceutically active agent.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

In some embodiments, a pharmaceutical composition described herein comprises a plurality of first particulates comprising a therapeutically effective amount of a first pharmaceutically active agent; and a plurality of second particulates comprising a therapeutically effective amount of a second pharmaceutically active agent. Pharmaceutically active agents disclosed herein are capable of use in a pharmaceutical composition as described herein. In some embodiments, a pharmaceutically active agent is a $5HT_{1B/1D}$ receptor agonist or an antiemetic.

In some embodiments, a pharmaceutical composition described herein comprises a plurality of first particulates, wherein each first particulate comprises: about 100 mg to about 140 mg of sumatriptan succinate; and about 50 mg to about 150 mg of microcrystalline cellulose; and a plurality of second particulates, wherein each second particulate comprises: about 10 mg to about 60 mg of promethazine hydrochloride; about 30 mg to about 150 mg of a sugar sphere; about 2.5 mg to about 15 mg of hydroxypropyl methylcellulose (HPMC); about 0.5 mg to about 10 mg of talc; about 0.5 mg to about 10 mg of low-substituted hydroxypropyl cellulose (L-HPC); and about 5 mg to about 30 mg of a coating. In some embodiments, each first particulate has an average diameter of less than about 500 µm. In some embodiments, a pharmaceutical composition described herein comprises a plurality of first particulates comprising: about 126 mg of sumatriptan succinate; and about 84 mg of microcrystalline cellulose; wherein each first particulate has an average diameter of less than about 500 µm; and a plurality of second particulates comprising: about 25 mg of promethazine hydrochloride; about 66.6 mg of a sugar sphere; about 6.6 mg of hydroxypropyl methylcellulose (HPMC); about 1.2 mg of talc; about 2.5 mg of low-substituted hydroxypropyl cellulose (L-HPC); and about 10.2 mg of a coating. In some embodiments, a pharmaceutical composition described herein comprises a plurality of first particulates comprising: about 126 mg of sumatriptan succinate; and about 84 mg of microcrystalline cellulose; wherein each first particulate has an average diameter of less than about 500 µm; and a plurality of second particulates comprising: about 50 mg of promethazine hydrochloride; about 133.2 mg of a sugar sphere; about 13.2 mg of hydroxypropyl methylcellulose (HPMC); about 2.4 mg of talc; about 5 mg of low-substituted hydroxypropyl cellulose (L-HPC); and about 20.4 mg of a coating.

$5HT_{1B/1D}$ Receptor Agonists

In some embodiments, the pharmaceutical composition disclosed herein comprises a $5HT_{1B/1D}$ receptor agonist. Exemplary $5HT_{1B/1D}$ receptor agonists include, without limitation, ergotamine and triptan family compounds. Exemplary triptans include, without limitation, sumatriptan, almotriptan, frovatriptan, eletriptan, rizatriptan, and naratriptan. In some embodiments, the pharmaceutical composition disclosed herein comprises a triptan or triptan analog. Triptan analogs are generally a family of tryptamine based drugs used for the treatment of migraines and headaches. Their action is attributed to their binding to serotonin receptors in nerve ending and in cranial blood vessels (causing their constriction) and subsequent inhibition of pro-inflammatory neuropeptide release. Exemplary triptans include, sumatriptan, almotriptan, forvatriptan, rizatriptan, zolmitriptan, eletriptan, and naratriptan, and pharmaceutically acceptable salts thereof. In some embodiments, triptan is used in the pharmaceutical composition disclosed herein is a free base or in the form of pharmaceutically acceptable salt thereof, for example, in the form of succinate. In some embodiments, the triptan is sumatriptan or a pharmaceutically acceptable salt thereof.

In some embodiments, the pharmaceutical composition disclosed herein comprises a triptan or a pharmaceutically acceptable salt thereof that is present at a dose from about 1.0 mg to about 200 mg, including, but not limited to, from about 25 mg to about 100 mg, from about 35 mg to about 140 mg, from about 70 mg to about 140 mg, from about 80 mg to about 135 mg, from about 1.0 mg to about 25 mg, from about 25 mg to about 50 mg, from about 50 mg to about 100 mg, from about 100 mg to about 150 mg, from about 150 mg to about 200 mg, from about 1.0 mg to about 35 mg, from about 35 mg to about 70 mg, from about 70 mg to about 105 mg, from about 105 mg to about 140 mg, from about 140 mg to about 175 mg, or from about 175 mg to about 200 mg. In some embodiments, the pharmaceutical composition disclosed herein comprises a triptan or a pharmaceutically acceptable salt thereof that is present at a dosage from about 1.0 mg to about 200 mg, including, but not limited to, about 1.0 mg, about 1.5 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13.0 mg, about 13.5 mg, about 14.0 mg, about 14.5 mg, about 15.0 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, about 50 mg, about 55 mg, about 60 mg, about 65 mg, about 70 mg, about 75 mg, about 80 mg, about 85 mg, about 90 mg, about 95 mg, about 100, about 105 mg, about 110 mg, about 115 mg, about 120 mg, about 120.5 mg, about 121 mg, about 121.5 mg, about 122 mg, about 122.5 mg, about 123 mg, about 123.5 mg, about 124 mg, about 124.5 mg, about 125 mg, about 125.5 mg, about 126 mg, about 126.5 mg, about 127 mg, about 127.5 mg, about 128 mg, about 128.5 mg, about 129 mg, about 129.5 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg. In some embodiments, the triptan is sumatriptan or a pharmaceutically acceptable salt thereof. In some embodiments, the pharmaceutical composition disclosed herein comprises a pharmaceutically acceptable salt of triptan in a quantity therapeutically equivalent to triptan dosages disclosed herein. In some embodiments, the pharmaceutical composition disclosed herein comprises a pharmaceutically acceptable salt of sumatriptan in a quantity therapeutically equivalent to about 90 mg of sumatriptan free base.

In some embodiments, the amount of sumatriptan or a pharmaceutically acceptable salt thereof present in the pharmaceutical composition disclosed herein is equivalent to about 4 mg, about 6 mg, about 10 mg, about 25 mg, about 50 mg, about 85 mg, about 90 mg, or about 100 mg of sumatriptan free base. In some embodiments, the pharmaceutically acceptable salt of sumatriptan is sumatriptan succinate. In some embodiments, the amount of sumatriptan succinate present in the pharmaceutical composition disclosed herein is about 35 mg, about 70 mg, about 126 mg, or about 140 mg. In some embodiments, an amount of sumatriptan free base present in the pharmaceutical composition disclosed herein is from about 25 mg and about 50 mg, from about 50 mg to about 100 mg, or from about 75 mg to about 100 mg.

In some embodiments, the pharmaceutical composition disclosed herein comprises sumatriptan, or a pharmaceutically acceptable salt thereof, that is present at a free base dose from about 10 mg to about 200 mg, including, but not limited to, from about 25 mg to about 100 mg, from about 35 mg to about 140 mg, from about 70 mg to about 140 mg, from about 80 mg to about 135 mg, from about 10 mg to about 25 mg, from about 25 mg to about 50 mg, from about 50 mg to about 100 mg, from about 100 mg to about 150 mg, from about 150 mg to about 200 mg, from about 10 mg to about 35 mg, from about 35 mg to about 70 mg, from about 70 mg to about 105 mg, from about 105 mg to about 140 mg, from about 140 mg to about 175 mg, or from about 175 mg to about 200 mg. In some embodiments, the pharmaceutically acceptable salt of sumatriptan is sumatriptan succinate.

In some embodiments, the pharmaceutical composition disclosed herein comprises almotriptan or a pharmaceutically acceptable salt thereof, that is present at a dose from about 1.0 mg to about 50 mg, including, but not limited to, about 1.0 mg to about 30 mg, about 5.0 mg to about 25 mg, about 5.0 mg to about 15 mg, about 1.0 mg to about 5.0 mg, about 5.0 mg to about 10.0 mg, about 10.0 mg to about 15 mg, about 15 mg to about 20 mg, about 20 mg to about 25 mg, about 25 mg to about 30 mg, about 35 mg to about 40 mg, about 40 mg to about 45 mg, or about 45 mg to about 50 mg. In some embodiments, the pharmaceutical composition described herein comprises almotriptan or a pharmaceutically acceptable salt thereof, that is present at a dose from about 1.0 mg to about 50 mg, including, but not limited to, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, or about 50 mg. In some embodiments, the pharmaceutically acceptable salt of almotriptan is almotriptan malate.

In some embodiments, the pharmaceutical composition disclosed herein comprises eletriptan or a pharmaceutically acceptable salt thereof, that is present at a dose from about 10.0 mg to about 100 mg, including, but not limited to, about 10.0 mg to about 75 mg, about 10.0 mg to about 50 mg, about 10 mg to about 30 mg, about 30 mg to about 50 mg, about 50 mg to about 70 mg, about 70 mg to about 90 mg, about 10.0 mg to about 20 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, or about 90 mg to about 100 mg. In some embodiments, the pharmaceutical composition described herein comprises eletriptan or a pharmaceutically acceptable salt thereof, that is present at a dose from about 10.0 mg to about 100 mg, including, but not limited to, about 10.0 mg, about 10.5 mg, about 11.0 mg, about 12.0 mg, about 12.5 mg, about 13.0 mg, about 13.5 mg, about 14.0 mg, about 14.5 mg, about 15.0 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the pharmaceutically acceptable salt of eletriptan is eletriptan hydrobromide.

In some embodiments, the pharmaceutical composition disclosed herein comprises frovatriptan or a pharmaceutically acceptable salt thereof, that is present at a dose from about 0.5 mg to about 10.0 mg, including, but not limited to, about 0.5 mg to about 5.0 mg, about 1.0 mg to about 3.0 mg, about 0.5 mg to about 1.5 mg, about 1.5 mg to about 3.0 mg, about 3.0 mg to about 4.5 mg, about 4.5 mg to about 6.0 mg, about 6.0 mg to about 7.5 mg, about 7.5 mg to about 9.0 mg, about 9.0 mg to about 10.0 mg, about 0.5 mg to about 1.0 mg about 1.0 mg to about 2.0 mg, about 2.0 mg to about 3.0 mg, about 3.0 mg to about 4.0 mg, about 4.0 mg to about 5.0 mg, about 5.0 mg to about 6.0 mg, about 6.0 mg to about 7.0 mg, about 7.0 mg to about 8.0 mg, or about 8.0 mg to about 9.0 mg. In some embodiments, the pharmaceutical composition described herein comprises frovatriptan or a pharmaceutically acceptable salt thereof, that is present at a dose from about 0.5 mg to about 10.0 mg, including, but not limited to, about 0.5 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, or about 10.0 mg. In some embodiments, the pharmaceutically acceptable salt of frovatriptan is frovatriptan succinate.

In some embodiments, the pharmaceutical composition disclosed herein comprises rizatriptan or a pharmaceutically acceptable salt thereof, that is present at a dose from about 1.0 mg to about 50 mg, including, but not limited to, about 1.0 mg to about 75 mg, about 1.0 mg to about 50 mg, about 1.0 mg to about 25 mg, about 1.0 mg to about 15 mg, about 15 mg to about 30 mg, about 30 mg to about 45 mg, about 1.0 mg to about 5.0 mg, about 5.0 mg to about 10.0 mg, about 10.0 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg. In some embodiments, the pharmaceutical composition described herein comprises rizatriptan or a pharmaceutically acceptable salt thereof, that is present at a dose from about 1.0 mg to about 50 mg, including, but not limited to, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, or about 50 mg. In some embodiments, the pharmaceutically acceptable salt of rizatriptan is rizatriptan benzoate.

In some embodiments, the pharmaceutical composition disclosed herein comprises zolmitriptan or a pharmaceutically acceptable salt thereof, that is present at a dose from about 1.0 mg to about 25 mg, including, but not limited to, about 1.0 mg to about 15 mg, about 1.0 mg to about 10 mg, about 1.0 mg to about 7.5 mg, about 1.0 mg to about 7.0 mg, about 7.0 mg to about 14 mg, about 14 mg to about 25 mg, about 1.0 mg to about 2.5 mg, about 2.5 mg to about 5.0 mg, about 5.0 mg to about 7.5 mg, about 7.5 mg to about 10 mg, about 10 mg to about 12.5 mg, about 12.5 mg to about 15 mg, about 15 mg to about 17.5 mg, about 17.5 mg to about 20 mg, or about 20 mg to about 25 mg. In some embodiments, the pharmaceutical composition described herein comprises zolmitriptan or a pharmaceutically acceptable salt thereof, that is present at a dose from about 1.0 mg to about 25 mg, including, but not limited to, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, or about 25 mg.

In some embodiments, the pharmaceutical composition disclosed herein comprises naratriptan or a pharmaceutically acceptable salt thereof, that is present at a dose from about 0.5 mg to about 25 mg, including, but not limited to, about 0.5 mg to about 10 mg, about 0.5 mg to about 7.5 mg, about 0.5 mg to about 5.0 mg, about 0.5 mg to about 4.0 mg, about 0.5 mg to about 3.0 mg, about 3.0 mg to about 5.0 mg, about 5.0 mg to about 10.0 mg, about 10.0 mg to about 15 mg, about 15 mg to about 20 mg, about 20 mg to about 25 mg, about 1.0 mg to about 4.0 mg, about 4.0 mg to about 7.0 mg, or about 7.0 mg to about 10.0 mg. In some embodiments, the pharmaceutical composition described herein comprises naratriptan or a pharmaceutically acceptable salt thereof, that is present at a dose from about 1.0 mg to about 25 mg, including, but not limited to, about 0.5 mg, about 0.6 mg, about 0.7 mg, about 0.8 mg, about 0.9 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, or about 25 mg. In some embodiments, the pharmaceutically acceptable salt of naratriptan is naratriptan hydrochloride.

Antiemetics

In some embodiments, pharmaceutical compositions disclosed herein comprise one or more antiemetics. Exemplary antiemetics include, aprepitant, dronabinol, perphenazine, palonosetron, trimethyobenzamide, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypern-dyl, pipamazine, scopolamine, sulpiride, tetrahydrocannabinol, thiethylperazine, thioproperazine, tropisetron, droperidol, haloperidol, prochloperazine, metoclopramide, diphenhydramine, cannabinoid, midazolam, lorazepam, hyoscine, dexamethasone, emetrol, propofol, and pharmaceutically acceptable salts thereof. Antiemetics also include H1 agonists, H1 antagonists, H2 agonists, H2 antagonists, H3 agonists, H3 antagonists, H4 agonists, and H4 antagonists. Examples of such agonists and antagonists include, but are not limited to, 2-(m-fluoropheny)-histamine, azelastine, buclizine, carbinoxamine, cetrizine, clemastine, cyproheptadine, desloratidine, dimenhydrinate, diphenhydramine, emedastine, fexofenadine, hydroxyzine, ketotifen, levocabastine, olopatadine, phenindamine, promethazine, chlorpheniramine, scopolamine, mepyramine, terfenadine, astemizole, triprolidine, dimaprit, impromidine, amthamine, cimetidine, ranitidine, nizatidine, famotidine, R-alpha-methylhistamine, imetit, immepip, thioperamide, iodophenpropit, clobenpropit, clozapine, and a pharmaceutically acceptable salt thereof. In some embodiments, the second pharmaceutically active agent is an antiemetic. In some embodiments, the antiemetic is promethazine or a pharmaceutically acceptable salt thereof.

In some embodiments, the pharmaceutical composition disclosed herein comprises an antiemetic or a pharmaceutically acceptable salt thereof that is present at a dose from about 0.5 mg to about 100 mg, including but not limited to, from about 0.5 mg to about 12.5 mg, from about 12.5 mg to about 50 mg, from about 50 mg to about 75 mg, from about 75 mg to about 100 mg, from about 0.5 mg to about 15 mg, from about 15 mg to about 35 mg, from about 20 mg to about 30 mg, from about 35 mg to about 55 mg, from about 55 mg to about 75 mg, or from about 75 mg to about 95 mg. In some embodiments, the pharmaceutical composition described herein comprises an antiemetic that is present at a dose from about 0.5 mg to about 100 mg, including but not limited to, about 0.5 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the antiemetic is promethazine or a pharmaceutically acceptable salt thereof. In some embodiments, the antiemetic is provided at a dose to prevent or reduce sedation. In some embodiments, the pharmaceutical composition described herein comprises a pharmaceutically acceptable salt of an antiemetic in a quantity therapeutically equivalent to antiemetic dosages disclosed herein. In some embodiments, the pharmaceutical composition described herein comprises a pharmaceutically acceptable salt of promethazine in a quantity therapeutically equivalent to about 11 mg promethazine free base. In some embodiments, the pharmaceutical composition described herein comprises a pharmaceutically acceptable salt of promethazine in a quantity therapeutically equivalent to about 22 mg promethazine free base. In some embodiments, the pharmaceutical composition described herein comprises a pharmaceutically acceptable salt of promethazine in a quantity therapeutically equivalent to about 44 mg promethazine free base. In some embodiments, the pharmaceutical composition described herein comprises a pharmaceutically acceptable salt of promethazine in a quantity therapeutically equivalent to about 22.3 mg promethazine free base. In some embodiments, the pharmaceutical composition described herein comprises a pharmaceutically acceptable salt of promethazine in a quantity therapeutically equivalent to about 44.6 mg promethazine free base.

Pharmaceutically Acceptable Salts

In some embodiments, an agent used in a composition disclosed herein is the form of a free base, pharmaceutically acceptable salt, prodrug, analog or complex. In some instances, a pharmaceutically active agent comprises the form of a pharmaceutically acceptable salt. In various embodiments, with respect to a pharmaceutically active agent in a composition, a pharmaceutically acceptable salt includes, but is not limited to, metal salts, such as sodium salts, potassium salts, and lithium salts; alkaline earth metals, such as calcium salts, magnesium salts, and the like; organic amine salts, such as triethylamine salts, pyridine salts, picoline salts, ethanolamine salts, triethanolamine salts, dicyclohexylamine salts, N,N'-dibenzylethylenediamine salts, and the like; inorganic acid salts such as hydrochloride salts, hydrobromide salts, sulfate salts, phosphate salts, and the like; organic acid salts such as formate salts, acetate salts, trifluoroacetate salts, maleate salts, tartrate salts, and the like; sulfonate salts such as methanesulfonate salts, benzenesulfonate salts, p-toluenesulfonate salts, and the like; and amino acid salts, such as arginate salts, asparginate salts, glutamate salts, and the like.

In some embodiments, pharmaceutically acceptable salts include bitartrate, bitartrate hydrate, hydrochloride, p-toluenesulfonate, phosphate, sulfate, trifluoroacetate, bitartrate hemipentahydrate, pentafluoropropionate, hydrobromide, mucate, oleate, phosphate dibasic, phosphate monobasic, acetate trihydrate, bis(heptafluorobutyrate), bis(pentafluoropropionate), bis(pyridine carboxylate), bis(trifluoroacetate), chlorhydrate, and sulfate pentahydrate. In some embodiments, an agent is promethazine, a pharmaceutically acceptable salt or its thiosemicarbazone, p-nitrophenylhydrazone, o-methyloxime, semicarbazone, or bis(methylcarbamate). Other representative pharmaceutically acceptable salts include, e.g., water-soluble and water-insoluble salts, such as the acetate, amsonate(4,4-diaminostilbene-2,2-disulfonate), benzenesulfonate, benzonate, bicarbonate, bisulfate, bitartrate, borate, butyrate, calcium edetate, camphorsulfonate, camsylate, carbonate, citrate, clavulariate, dihydrochloride, edetate, edisylate, estolate, esylate, fiunarate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A hydrate is another example of a pharmaceutically acceptable salt. In some embodiments, the second pharmaceutically active agent is capable of reducing or eliminating an adverse effect of the first pharmaceutically active agent.

Pharmaceutically Acceptable Excipients

In some aspects, the pharmaceutical composition disclosed herein comprises one or more pharmaceutically acceptable excipients. Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. Examples of binders include microcrystalline cellulose, hydroxypropyl methylcellulose, carboxyvinyl polymer, polyvinylpyrrolidone, polyvinylpolypyrrolidone, carboxymethylcellulose calcium, carboxymethylcellulose sodium, ceratonia, chitosan, cottonseed oil, dextrates, dextrin, ethylcellulose, gelatin, glucose, glyceryl behenate, galactomannan polysaccharide, hydroxyethyl cellulose, hydroxyethylmethyl cellulose, hydroxypropyl cellulose, hypromellose, inulin, lactose, magnesium aluminum silicate, maltodextrin, methylcellulose, poloxamer, polycarbophil, polydextrose, polyethylene glycol, polyethylene oxide, polymethacrylates, sodium alginate, sorbitol, starch, sucrose, sunflower oil, vegetable oil, tocofersolan, zein, or combinations thereof. Examples of disintegrants include hydroxypropyl methylcellulose (HPMC), low substituted hydroxypropyl cellulose (L-HPC), croscarmellose sodium, sodium starch glycolate, lactose, magnesium aluminum silicate, methylcellulose, polacrilin potassium, sodium alginate, starch, or combinations thereof. Examples of a lubricant include stearic acid, sodium stearyl fumarate, glyceryl behenate, calcium stearate, glycerin monostearate, glyceryl palmitostearate, magnesium lauryl sulfate, mineral oil, palmitic acid, myristic acid, poloxamer, polyethylene glycol, sodium benzoate, sodium chloride, sodium lauryl sulfate, talc, zinc stearate, potassium benzoate, magnesium stearate or combinations thereof. Examples of diluents include talc, ammonium alginate, calcium carbonate, calcium lactate, calcium phosphate, calcium silicate, calcium sulfate, cellulose, cellulose acetate, corn starch, dextrates, dextrin, dextrose, erythritol, ethylcellulose, fructose, fumaric acid, glyceryl palmitostearate, isomalt, kaolin, lactitol, lactose, magnesium carbonate, magnesium oxide, maltodextrin, maltose, mannitol, microcrystalline cellulose, polydextrose, polymethacrylates, simethicone, sodium alginate, sodium chloride, sorbitol, starch, sucrose, sulfobutylether β-cyclodextrin, tragacanth, trehalose, xylitol, or combinations thereof. In some embodiments, the pharmaceutically acceptable excipient is hydroxypropyl methylcellulose (HPMC). In some embodiments, the pharmaceutically acceptable excipient is low substituted hydroxypropyl cellulose (L-HPC). In some embodiments, the pharmaceutically acceptable excipient is talc. In some embodiments, the pharmaceutically acceptable excipient is microcrystalline cellulose.

First Particulate

Disclosed herein is a first particulate comprising a $5HT_{1B/1D}$ receptor agonist. In some embodiments, each first particulate further comprises a non-pharmaceutically active ingredient. In some embodiments, the first particulates are beads, granules, spherules, or pellets (e.g., micropellets, or minipellets).

Size

In some embodiments, each first particulate are of different sizes. In some embodiments, each first particulate are of the same size. In some embodiments, target and maximum particulate size, including particulate size distribution, is determined through analytical sieving in accordance with USP <786> or other appropriately validated methods. Exemplary filters used in particulate size generation include, without limitation, #30, #40, #60, #100, and #140 size mesh screens, corresponding to 590 μm, 420 μm, 250 μm, 149 μm, and 105 μm in diameter, respectively. In some embodiments, the average diameter of each first particulate ranges from about 50 μm to about 1000 μm, including, but not limited to, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm, about 610 μm, about 620 μm, about 630 μm, about 640 μm, about 650 μm, about 660 μm, about 670 μm, about 680 μm, about 690 μm, about 700 μm, about 710 μm, about 720 μm, about 730 μm, about 740 μm, about 750 μm, about 760 μm, about 770 μm, about 780 μm, about 790 μm, about 800 μm, about 810 μm, about 820 μm, about 830 μm, about 840 μm, about 850 μm, about 860 μm, about 870 μm, about 880 μm, about 890 μm, about 900 μm, about 910 μm, about 920 μm, about 930 μm, about 940 μm, about 950 μm, about 960 μm, about 970 μm, about 980 μm, about 990 μm, or about 1000 μm. In some embodiments, the average diameter of each first particulate is less than about 500 μm. In some embodiments, the average diameter of the each particulate range from 100 μm to about 500 μm, including, but not limited to, from about 100 μm to about 200 μm, from about 100 μm to about 300 μm, from about 100 μm to about 400 μm, from about 200 μm to about 300 μm, from about 200 μm to about 400 μm, from about 200 μm to about 500 μm, from about 300 μm to about 500 μm, or from about 400 μm to about 500 μm.

Composition

Core

In some embodiments, each first particulate comprises a $5HT_{1B/1D}$ receptor agonist. In some embodiments, the $5HT_{1B/1D}$ receptor agonist is sumatriptan or a pharmaceutically acceptable salt thereof. In some embodiments, each first particulate comprises at least about 50% of a $5HT_{1B/1D}$ receptor agonist (w/w). In some embodiments, the amount of the $5HT_{1B/1D}$ receptor agonist in the first particulate range from about 50% to about 90% (w/w), including but not limited to, from about 50% to about 80% (w/w), from about 50% to about 70% (w/w), from about 50% to about 60% (w/w), from about 60% to about 90% (w/w), from about 70% to about 90% (w/w), from about 80% to about 90% (w/w), from about 55% to about 65% (w/w), from about 55% to about 75% (w/w), or from about 55% to about 85% (w/w). In some embodiments, the amount of the $5HT_{1B/1D}$ receptor agonist in the first particulate range from about 50% to about 90% (w/w), including, but not limited to, about 50% (w/w), about 55% (w/w), about 60% (w/w), about 65% (w/w), about 70% (w/w), about 75% (w/w), about 80% (w/w), about 85% (w/w), or about 90% (w/w).

In some embodiments, each first particulate comprises a non-pharmaceutically active ingredient. In some embodiments, the non-pharmaceutically active ingredient is selected from the group consisting of microcrystalline cellulose, dicalcium phosphate, calcium sulfate, talc, an alkali metal stearate, silicon dioxide, calcium carbonate, and any combinations thereof. In some embodiments, the non-pharmaceutically active ingredient is microcrystalline cellulose. In some embodiments, each first particulate comprises at most about 50% of a non-pharmaceutically active ingredient (w/w). In some embodiments, the amount of the non-pharmaceutically active ingredient in the first particulate range from about 10% to about 50% (w/w), including but not limited to, from about 10% to about 40% (w/w), from about 10% to about 30% (w/w), from about 10% to about 20% (w/w), from about 20% to about 50% (w/w), from about 30% to about 50% (w/w), or from about 40% to about 50% (w/w). In some embodiments, the amount of the non-pharmaceutically active ingredient in each first particulate range from about 10% to about 50% (w/w), including, but not limited to, about 10% (w/w), about 15% (w/w), about 20% (w/w), about 25% (w/w), about 30% (w/w), about 35% (w/w), about 40% (w/w), about 45% (w/w), or about 50% (w/w).

Coating

In some cases, the first particulate disclosed herein is coated with a coating material, e.g., a sealant. In some embodiments, the coating material is water soluble. In some embodiments, the coating material comprises a polymer, plasticizer, a pigment, or any combination thereof. In some embodiments, the coating material is a form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of drug actives. In some embodiments, the coating material is pigmented, clear, or white. In some embodiments, the coating material is clear. Exemplary coating materials include, without limitation, polyvinyl alcohol (PVA), cellulose acetate phthalate (CAP), polyvinyl acetate phthalate (PVAP), methacrylic acid copolymers, cellulose acetate trimellitate (CAT), hydroxypropyl methylcellulose phthalate (HPMCP), hydroxypropyl methylcellulose (HPMC), hydroxy propyl methyl cellulose acetate succinate (hypromellose acetate succinate), shellac, sodium alginate, and zein. In some embodiments, the coating material comprises or is PVA. In some embodiments, the coating material comprises or is HPMC. An exemplary PVA-based coating material includes Opadry II. In some instances, the coating material is about 1, 2, 3, 4, 5, 6, 7, 8, 9, or 10% of the weight of each first particulate. In some instances, the coating material represent between about 1% and about 15% of the total weight of each first particulate, including, but not limited to, between about 5% and about 10%, between about 6% and about 10%, between about 7% and about 10%, between about 8% and about 10%, or between about 9% and about 10%. In some instances, the coating material is greater than about 2%, greater than about 3%, greater than about 4%, greater than about 5%, greater than about 6%, greater than about 7%, greater than about 8%, greater than about 9%, or greater than about 10% of the weight of each first particulate. In some instances, the coating material is less than about 2%, less than about 3%, less than about 4%, less than about 5%, less than about 6%, less than about 7%, less than about 8%, less than about 9%, or less than about 10% of the weight of each first particulate.

Dissolution

An example of a method to measure dissolution profiles is provided at Examples 4 and 5. In some aspects, dissolution rates are measured by a USP Apparatus 2 (Paddle Apparatus) at a speed of 50 rpm in a dissolution fluid of 500 ml de-aerated 0.1 N HCl (i.e., pH 1.1) at 37.0±0.5° C. In some instances, dissolution samples are analyzed by HPLC. In some embodiments, at least about 80% of the $5HT_{1B/1D}$ receptor agonist is released within about 5 minutes following contact of the particulate with 500 mL of a dissolution fluid (0.1N HCl, pH 1.1) at 37+/−0.5° C. as measured by an Apparatus 2 (Paddles) rotating at 50 rpm. In some embodiments, at least about 81% of the $5HT_{1B/1D}$ receptor agonist is released within about 5 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 89% of the $5HT_{1B/1D}$ receptor agonist is released within about 10 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 15 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the $5HT_{1B/1D}$ receptor agonist is released within about 20 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm.

Second Particulate

Disclosed herein is a second particulate comprising a core and a layer enclosing the core, wherein the layer comprises an antiemetic. In some embodiments, the second particulates are beads, granules, spherules, or pellets (e.g., micropellets, or minipellets). In some embodiments, the second particulates comprise a coating.

Size

In some embodiments, each second particulate is of different sizes. In some embodiments, each second particulate is of the same size. In some embodiments, target and maximum particulate size, including particulate size distribution, is determined through analytical sieving in accordance with USP <786> or other appropriately validated methods. Exemplary filters used in particulate size generation include, without limitation, #16, #18, #20, and #25 size mesh screens, corresponding to 1190 µm, 1000 µm, 840 µm, and 710 µm in diameter, respectively. In some embodiments, the average diameter of each second particulate range from about 500 µm to about 1500 µm, including, but not limited to, about 500 µm, about 510 µm, about 520 µm, about 530 µm, about 540 µm, about 550 µm, about 560 µm, about 570 µm, about 580 µm, about 590 µm, about 600 µm, about 610 µm, about 620 µm, about 630 µm, about 640 µm, about 650 µm, about 660 µm, about 670 µm, about 680 µm, about 690 µm, about 700 µm, about 710 µm, about 720 µm, about 730 µm, about 740 µm, about 750 µm, about 760 µm, about 770 µm, about 780 µm, about 790 µm, about 800 µm, about 810 µm, about 820 µm, about 830 µm, about 840 µm, about 850 µm, about 860 µm, about 870 µm, about 880 µm, about 890 µm, about 900 µm, about 910 µm, about 920 µm, about 930 µm, about 940 µm, about 950 µm, about 960 µm, about 970 µm, about 980 µm, about 990 µm, about 1000 µm, about 1010 µm, about 1020 µm, about 1030 µm, about 1040 µm, about 1050 µm, about 1060 µm, about 1070 µm, about 1080 µm, about 1090 µm, about 1100 µm, about 1110 µm, about 1120 µm, about 1130 µm, about 1140 µm, about 1150 µm, about 1160 µm, about 1170 µm, about 1180 µm, about 1190 µm, about 1200 µm, about 1210 µm, about 1220 µm, about 1230 µm, about 1240 µm, about 1250 µm, about 1260 µm, about 1270 µm, about 1280 µm, about 1290 µm, about 1300 µm, about 1310 µm, about 1320 µm, about 1330 µm, about 1340 µm, about 1350 µm, about 1360 µm, about 1370 µm, about 1380 µm, about 1390 µm, about 1400 µm, about 1410 µm, about 1420 µm, about 1430 µm, about 1440 µm, about 1450 µm, about 1460 µm, about 1470 µm, about 1480 µm, about 1490 µm, or about 1500 µm. In some embodiments, the average diameter of each second particulate range from 700 µm to about 1200 µm, including, but not limited to, from about 700 µm to about 1100 µm, from about 700 µm to about 1000 µm, from about 700 µm to about 900 µm, from about 700 µm to about 800 µm, from about 800 m to about 1200 µm, from about 900 µm to about 1200 µm, from about 1000 µm to about 1200 µm, or from about 1100 µm to about 1200 µm.

Composition

Core

In some embodiments, each second particulate comprises a core. In some embodiments, the core is an inert core such as a sugar sphere (non-pareils) or a microcrystalline cellulose sphere. In some embodiments, the inert core is a sugar sphere (such as Suglets™ or SureSpheres™). In some embodiments, the sugar sphere comprises sucrose or a mixture of sucrose and starch. In some embodiments, the sugar sphere comprises multiple layers. In some embodiments, the sugar sphere comprises a sucrose core, a sucrose layer and a corn starch layer. In some embodiments, the sugar sphere diameter is between about 212 µm and about 850 µm. In some embodiments, the sugar sphere diameter is between about 250 µm and about 355 µm, between about 355 µm and about 500 µm, between about 425 µm and about 500 µm, between about 500 µm and about 600 µm, between about 610 µm and about 710 µm, between about 710 µm and about 850 µm, between about 850 µm and about 1000 µm, between about 850 µm and about 1180 µm, or between about 1000 µm and about 1400 µm. In some embodiments, the inert core is a microcrystalline cellulose sphere (such as Cellets™ or Celpherer™). In some embodiments, the microcrystalline cellulose sphere diameter is between about 106 µm and about 212 µm, between about 150 µm and about 300 µm, between about 300 µm and about 500 µm, between about 500 µm and about 710 µm, or between about 710 µm and about 850 µm.

In some embodiments, the core represents between about 40% and about 90% of the total weight of the second particulate (w/w), e.g., between about 40% and about 80% (w/w), between about 40% and about 70% (w/w), between about 50% and about 70% (w/w), between about 40% and about 60% (w/w), between about 40% and about 50% (w/w), between about 50% and about 90% (w/w), between about 50% and about 60% (w/w), between about 60% and about 90% (w/w), between about 70% and about 90% (w/w), or between about 70% and about 80% (w/w). In some embodiments, the core represents between about 40% and about 90% of the total weight of the second particulate (w/w), e.g., about 40% (w/w), about 45% (w/w), about 50% (w/w), about 55% (w/w), about 60% (w/w), about 65% (w/w), about 70% (w/w), about 75% (w/w), about 80% (w/w), about 85% (w/w), or about 90% (w/w).

Layer Enclosing the Core

In some embodiments, each second particulate comprises an active ingredient layer enclosing the core. In some embodiments, the active ingredient layer enclosing the core is directly adjacent to the core. In some embodiments, the active ingredient layer comprises multiple active ingredients. In some embodiments, the active ingredient layer comprises an antiemetic as disclosed herein. In some embodiments, the active ingredient layer comprises promethazine or a pharmaceutically acceptable salt thereof. In some embodiments, the active ingredient layer further comprises pharmaceutically acceptable excipients. In some embodiments, the active ingredient layer is applied onto the inert core by methods known in the art. In some embodiments, the active ingredient layer is applied by solution or suspension layering. In some embodiments, the active ingredient and pharmaceutically acceptable excipients are dissolved or suspended in water or an organic solvent. In some embodiments, the pharmaceutically acceptable excipients comprise disintegrants, lubricants, binders, diluents and the like. In some embodiments, the pharmaceutically acceptable excipients comprise hydroxypropyl methylcellulose (HPMC), low substituted hydroxypropyl cellulose (L-HPC), talc, and any combinations thereof.

In some embodiments, each second particulate comprises an antiemetic. In some embodiments, the antiemetic is promethazine or a pharmaceutically acceptable salt thereof. In some embodiments, the amount of the antiemetic in the second particulates range from about 5% to about 40% (w/w), including but not limited to, from about 5% to about 30% (w/w), from about 5% to about 25% (w/w), from about 10% to about 40% (w/w), from about 10% to about 30% (w/w), from about 20% to about 40% (w/w), from about 20% to about 30% (w/w), or from about 20% to about 25% (w/w). In some embodiments, the amount of the antiemetic in the second particulates range from about 5% to about 40% (w/w), including, but not limited to, about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21%

(w/w), about 22% (w/w), about 23% (w/w), about 24% (w/w), about 25% (w/w), about 26% (w/w), about 27% (w/w), about 28% (w/w), about 29% (w/w), about 30% (w/w), about 31% (w/w), about 32% (w/w), about 33% (w/w), about 34% (w/w), about 35% (w/w), about 36% (w/w), about 37% (w/w), about 38% (w/w), about 39% (w/w), or about 40% (w/w).

In some embodiments, the amount of the antiemetic in the drug layer range from about 50% to about 90% (w/w), including but not limited to, from about 50% to about 80% (w/w), from about 60% to about 80% (w/w), from about 50% to about 70% (w/w), from about 65% to about 75% (w/w), or from about 55% to about 85% (w/w).

In some embodiments, each second particulate comprises pharmaceutically acceptable excipients. In some embodiments, the pharmaceutically acceptable excipients represents between about 2% and about 15% of the total weight of the second particulates, including, but not limited to, between about 5% and about 15% (w/w), between about 5% and about 10% (w/w), or between about 5% and about 9% (w/w). In some embodiments, the amount of pharmaceutically acceptable excipients in the drug layer of the second particulates range from about 10% to about 50% (w/w), including but not limited to, from about 10% to about 40% (w/w), from about 20% to about 40% (w/w), from about 25% to about 35% (w/w), or from about 15% to about 45% (w/w).

In some embodiments, the pharmaceutically acceptable excipients comprised in each second particulate comprise hydroxypropyl methylcellulose (HPMC), low substituted hydroxypropyl cellulose (L-HPC), talc, and any combinations thereof.

In some embodiments, one of the pharmaceutically acceptable excipient comprised in each second particulate is hydroxypropyl methylcellulose (HPMC). In some embodiments, hydroxypropyl methylcellulose represents between about 2% and about 10% of the total weight of the second particulate, including, but not limited to, between about 5% and about 10% (w/w), between about 5% and about 9% (w/w), between about 5% and about 8% (w/w), or between about 5% and about 7% (w/w). In some embodiments, the amount of hydroxypropyl methylcellulose in the drug layer of the second particulates range from about 10% to about 30% (w/w), including but not limited to, from about 10% to about 25% (w/w), from about 10% to about 20% (w/w), from about 15% to about 25% (w/w), or from about 15% to about 20% (w/w).

In some embodiments, one of the pharmaceutically acceptable excipient comprised in the second particulates is talc. In some embodiments, talc represents between about 0.5% and about 3% of the total weight of the second particulate, including, but not limited to, between about 0.5% and about 2.5% (w/w), between about 0.5% and about 2% (w/w), between about 0.5% and about 1.5% (w/w), or between about 1% and about 1.5% (w/w). In some embodiments, the amount of talc in the drug layer of the second particulate range from about 1% to about 5% (w/w), including but not limited to, from about 1% to about 4% (w/w), from about 2% to about 4% (w/w), from about 2% to about 3.5% (w/w), or from about 2.5% to about 3.5% (w/w).

In some embodiments, one of the pharmaceutically acceptable excipient comprised in the second particulates is low substituted hydroxypropyl cellulose (L-HPC). In some embodiments, L-HPC represents between about 1% and about 5% of the total weight of the second particulates, including, but not limited to, between about 1% and about 4% (w/w), between about 1% and about 3% (w/w), between about 2% and about 3% (w/w), or between about 1.5% and about 2.5% (w/w). In some embodiments, the amount of L-HPC in the drug layer of the second particulates range from about 4% to about 10% (w/w), including but not limited to, from about 5% to about 9% (w/w), from about 6% to about 8% (w/w), from about 4% to about 8% (w/w), or from about 6% to about 9% (w/w).

Coating

In some cases, the second particulates disclosed herein are coated with a coating material, e.g., a sealant. In some embodiments, the coating material is water soluble. In some embodiments, the coating material comprises a polymer, plasticizer, a pigment, or any combination thereof. In some embodiments, the coating material is a form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of drug actives. In some embodiments, the coating material is pigmented, clear, or white. In some embodiments, the coating material is clear. Exemplary coating materials include, without limitation, polyvinyl alcohol (PVA), cellulose acetate phthalate (CAP), polyvinyl acetate phthalate (PVAP), methacrylic acid copolymers, cellulose acetate trimellitate (CAT), hydroxypropyl methylcellulose phthalate (HPMCP), hydroxypropyl methylcellulose (HPMC), hydroxy propyl methyl cellulose acetate succinate (hypromellose acetate succinate), shellac, sodium alginate, and zein. In some embodiments, the coating material comprises or is PVA. In some embodiments, the coating material comprises or is HPMC. An exemplary PVA-based coating material includes Opadry II. In some instances, the coating material is about 1, 2, 3, 4, 5, 6, 7, 8, 9, or 10% of the weight of the second particulates. In some instances, the coating material represent between about 1% and about 15% of the total weight of the second particulates, including, but not limited to, between about 5% and about 10%, between about 6% and about 10%, between about 7% and about 10%, between about 8% and about 10%, or between about 9% and about 10%. In some instances, the coating material is greater than about 2%, greater than about 3%, greater than about 4%, greater than about 5%, greater than about 6%, greater than about 7%, greater than about 8%, greater than about 9%, or greater than about 10% of the weight of the second particulates. In some instances, the coating material is less than about 2%, less than about 3%, less than about 4%, less than about 5%, less than about 6%, less than about 7%, less than about 8%, less than about 9%, or less than about 10% of the weight of the second particulates.

Dissolution

An example of a method to measure dissolution profiles is provided at Examples 4 and 5. In some aspects, dissolution rates are measured by a USP Apparatus 2 (Paddle Apparatus) at a speed of 50 rpm in a dissolution fluid of 500 ml de-aerated 0.1 N HCl (i.e., pH 1.1) at 37.0±0.5° C. In some instances, dissolution samples are analyzed by HPLC.

In some embodiments, at least about 95% of the antiemetic is released within about 5 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm. In some embodiments, at least about 100% of the antiemetic is released within about 15 minutes following contact of the first particulate with 500 mL of a dissolution fluid (0.1N HCl, pH 1.1) at 37+/−0.5° C. as measured by an Apparatus 2 (Paddle Apparatus) rotating at 50 rpm.

Provided herein are particulates, compositions, and capsules comprising an antiemetic, wherein the antiemetic is in a rapid release matrix. In some embodiments, the antiemetic is promethazine or a pharmaceutically acceptable salt thereof. In some embodiments, the promethazine is promethazine hydrocholoride. In some embodiments, the promethazine is present in an amount of from about 12.5 mg to about 60 mg. In some embodiments, the promethazine hydrochloride is present in an amount of from about 12.5 mg to about 60 mg. In some embodiments, the promethazine hydrochloride is present in an amount of 25 mg or 50 mg. In some embodiments, the promethazine base is present in an amount of 22 mg or 44 mg. In some embodiments, a capsule comprises from about 50 mg to about 150 mg of sumatriptan or a pharmaceutically acceptable salt thereof and from about 12.5 to about 60 mg of promethazine or a pharmaceutically acceptable salt thereof. In some embodiments, the capsule comprises from about 50 mg to about 150 mg of sumatriptan succinate and from about 12.5 to about 60 mg of promethazine hydrochloride. In some embodiments, the capsule comprises about 126 mg of sumatriptan succinate and about 50 mg of promethazine hydrochloride.

Capsules

Figure 2:
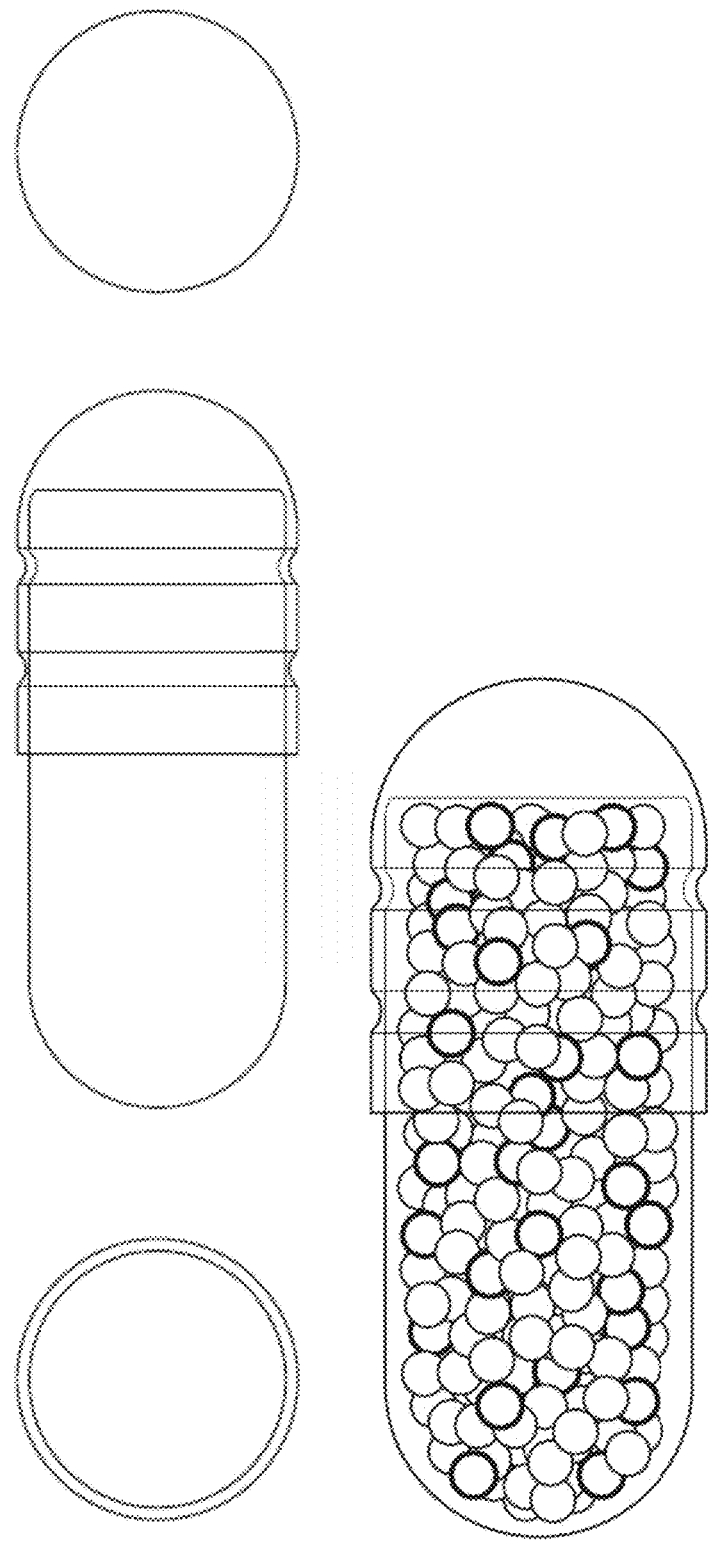
FIG. 2 illustrates another exemplary capsule, unfilled (left, in top, side and bottom view) or filled (right) with particulates. Particulates are not drawn to scale.
Figure 3:
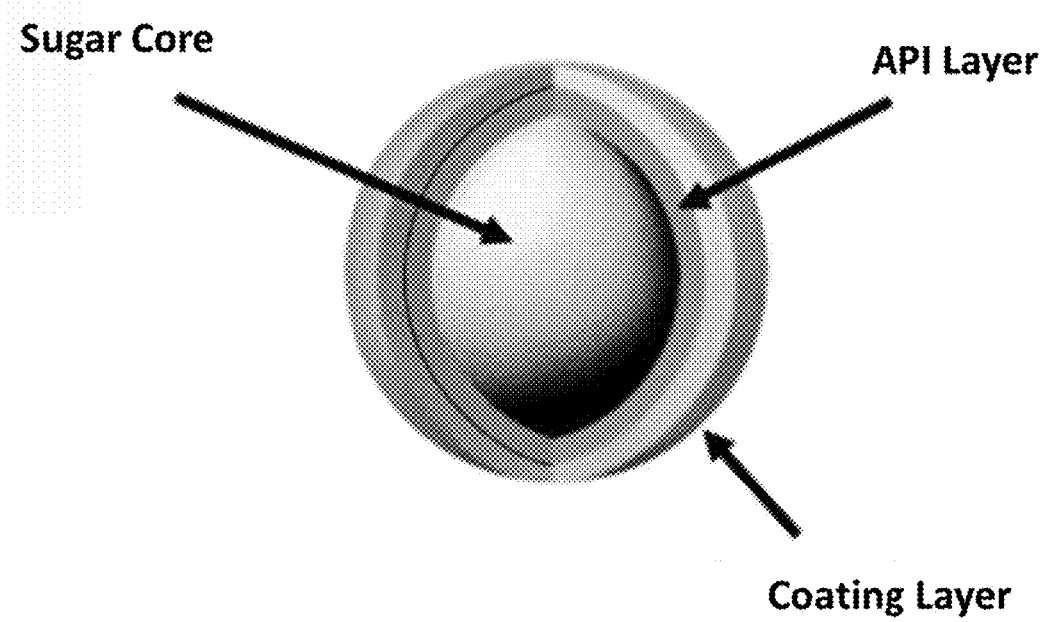
FIG. 3 illustrates an exemplary particulate comprising an inner sugar core, a layer comprising an active pharmaceutical ingredient ("API"), and an optional coating layer.

In some aspects, the pharmaceutical composition disclosed herein is encapsulated into discrete units. In some embodiments, the discrete units are capsules or packets. In some embodiments, the pharmaceutical composition disclosed herein is enclosed in a capsule. In embodiments, the pharmaceutical composition disclosed herein comprises pluralities of particulates. In some embodiments, the pharmaceutical composition comprises a plurality of first particulates and a plurality of second particulates. In some embodiments, the plurality of first particulates comprises a $5HT_{1B/1D}$ receptor agonist. In some embodiments, the plurality of first particulates comprises a triptan or a pharmaceutically acceptable salt thereof. In some embodiments, the plurality of first particulates comprises sumatriptan or a pharmaceutically acceptable salt thereof. In some embodiments, the plurality of first particulates comprises sumatriptan succinate. In some embodiments, the plurality of second particulates comprises an antiemetic. In some embodiments, the plurality of second particulates comprises promethazine or a pharmaceutically acceptable salt thereof. In some embodiments, the plurality of second particulates comprises promethazine hydrochloride. FIGS. 1 and 2 illustrate exemplary capsules containing two types of beads, one bead comprising an antiemetic described herein and the other bead comprising a $5HT_{1B/1D}$ receptor agonist described herein. In some embodiments, the pharmaceutical composition disclosed herein comprises a plurality of third particulates. In some embodiments the plurality of third particulates comprises an antiemetic different than that present in the plurality of second particulates.

Amounts and weight ratios disclosed herein for the first particulates and the second particulates provide an advantageous feature for the treatment of a headache (e.g., a migraine or cluster headache). Amounts and weight ratios disclosed herein for the first particulates and the second particulates also provide an advantageous feature for the treatment of nausea associated with a migraine and/or vomiting associated with a migraine. In some embodiments, the capsule is formed using materials which include, but are not limited to, natural or synthetic gelatin, pectin, casein, collagen, protein, modified starch, polyvinylpyrrolidone, acrylic polymers, cellulose derivatives, or combinations thereof. In some embodiments, the capsule is formed using preservatives, coloring and opacifying agents, flavorings and sweeteners, sugars, gastroresistant substances, or combinations thereof. In some embodiments, the capsule is coated. In some embodiments, the coating covering the capsule includes, but is not limited to, immediate release coatings, protective coatings, enteric or delayed release coatings, sustained release coatings, barrier coatings, seal coatings, or combinations thereof. In some embodiments, a capsule herein is hard or soft. In some embodiments, the capsule is seamless. In some embodiments, the capsule is broken such that the particulates are sprinkled on soft foods and swallowed without chewing. In some embodiments, the shape and size of the capsule also vary. Examples of capsule shapes include, but are not limited to, round, oval, tubular, oblong, twist off, or a non-standard shape. The size of the capsule may vary according to the volume of the particulates. In some embodiments, the size of the capsule is adjusted based on the volume of the particulates and powders. Hard or soft gelatin capsules may be manufactured in accordance with conventional methods as a single body unit comprising the standard capsule shape. A single-body soft gelatin capsule typically may be provided, for example, in sizes from 3 to 22 minims (1 minims being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. In some embodiments, the pharmaceutical composition disclosed herein (e.g., capsule) is swallowed as a whole. In some embodiments, the pharmaceutical composition disclosed herein (e.g., capsule) does not completely disintegrate in mouth within about: 2, 3, 4, 5, 6, 7, 8, 9, 10, 11, 12, 13, 14, 15, 16, 17, 18, 19, or 20 minutes. In some embodiments, the pharmaceutical composition disclosed herein is not a film. In some embodiments, the pharmaceutical composition disclosed herein is not for buccal administration. In some embodiments, the pharmaceutical composition disclosed herein (e.g., capsule) dissolves in stomach or intestine.

In some embodiments, a capsule disclosed herein has a net weight of ranging from 28 mg to 125 mg, e.g., from about 90 mg to about 102 mg, about 100 mg to about 114 mg, about 103 mg to about 117 mg, about 76 mg to about 86 mg, about 71 mg to about 81 mg, about 61 mg to about 71 mg, about 57 mg to about 65 mg, about 45 mg to about 51 mg, about 37 mg to about 43 mg, about 35 mg to about 41 mg, or about 26 mg to about 30 mg. In some cases, the capsule has a net weight of about 118 mg, about 107 mg, about 110 mg, about 95 mg, about 81 mg, about 75 mg, about 66 mg, about 60 mg, about 47 mg, about 40 mg, about 38 mg, or about 28 mg. In some cases, a capsule has a volume ranging from about 0.1 to 0.9 ml, e.g., about 0.6 ml to about 0.8 ml, about 0.4 ml to about 0.6 ml, about 0.3 ml to about 0.5 ml, about 0.2 ml to about 0.4 ml, or about 0.1 ml to about 0.3 ml. In some cases, the capsule has a volume of about 0.9 ml, about 0.8 ml, about 0.7 ml, about 0.6 ml, about 0.5 ml, about 0.4 ml, about 0.35 ml, about 0.3 ml, about 0.25 ml, about 0.2 ml, about 0.15 ml, or about 0.1 ml. In some cases, a body of the capsule ranges from about 9 mm to about 20 mm long, e.g., about 17 mm to about 20 mm long, about 17 mm to about 19 mm long, about 16 mm to about 20 mm long, about 15 mm to about 19 mm long, about 14 mm to about 18 mm long, about 13 mm to about 17 mm long, about 12 mm to about 16 mm long, about 11 mm to about 15 mm long, about 10 mm to about 14 mm long, about 9 mm to about 13 mm long, about 9 mm to about 12 mm long, about 9 mm to about 11 mm long, or about 9 mm to about 10 mm long. In some cases, the body of the capsule is about 18 mm long, about 17 mm long, about 16 mm long, about 15 mm long, about 14 mm long, about 13 mm long, about 12 mm long, about 11 mm long, about 10 mm long, or about 9 mm long. In some cases, a cap of the capsule ranges from about 6 mm to about 12 mm long, e.g., about 10 mm to 12 mm long, about 9 mm to about 11 mm long, about 8 mm to about 10 mm long, about 7 mm to about 9 mm long, or about 6 mm to about 8 mm long. In some cases, the cap of the capsule is about 11 mm long, about 10 mm long, about 9 mm long, about 8 mm long, about 7 mm long, or about 6 mm long. In some cases, the body of the capsule has an external diameter ranging from about 4 mm to about 9 mm, e.g., about 6 mm to about 8 mm, about 7 mm to about 9 mm, about 7 mm to about 8 mm, about 5 mm to about 7 mm, or about 4 mm to about 6 mm. In some cases, the body of the capsule has an external diameter of about 9 mm, about 8 mm, about 7 mm, about 6 mm, about 5 mm, or about 4 mm. In some cases, a cap of the capsule has an external diameter ranging from about 4 mm to about 9 mm, e.g., about 7 mm to about 9 mm, about 6 mm to about 9 mm, about 7 mm to about 8 mm, about 5 mm to about 7 mm, or about 4 mm to about 6 mm. In some cases, the cap of the capsule has an external diameter of about 9 mm, about 8 mm, about 7 mm, about 6 mm, about 5 mm, or about 4 mm. In some cases, an overall closed length of the capsule ranges from about 10 mm to about 24 mm, e.g., about 20 mm to about 24 mm, or about 21 mm to about 23 mm, about 20 mm to about 22 mm, about 19 mm to about 21 mm, about 18 mm to about 20 mm, about 17 mm to about 19 mm, about 16 mm to about 18 mm, about 15 mm to about 17 mm, about 14 mm to about 16 mm, about 13 mm to about 15 mm, about 12 mm to about 14 mm, about 11 mm to about 13 mm, or about 10 mm to about 12 mm. In some cases, the overall closed length of the capsule is about 22 mm, about 24 mm, about 23 mm, about 21 mm, about 20 mm, about 19 mm, about 18 mm, about 17 mm, about 16 mm, about 15 mm, about 14 mm, about 13 mm, about 12 mm, about 11 mm, or about 10 mm. In some cases, the capsule has a capacity of about 50 mg to about 800 mg, e.g., about 400 mg to about 800 mg, about 350 mg to about 450 mg, about 300 mg to about 500 mg, about 300 mg to about 400 mg, about 250 mg to about 350 mg, about 200 mg to about 300 mg, about 200 mg to about 250 mg, about 150 mg to about 200 mg, about 100 mg to about 200 mg, about 100 mg to about 150 mg, about 50 mg to about 100 mg, about 600 g, about 500 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, or about 75 mg, and a powder density of about 0.6 g/ml to about 1.2 g/ml, e.g., about 0.6 g/ml, g/ml 0.8 g/ml, g/ml 1 g/ml, or g/ml 1.2 g/ml. In some cases, the capsule is oblong.

Dosages in Capsule

In some aspects, the pharmaceutical composition disclosed herein comprises multiple pharmaceutically active agents at the same or different dosages. In some embodiments, the pharmaceutical composition disclosed herein comprises a $5HT_{1B/1D}$ receptor agonist disclosed herein and an antiemetic disclosed herein. In some embodiments, a pharmaceutically active agent such as $5HT_{1B/1D}$ receptor agonist varies in dosages as further described herein, and the dosage of a pharmaceutically active agent such as an antiemetic is adjusted according to the particular $5HT_{1B/1D}$ receptor agonist used.

In some embodiments, the pharmaceutical composition described herein comprises sumatriptan or a pharmaceutically acceptable salt thereof and promethazine or a pharmaceutically acceptable salt thereof. In some embodiments, the sumatriptan or a pharmaceutically acceptable salt thereof is present at a dose from about 10 mg to about 200 mg, including, but not limited to, about 10.0 mg, about 10.5 mg, about 11.0 mg, about 11.5 mg, about 12.0 mg, about 12.5 mg, about 13.0 mg, about 13.5 mg, about 14.0 mg, about 14.5 mg, about 15.0 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, about 50 mg, about 55 mg, about 60 mg, about 65 mg, about 70 mg, about 75 mg, about 80 mg, about 85 mg, about 90 mg, about 95 mg, about 100, about 105 mg, about 110 mg, about 115 mg, about 120 mg, about 120.5 mg, about 121 mg, about 121.5 mg, about 122 mg, about 122.5 mg, about 123 mg, about 123.5 mg, about 124 mg, about 124.5 mg, about 125 mg, about 125.5 mg, about 126 mg, about 126.5 mg, about 127 mg, about 127.5 mg, about 128 mg, about 128.5 mg, about 129 mg, about 129.5 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 25 mg to about 100 mg, about 35 mg to about 140 mg, about 70 mg to about 140 mg, about 80 mg to about 135 mg, about 10 mg to about 25 mg, about 25 mg to about 50 mg, about 50 mg to about 100 mg, about 100 mg to about 150 mg, about 150 mg to about 200 mg, about 10 mg to about 35 mg, about 35 mg to about 70 mg, about 70 mg to about 105 mg, about 105 mg to about 140 mg, about 140 mg to about 175 mg, or about 175 mg to about 200 mg and the promethazine or a pharmaceutically acceptable salt thereof is present at a dose from about 0.5 mg to about 100 mg, including, but not limited to, about 0.5 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 12 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 0.5 mg to about 12.5 mg, about 12.5 mg to about 50 mg, about 50 mg to about 75 mg, about 75 mg to about 100 mg, about 0.5 mg to about 15 mg, about 15 mg to about 35 mg, about 35 mg to about 55 mg, about 55 mg to about 75 mg, or about 75 mg to about 95 mg.

In some embodiments, the pharmaceutical composition disclosed herein comprises sumatriptan succinate and promethazine hydrochloride. In some embodiments, the sumatriptan succinate is present at a dose from about 10 mg to about 200 mg, including, but not limited to, about 10.0 mg, about 10.5 mg, about 11.0 mg, about 11.5 mg, about 12.0 mg, about 12.5 mg, about 13.0 mg, about 13.5 mg, about 14.0 mg, about 14.5 mg, about 15.0 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 30.5 mg, about 31 mg, about 31.5 mg, about 32 mg, about 32.5 mg, about 33 mg, about 33.5 mg, about 34 mg, about 34.5 mg, about 35 mg, about 35.5 mg, about 36 mg, about 36.5 mg, about 37 mg, about 37.5 mg, about 38 mg, about 38.5 mg, about 39 mg, about 39.5 mg, about 40 mg, about 40.5 mg, about 41 mg, about 41.5 mg, about 42 mg, about 42.5 mg, about 43 mg, about 43.5 mg, about 44 mg, about 44.5 mg, about 45 mg, about 45.5 mg, about 46 mg, about 46.5 mg, about 47 mg, about 47.5 mg, about 48 mg, about 48.5 mg, about 49 mg, about 49.5 mg, about 50 mg, about 55 mg, about 60 mg, about 65 mg, about 70 mg, about 75 mg, about 80 mg, about 85 mg, about 90 mg, about 95 mg, about 100, about 105 mg, about 110 mg, about 115 mg, about 120 mg, about 120.5 mg, about 121 mg, about 121.5 mg, about 122 mg, about 122.5 mg, about 123 mg, about 123.5 mg, about 124 mg, about 124.5 mg, about 125 mg, about 125.5 mg, about 126 mg, about 126.5 mg, about 127 mg, about 127.5 mg, about 128 mg, about 128.5 mg, about 129 mg, about 129.5 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 25 mg to about 100 mg, about 35 mg to about 140 mg, about 70 mg to about 140 mg, about 80 mg to about 135 mg, about 10 mg to about 25 mg, about 25 mg to about 50 mg, about 50 mg to about 100 mg, about 100 mg to about 150 mg, about 150 mg to about 200 mg, about 10 mg to about 35 mg, about 35 mg to about 70 mg, about 70 mg to about 105 mg, about 105 mg to about 140 mg, about 140 mg to about 175 mg, or about 175 mg to about 200 mg and the promethazine hydrochloride is present at a dose from about 0.5 mg to about 100 mg, including, but not limited to, from about 0.5 mg to about 100 mg, including but not limited to, about 0.5 mg, about 1.0 mg, about 1.5 mg, about 2.0 mg, about 2.5 mg, about 3.0 mg, about 3.5 mg, about 4.0 mg, about 4.5 mg, about 5.0 mg, about 5.5 mg, about 6.0 mg, about 6.5 mg, about 7.0 mg, about 7.5 mg, about 8.0 mg, about 8.5 mg, about 9.0 mg, about 9.5 mg, about 10.0 mg, about 10.5 mg, about 11.0 mg, about 11.5 mg, about 12.0 mg, about 12.5 mg, about 13 mg, about 13.5 mg, about 14 mg, about 14.5 mg, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 20.5 mg, about 21 mg, about 21.5 mg, about 22 mg, about 22.5 mg, about 23 mg, about 23.5 mg, about 24 mg, about 24.5 mg, about 25 mg, about 25.5 mg, about 26 mg, about 26.5 mg, about 27 mg, about 27.5 mg, about 28 mg, about 28.5 mg, about 29 mg, about 29.5 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 12 mg, about 43 mg, about 44 mg, about 45 mg, about 46 mg, about 47 mg, about 48 mg, about 49 mg, about 50 mg, about 55 mg, about 60 mg, about 65 mg, about 70 mg, about 75 mg, about 80 mg, about 85 mg, about 90 mg, about 95 mg, about 100 mg, about 0.5 mg to about 12.5 mg, about 12.5 mg to about 50 mg, about 50 mg to about 75 mg, about 75 mg to about 100 mg, about 0.5 mg to about 15 mg, about 15 mg to about 35 mg, about 35 mg to about 55 mg, about 55 mg to about 75 mg, or about 75 mg to about 95 mg.

In some embodiments, the weight ratio of a first active pharmaceutical ingredient (e.g., triptan or a pharmaceutically acceptable salt thereof such as sumatriptan succinate) to a second active pharmaceutical ingredient (e.g., antiemetic such as promethazine or a pharmaceutically acceptable salt thereof for example promethazine hydrochloride) is from about 1:2 to about 15:1, respectively, for example about 1:2, about 1:1, about 2:1, about 2.5:1, about 3:1, about 4:1, about 5:1, about 6:1, about 7:1, about 8:1, about 9:1, about 10:1, about 11:1, about 12:1, about 13:1, about 14:1, or 15:1. In some embodiments, the weight ratio of a first active pharmaceutical ingredient (e.g., triptan or a pharmaceutically acceptable salt thereof such as sumatriptan succinate) to a second active pharmaceutical ingredient (e.g., antiemetic such as promethazine or a pharmaceutically acceptable salt thereof for example promethazine hydrochloride) is from about 3:2 to about 11:1, from about 3:1 to about 7:1, from about 1:1 to about 5:1, from about 9:2 to about 11:2, from about 4:2 to about 6:2, about 5:1, or about 2.5:1. In some embodiments, the weight ratio of a first active pharmaceutical ingredient (e.g., triptan or a pharmaceutically acceptable salt thereof such as sumatriptan succinate) to a second active pharmaceutical ingredient (e.g., antiemetic such as promethazine or a pharmaceutically acceptable salt thereof for example promethazine hydrochloride) is about 5:1. In some embodiments, the weight ratio of a first active pharmaceutical ingredient (e.g., triptan or a pharmaceutically acceptable salt thereof such as sumatriptan succinate) to a second active pharmaceutical ingredient (e.g., antiemetic such as promethazine or a pharmaceutically acceptable salt thereof for example promethazine hydrochloride) is about 2.5:1.

In some embodiments, the pharmaceutical composition described herein comprises from about 150 mg to about 400 mg of a plurality of first particulates, including, but not limited to, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or about 400 mg. In some embodiments, the pharmaceutical composition described herein comprises from about 150 mg to about 400 mg of a plurality of first particulates, including, but not limited to, about 175 mg to about 300 mg, about 200 mg to about 250 mg, about 200 mg to about 220 mg, about 150 mg to about 175 mg, about 175 mg to about 200 mg, about 200 mg to about 225 mg, about 225 mg to about 250 mg, about 250 mg to about 275 mg, about 275 mg to about 300 mg, about 300 mg to about 325 mg, about 325 mg to about 350 mg, about 350 mg to about 375 mg, about 375 mg to about 400 mg, about 165 mg to about 195 mg, about 195 mg to about 225 mg, about 225 mg to about 255 mg, about 255 mg to about 285 mg, about 285 mg to about 315 mg, about 315 mg, to about 345 mg, or about 345 mg to about 375 mg.

In some embodiments, the pharmaceutical composition described herein comprises from about 25 mg to about 300 mg of a plurality of second particulates, including, but not limited to, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5, about 70 mg, about 72.5 mg, about 75 mg, about 77.5 mg, about 80 mg, about 82.5 mg, about 85 mg, about 87.5 mg, about 90 mg, about 92.5 mg, about 95 mg, about 97.5 mg, about 100 mg, about 102.5 mg, about 105 mg, about 107.5 mg, about 110 mg, about 112.5 mg, about 115 mg, about 117.5 mg, about 120 mg, about 122.5 mg, about 125 mg, about 127.5 mg, about 130 mg, about 132.5 mg, about 135 mg, about 137.5 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 202.5 mg, about 205 mg, about 207.5 mg, about 210 mg, about 212.5 mg, about 215 mg, about 217.5 mg, about 220 mg, about 222.5 mg, about 225 mg, about 227.5 mg, about 230 mg, about 232.5 mg, about 235 mg, about 237.5 mg, about 240 mg, about 245 mg, about 250 mg, about 255 mg, about 260 mg, about 265 mg, about 270 mg, about 275 mg, about 280 mg, about 285 mg, about 290 mg, about 295 mg, or about 300 mg. In some embodiments, the pharmaceutical composition described herein comprises from about 25 mg to about 300 mg of a plurality of second particulates, including but not limited to, about 30 mg to about 150 mg, about 30 mg to about 100 mg, about 40 mg to about 100 mg, about 30 mg to about 70 mg, about 25 mg to about 50 mg, about 50 mg to about 75 mg, about 75 mg to about 100 mg, about 100 mg to about 125 mg, about 100 mg to about 115 mg, about 110 mg to about 125 mg, about 110 mg to about 115 mg, about 125 mg to about 150 mg, about 150 mg to about 175 mg, about 175 mg to about 200 mg, about 40 mg to about 70 mg, about 70 mg to about 100 mg, about 100 mg to about 130 mg, about 130 mg to about 160 mg, about 160 mg to about 190 mg, about 150 mg to about 250 mg, or 200 mg to about 250 mg.

In some embodiments, the pharmaceutical composition disclosed herein comprises a plurality of first particulates and a plurality of second particulates. In some embodiments, the plurality of first particulates is present in an amount that ranges from about 150 mg to about 400 mg, including, but not limited to, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, or 400 mg and the plurality of second particulates is present in an amount that ranges from about 25 mg to about 300 mg, including, but not limited to, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 52.5 mg, about 55 mg, about 57.5 mg, about 60 mg, about 62.5 mg, about 65 mg, about 67.5, about 70 mg, about 72.5 mg, about 75 mg, about 77.5 mg, about 80 mg, about 82.5 mg, about 85 mg, about 87.5 mg, about 90 mg, about 92.5 mg, about 95 mg, about 97.5 mg, about 100 mg, about 102.5 mg, about 105 mg, about 107.5 mg, about 110 mg, about 112.5 mg, about 115 mg, about 117.5 mg, about 120 mg, about 122.5 mg, about 125 mg, about 127.5 mg, about 130 mg, about 132.5 mg, about 135 mg, about 137.5 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 202.5 mg, about 205 mg, about 207.5 mg, about 210 mg, about 212.5 mg, about 215 mg, about 217.5 mg, about 220 mg, about 222.5 mg, about 225 mg, about 227.5 mg, about 230 mg, about 232.5 mg, about 235 mg, about 237.5 mg, about 240 mg, about 245 mg, about 250 mg, about 255 mg, about 260 mg, about 265 mg, about 270 mg, about 275 mg, about 280 mg, about 285 mg, about 290 mg, about 295 mg, or about 300 mg.

Dissolution

An example of a method to measure dissolution profiles is provided at Examples 4 and 5. In some aspects, dissolution rates are measured by a USP Apparatus 2 (Paddle Apparatus) at a speed of 50 rpm in a dissolution fluid of 500 ml de-aerated 0.1 N HCl (i.e., pH 1.1) at 37.0±0.5° C. In some instances, dissolution samples are analyzed by HPLC.

In some embodiments, dissolution of 100% of a pharmaceutically active agent disclosed herein occurs within a prescribed time. In some embodiments, a $5HT_{1B/1D}$ receptor agonist and an antiemetic disclosed herein both have a dissolution rate of about 60% or more within 15 minutes, following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, a $5HT_{1B/1D}$ receptor agonist or an antiemetic disclosed herein both have a dissolution rate of about 60% or more within 15 minutes, following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm.

In some embodiments, a $5HT_{1B/1D}$ receptor agonist and an antiemetic disclosed herein both have a dissolution rate of about 80% or more within 30 minutes, following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, a $5HT_{1B/1D}$ receptor agonist or an antiemetic disclosed herein both have a dissolution rate of about 80% or more within 30 minutes, following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm.

In some embodiments, at least about 32% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 47% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 53% of the antiemetic is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 69% of the antiemetic is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 63% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 78% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 71% of the antiemetic is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 82% of the antiemetic is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 79% of the antiemetic is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the antiemetic is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 85% of the antiemetic is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the antiemetic is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 88% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 100% of the antiemetic is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some cases the antiemetic is promethazine or a pharmaceutically acceptable salt thereof. In some cases the promethazine salt is promethazine chloride.

In some embodiments, at least about 56% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 66% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 73% of the $5HT_{1B/1D}$ receptor agonist is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 80% of the $5HT_{1B/1D}$ receptor agonist is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 81% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 85% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 84% of the $5HT_{1B/1D}$ receptor agonist is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 88% of the $5HT_{1B/1D}$ receptor agonist is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 87% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 90% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 91% of the $5HT_{1B/1D}$ receptor agonist is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 93% of the $5HT_{1B/1D}$ receptor agonist is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 92% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 94% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, at least about 97% of the $5HT_{1B/1D}$ receptor agonist is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some embodiments, at least about 98% of the $5HT_{1B/1D}$ receptor agonist is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some cases the $5HT_{1B/1D}$ receptor agonist is a triptan or a pharmaceutically acceptable salt thereof. In some cases the triptan is sumatriptan or a pharmaceutically acceptable salt thereof. In some cases the pharmaceutically acceptable salt of sumatriptan is sumatriptan succinate.

In some embodiments, the dissolution profile is measured after storage at 40° C. for 1 month. In some embodiments, after storage at 40° C. for 1 month at least about 35% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 43% of the antiemetic is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 54% of the antiemetic is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 64% of the antiemetic is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 63% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 73% of the antiemetic is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 68% of the antiemetic is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 79% of the antiemetic is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 74% of the antiemetic is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the antiemetic is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 80% of the antiemetic is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 89% of the antiemetic is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 88% of the antiemetic is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 99% of the antiemetic is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some cases the antiemetic is promethazine or a pharmaceutically acceptable salt thereof. In some cases the promethazine salt is promethazine chloride. In some embodiments, after storage at 40° C. for 1 month at least about 47% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 60% of the $5HT_{1B/1D}$ receptor agonist is released within about 5 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 62% of the $5HT_{1B/1D}$ receptor agonist is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 76% of the $5HT_{1B/1D}$ receptor agonist is released within about 10 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 69% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 81% of the $5HT_{1B/1D}$ receptor agonist is released within about 15 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 74% of the $5HT_{1B/1D}$ receptor agonist is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 85% of the $5HT_{1B/1D}$ receptor agonist is released within about 20 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 80% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 88% of the $5HT_{1B/1D}$ receptor agonist is released within about 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 84% of the $5HT_{1B/1D}$ receptor agonist is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 91% of the $5HT_{1B/1D}$ receptor agonist is released within about 45 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 86% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 93% of the $5HT_{1B/1D}$ receptor agonist is released within about 60 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm. In some embodiments, after storage at 40° C. for 1 month at least about 96% of the $5HT_{1B/1D}$ receptor agonist is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some embodiments, after storage at 40° C. for 1 month at least about 98% of the $5HT_{1B/1D}$ receptor agonist is released within about 90 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 250 rpm. In some cases the $5HT_{1B/1D}$ receptor agonist is a triptan or a pharmaceutically acceptable salt thereof. In some cases the triptan is sumatriptan or a pharmaceutically acceptable salt thereof. In some cases the pharmaceutically acceptable salt of sumatriptan is sumatriptan succinate.

In some cases, the antiemetic disclosed herein dissolves at a slower rate than the $5HT_{1B/1D}$ receptor agonist disclosed herein. In some cases, the antiemetic is characterized by less dissolution than the $5HT_{1B/1D}$ receptor agonist after 5 minutes, after 10 minutes, after 15 minutes, after 20 minutes, or after 30 minutes following contact of the pharmaceutical composition with 500 mL of a dissolution fluid (0.1N HCl, pH 1.1) at 37+/−0.5° C. as measured by an Apparatus 2 (Paddle Apparatus) rotating at 50 rpm.

In some embodiments, dissolution of less than all of the agent disclosed herein occurs in about 1 minute to about 90 minutes (e.g., dissolution of about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5% or 99.9% of an agent).

Stability

In some embodiments, the pharmaceutical composition disclosed herein is stable for at least about: 30 days, 60 days, 90 days, 6 months, 1 year, 18 months, 2 years, 3 years, 4 years, or 5 years, for example about 80%-100% such as about: 80%, 90%, 95%, or 100% of each active pharmaceutical agent in the pharmaceutical composition is stable, e.g., as measured by High Performance Liquid Chromatography (HPLC) such as the HPLC method in Example 7. In some embodiments, about 80%-100% (e.g., about: 90%-100% or 95-100%) of a 5HT1B/1D receptor agonist (e.g., triptan such as sumatriptan) or a pharmaceutically acceptable salt thereof (e.g., sumatriptan succinate) in the pharmaceutical composition disclosed herein is stable for at least about: 30, 60, 90, 180, 360, 540, or 720 days, for example greater than 90 days, which can be measured by HPLC such as the method in Example 7. In some embodiments, about: 80%, 85%, 90%, 95%, or 100% (e.g., about 95%) of the $5HT_{1B/1D}$ receptor agonist (e.g., triptan such as sumatriptan) or the pharmaceutically acceptable salt thereof (e.g., sumatriptan succinate) is stable for 30 days or more, which can be measured by HPLC such as the method in Example 7. In some embodiments, about 80%-100% (e.g., about: 90%-100% or 95-100%) of an antiemetic (e.g. promethazine or a pharmaceutically acceptable salt thereof such as promethazine hydrochloride) in the pharmaceutical composition disclosed herein is stable for at least about: 30, 60, 90, 180, 360, 540, or 720 days, for example greater than 90 days, which can be measured by HPLC such as the method in Example 7. In some embodiments, about: 80%, 85%, 90%, 95%, or 100% (e.g., about 100%) of the antiemetic (e.g. promethazine or a pharmaceutically acceptable salt thereof such as promethazine hydrochloride) is stable for 30 days or more, which can be measured by HPLC such as the method in Example 7.

Methods of Treatment

In some aspects, a method is provided for treating pain, comprising administering to a subject in need thereof a pharmaceutical composition comprising a therapeutically effective amount of each of a $5HT_{1B/1D}$ receptor agonist and an antiemetic disclosed herein. In some embodiments, the $5HT_{1B/1D}$ receptor agonist is a triptan. In some embodiments, the antiemetic is promethazine or a pharmaceutically acceptable salt thereof. In some aspects, a method is provided for treating pain, comprising administering to a subject in need a pharmaceutical composition that includes a plurality of first particulates comprising a therapeutically effective amount of a $5HT_{1B/1D}$ receptor agonist or a pharmaceutically acceptable salt thereof; and a plurality of second particulates comprising a therapeutically effective amount of an antiemetic. In some embodiments, the $5HT_{1B/1D}$ receptor agonist is a triptan. In some embodiments, the antiemetic is promethazine or a pharmaceutically acceptable salt thereof.

In some aspects, a method is provided for treating pain, comprising administering to a subject in need a pharmaceutical composition that includes a plurality of particulates comprising a therapeutically effective amount of a triptan or a pharmaceutically acceptable salt thereof; and a powder comprising a therapeutically effective amount of an antiemetic. In some aspects, a method is provided for treating pain, comprising administering to a subject in need a pharmaceutical composition that includes a plurality of particulates comprising a therapeutically effective amount of an antiemetic; and a powder comprising a therapeutically effective amount of a triptan or a pharmaceutically acceptable salt thereof. In some aspects, a method is provided for treating pain, comprising administering to a subject in need a pharmaceutical composition that includes a first powder comprising a therapeutically effective amount of an antiemetic; and a second powder comprising a therapeutically effective amount of a triptan or a pharmaceutically acceptable salt thereof.

In some embodiments, a plurality of particulates described herein are encapsulated into discrete units. In some embodiments, the discrete units are capsules or packets. In some embodiments, a method is provided for treating pain, comprising administering the capsule or the packet containing a plurality of particulates as described herein. In some embodiments, a method of treating pain includes breaking the capsule or the packet to sprinkle the plurality of particulates on food or soft foods and swallowed without chewing. In some embodiments, the plurality of particulates is administered through an enteral feeding tube. In some embodiments, the pain is associated with a headache, such as a chronic headache, cluster headache or a migraine headache. In one embodiment the migraine headache occurs with aura. In some embodiments, the migraine headache is accompanied by symptoms, including, but not limited to vomiting, nausea, photophobia, phonophobia, or osmophobia.

In some embodiments, the photophobia is characterized by light sensitivity or light hypersensitivity. In some cases, the photophobia is caused by acute iritis or uveitis (inflammation inside eye), burns to the eye, corneal abrasion, corneal ulcer, drug side effects, excessive wearing of contact lenses, or wearing badly-fitted contact lenses, eye disease, injury, or infection (such as chalazion, episcleritis, glaucoma), eye testing when the eyes have been dilated, meningitis, migraine headache, or recovery from eye surgery. In some cases, the photophobia is associated with a migraine. In some cases, the photophobia is associated with nausea and vomiting. In some cases, the photophobia is associated with nausea or vomiting.

In some embodiments, a pharmaceutical composition defined herein is for the reduction of ocular pain, itching, burning, and/or stinging, and/or photophobia, following a surgery or postoperative inflammation. In some embodiments, a pharmaceutical composition defined herein is given at the time of pupil dilation. In some embodiments, the pharmaceutical composition disclosed herein is for use in treatment of a photophobia wherein the treatment is prophylactic. In instances cases, the pharmaceutical composition disclosed herein is for use in treatment of a photophobia wherein the treatment is preventative. In some cases, preventative treatment is to decrease migraine frequency. In some embodiments, the pharmaceutical composition disclosed herein is for use in treatment of a photophobia wherein the treatment is preemptive. In some cases, preemptive treatment is used when a photophobia trigger is time-limited or predictable. In some embodiments, the pharmaceutical composition disclosed herein is for use in treatment of a photophobia wherein the treatment is acute. In some cases, treatment is to stop or prevent progression of a photophobia. In some cases, acute treatment is initiated during an attack to relieve pain. In some cases, a pharmaceutical composition disclosed here is used for preventive, acute, and/or preemptive treatment for photophobia.

In some embodiments, the pharmaceutical composition disclosed herein is for use in treatment of a headache wherein the treatment is prophylactic. In instances cases, the pharmaceutical composition disclosed herein is for use in treatment of a headache wherein the treatment is preventative. In some cases, preventative treatment is to decrease migraine frequency. In some embodiments, the pharmaceutical composition disclosed herein is for use in treatment of a headache wherein the treatment is preemptive. In some cases, preemptive treatment is used when a headache trigger is time-limited or predictable. In some embodiments, the pharmaceutical composition disclosed herein is for use in treatment of a headache wherein the treatment is acute. In some cases, treatment is to stop or prevent progression of a migraine. In some cases, acute treatment is initiated during an attack to relieve pain. In some cases, a pharmaceutical composition disclosed here is used for preventive, acute, and/or preemptive treatment for a headache.

In some embodiments, the pharmaceutical composition disclosed herein is used for treatment of chronic migraine headache. In some embodiments, the pharmaceutical composition disclosed herein is for use in treatment of a migraine headache wherein the treatment is prophylactic. In some embodiments, the pharmaceutical composition disclosed herein is for use in treatment of a migraine headache wherein the treatment is of an acute migraine headache. In some embodiments, the pharmaceutical composition disclosed herein is for use in treatment of a migraine wherein the treatment is of a chronic migraine headache. In some embodiments, the pharmaceutical composition disclosed herein is for use in treatment of a migraine headache with an aura. In some embodiments, the pharmaceutical composition disclosed herein is for use in treatment of a migraine headache without an aura. In some embodiments, the pharmaceutical composition disclosed herein is for use in treatment of a cluster headache. In some embodiments, the pharmaceutical composition disclosed herein is for use in treatment of nausea or vomiting. In some embodiments, the pharmaceutical composition disclosed herein is for use in treatment of nausea and vomiting. In some embodiments, the pharmaceutical composition disclosed herein is for use in treatment of nausea associated with a headache or vomiting associated with a headache. In some embodiments, the pharmaceutical composition disclosed herein is for use in treatment of nausea associated with a headache and vomiting associated with a headache. In some embodiments, the pharmaceutical composition disclosed herein is for use in treatment of nausea associated with a migraine headache or vomiting associated with a migraine headache. In some embodiments, the pharmaceutical composition disclosed herein is for use in treatment of nausea associated with a migraine headache and vomiting associated with a migraine headache.

In some embodiments, the pharmaceutical composition disclosed herein (e.g., capsule) does not completely disintegrate in mouth within about 1, about 2, about 3, about 4, about 5, about 6, about 7, about 8, about 9, about 10, about 11, about 12, about 13, about 14, about 15, about 16, about 17, about 18, about 19 or about 20 minutes. In some embodiments, the pharmaceutical composition disclosed herein is not a film. In some embodiments, the pharmaceutical composition disclosed herein is not for buccal administration. In some embodiments, the pharmaceutical composition disclosed herein (e.g., capsule) dissolves in stomach or intestine.

In some embodiments, the subject is a mammal, e.g., a human, mouse, rat, guinea pig, dog, cat, horse, cow, pig, or non-human primate, such as a monkey, chimpanzee or baboon. In some embodiments, the subject is a human. In some embodiments, the subject administered a pharmaceutical composition as described herein is about 55 years of age or older, about 60 years of age or older, about 65 years of age or older, or about 70 years of age or older. In some embodiments, the subject administered a pharmaceutical composition described herein is 18 years of age or older. In some embodiments, the subject is between 35 and 45 years of age. In some embodiments, the subject administered a pharmaceutical composition described herein has a history of headaches. In some embodiments, the subject administered a pharmaceutical composition described herein has a history of migraines.

In some embodiments, a pharmaceutical composition described herein is administered to the subject (e.g., a patient) at the time of onset of the migraine headache as needed by the subject (e.g., a patient) or as determined and instructed by the physician. In some embodiments, the subject administered a pharmaceutical composition described herein suffers from adverse effects associated with triptan administration. Examples of adverse effects include nausea and/or vomiting, e.g., associated with a migraine. In some embodiments, the pharmaceutical composition described herein reduces or prevents unwanted side effects associated with injectable or tablet triptan therapy, including, flushing, sweating, vertigo, fatigue, tingling, drowsiness, dizziness, dry mouth, heartburn, abdominal pain, abdominal cramps, weakness, feeling of warmth or coldness, bitter taste from tablets and nasal sprays, and local burning from injection site.

In some embodiments, a pharmaceutical composition described herein is administered to a subject at about every 12 to about 24 hours, about every 12 hours, or about every 24 hours. In some embodiments, a pharmaceutical composition described herein is administered to a subject at about every 8 to about every 12 hours. In some embodiments, a pharmaceutical composition described herein is administered once, twice or three times daily. In some embodiments, a pharmaceutical composition described herein is administered no more than twice daily. In some embodiments, a second dose of the pharmaceutical composition disclosed herein is administered after response to a first dose in a subject. In some embodiments, doses after a first dose of a pharmaceutical composition described herein are separated by at least 2 hours. In some embodiments, the maximum dose of a pharmaceutical composition described herein over a 24 hour period does not exceed 200 mg. In some embodiments, a maximum single dose of a pharmaceutical composition described herein dose does not exceed 50 mg in a subject with mild to moderate hepatic impairment.

In some embodiments, a pharmaceutical composition described herein comprising sumatriptan succinate and promethazine hydrochloride is administered to a subject at about every 12 to about 24 hours, about every 12 hours, or about every 24 hours. In some embodiments, a pharmaceutical composition described herein comprising sumatriptan succinate and promethazine hydrochloride is administered to a subject at about every 4 to about every 6 hours. In some embodiments, a pharmaceutical composition described herein comprising sumatriptan succinate and promethazine hydrochloride is administered to a subject at about every 8 to about every 12 hours. In some embodiments, a pharmaceutical composition described herein comprising sumatriptan succinate and promethazine hydrochloride is administered once, twice or three times daily. In some embodiments, a pharmaceutical composition described herein comprising sumatriptan succinate and promethazine hydrochloride is administered no more than twice daily. In some embodiments, a second dose of the pharmaceutical composition disclosed herein comprising sumatriptan succinate and promethazine hydrochloride is administered after response to a first dose in a subject. In some embodiments, doses after a first dose are separated by at least 2 hours. In some embodiments, the maximum dose of the pharmaceutical composition disclosed herein comprising sumatriptan succinate and promethazine hydrochloride over a 24 hour period does not exceed 200 mg. In some embodiments, a maximum single dose of the pharmaceutical composition disclosed herein comprising sumatriptan succinate and promethazine hydrochloride does not exceed 50 mg in a subject with mild to moderate hepatic impairment. In some embodiments, the frequency of dosing is determined or assessed by a professional assessing the subject, the severity of the condition and expected duration of therapy.

In some aspects, a method is provided for treating pain comprises administering to a subject in need thereof a pharmaceutical composition comprising a therapeutically effective amount of a triptan; an antiemetic. In some embodiments, the pain is a headache. In some embodiments, the headache is a migraine headache. In some embodiments, the headache is a cluster headache. In some embodiments, the method is also useful for treating photophobia. In some embodiments, the photophobia is associated with migraine headache. In some embodiments, a method for treating headache comprises: administering to a subject in need thereof a pharmaceutical composition comprising a therapeutically effective amount of sumatriptan or a pharmaceutically acceptable salt thereof; promethazine or a pharmaceutically acceptable salt thereof. In some embodiments, a method for treating headache comprises administering to a subject in need thereof a pharmaceutical composition comprising: a therapeutically effective amount of sumatriptan or a pharmaceutically acceptable salt thereof; promethazine or a pharmaceutically acceptable salt thereof.

Methods of Manufacture

In some embodiments, a method is provided for manufacturing a pharmaceutical composition as described herein. In some embodiments, the pharmaceutical composition as described herein is prepared by standard techniques and using standard equipment known to the skilled person.

In some embodiments, a plurality of first particulates comprising an active pharmaceutical ingredient such as triptan (e.g., sumatriptan or a pharmaceutically acceptable salt thereof) are prepared by a process method comprising forming small spherical pellets with a narrow size distribution. In some embodiments, the first particulates comprise a non-pharmaceutically active ingredient selected from the group consisting of microcrystalline cellulose, dicalcium phosphate, calcium sulfate, talc, an alkali metal stearate, silicon dioxide, calcium carbonate, and any combinations thereof. When the desired particle size has been achieved, the pellets may be seal coated to improve their strength, and are then dried to the desired moisture content. Any oversized or undersized product is removed by sieving, and the resulting pellets are narrow in size distribution. In some embodiments, the first particulates are sifted through a nest of screens of size #40 to #140 to further determine particle size range. In some embodiments, the plurality of particulates is mixed with a coating material. In one example, the coating is performed by spraying.

In some embodiments, the plurality of second particulates comprising an active pharmaceutical ingredient such as an antiemetic are prepared by a process method comprising layering an active ingredient onto the outside of an inert core. In some embodiments, the inert core is a sugar sphere. In some embodiments, the inert core is a microcrystalline cellulose sphere.

In some embodiments, a solution or suspension comprising an antiemetic (e.g., promethazine or a pharmaceutically acceptable salt thereof) is layered onto the inert core via spraying. Spraying process include top spray, tangential spray, bottom spray (Wurster process) or rotor process, depending from which direction the particles are being sprayed. In some embodiments, the solution or suspension layering is done by using bottom spray (Wurster process). In some embodiments, the solution or suspension comprising an antiemetic (e.g., promethazine or a pharmaceutically acceptable salt thereof) further comprises pharmaceutically acceptable excipients. In some embodiments, the pharmaceutically acceptable excipients comprise a disintegrant. In some embodiments, the pharmaceutically acceptable excipients comprise hydroxypropyl methylcellulose (HPMC). In some embodiments, the pharmaceutically acceptable excipients comprise low substituted hydroxypropyl methylcellulose (L-HPC). In some embodiments, the pharmaceutically acceptable excipients comprise talc. In some embodiments, the antiemetic (e.g., promethazine or a pharmaceutically acceptable salt thereof) is mixed with hydroxypropyl methylcellulose and dissolved in a pharmaceutically acceptable solvent (i.e., water) followed by addition of low substituted hydroxypropyl methylcellulose (L-HPC) talc, and any combinations thereof. In some embodiments, the resulting solution/dispersion is sprayed onto an inert core. In some embodiments, the particulates are dried to the desired residual moisture content once the desired potency has been achieved. In some embodiments, any oversized or undersized product is removed by sieving, and the resulting pellets are narrow in size distribution.

In some embodiments, the active ingredient layer is applied by powder layering. In some embodiments, the powder layer comprises only the active ingredient. In some embodiments, the powder layer comprises the active ingredient and pharmaceutically acceptable excipients. In some embodiments, the pharmaceutically acceptable excipients comprise binders, lubricants, inert fillers, and the like. Powder layering may be conducted using a wide variety of processing techniques. In some embodiments, the powder layering is done by rotary fluidized bed. A pharmaceutically acceptable liquid, which may be water, organic solvent, with or without a binder and/or excipients, is applied to the inert core while applying the dry powder until the desired potency is achieved. When the desired potency has been achieved, the pellets may be seal coated to improve their strength, and are then dried to the desired moisture content. Any oversized or undersized product is removed by sieving, and the resulting pellets are narrow in size distribution.

In some embodiments, the second particulates obtained are transferred to a vector fluid bed dryer. In some embodiments, the dryer presets drying parameters such as, but not limited to, inlet temperature of between 55-65° C. or 70° C., outlet temperature of between 20-30° C. or 30-40° C., product temperature of between 20-45° C. or 21-42° C., total time of 45-75 minutes, fan at 180-740 lpm (liters per minute). In some embodiments, loss on drying (LOD) values following the drying step is between 1.5-3%. In some embodiments, the second particulates are sifted through a nest of screens of size #14 to #20 to further determine particle size range. In some embodiments, the plurality of particulates is mixed with a coating material. In one example, the coating is performed by spraying.

EXAMPLES

The following examples are offered by way of illustration and not by way of limitation.

Example 1. Preparation of Sumatriptan Particulates

Sumatriptan Succinate Milling

A jet mill was set up with guard and covers permanently mounted in place and a cover on the feeder inlet. Setting on the powder feeder was adjusted to deliver 500 g/min (±200 g/min) of powder. Sumatriptan succinate USP (500 g) was placed in the powder feeder. The air was energized and the air inlet pressure was to 80 psig by using the regulator on the utility manifold. The grind air valve was approximately set to 50 psig and the feed air valve was set to 50 psig by using hand adjustable valves on the Micronizer table. The powder feed was turned on and the milling process was started. The milled sumatriptan succinate was placed in a double lined polyethylene bag sealed with a plastic bag tie.

Formation of Sumatriptan Pellets (Process Repeated 3 Times)

A CPS-30 insert (with a 45° rotor plate angle, steep baffles at position 1 and 3, and atomizer set at middle position, powder feeder, discharge drum) was loaded with micronized sumatriptan succinate (9 kg) and microcrystalline cellulose (5.25 kg, Avicel PH101). The powder feeder was loaded with additional microcrystalline cellulose (0.75 kg, Avicel PH101). The powders were kept away from the rotary atomizer. Compress the CPS-30 insert in place. On the CPS-30 local panel, the air purge regulator was opened to 1.0 bar (±0.2 bar) and the air regulator for the rotary atomizer was opened until the speed reached and stabilized at 5000 rpm (±300 pm). The process was switched to "spraying" at 500 g/min. The rotor drive was started and adjusted to a speed of 280 rpm (±20 rpm) when the process air volume reached 14 CFM. The 500 g/min was continued for 3 minutes and was followed by the steps below:

The spray rate was reduced to 200 g/min (±10 g/min) at 3 minutes;

The rotor speed was increased to 300 rpm after 2.5 kg of water has been sprayed; and The spray rate was reduced to 160 g/min (±10 g/min) after 2.5 kg of water has been sprayed.

The pellets were collected from the CPS-30 sample port. When the wet pellet size has been visually observed to be approximately within range of 200 to 400 μm, with a target wet pellet size of approximately 250 μm, the powder feeder was engaged and the additional microcrystalline cellulose was applied at 250 g/min (±20 g/min). The powder feeder was stopped when the powder in the powder feeder was depleted. The spraying was also stopped.

The pellets were tumbled for 2-4 minutes and were then discharged in a discharge vessel.

Drying of Sumatriptan Pellets

The pellets were dried until the temperature reached 52° C. using the following settings:

| Fan Speed | #3 setting (highest) |
|---|---|
| Bypass/Inlet Temperature | 60 ± 10° C. |
| Dew Point | 10 ± 3° C. |
| Total Air Flow | 1500 ± 300 CFM |

The residual moisture was checked. The drying process was stopped when the moisture was less than 2% (if moisture was more than 2% the drying process was continued for an additional 10 minutes).

The pellets were discharged in a double lined polyethylene lined container.

Particles Size

The size of the particles was assessed using a Ro-Tap R fitted with standard U.S. mesh screen and a pan (5 minute shake).

The discharged material was sieve cut using a U.S. Standard #40 mesh screen and U.S. Standard #140 mesh screen.

Blending

The sumatriptan succinate pellets (potency 60%, Sieve Cut 40/140) were loaded in a V-blender. The pellets were blended for 4 minutes. The pellets were then discharged in a tared double polyethylene lined container.

Example 2. Preparation of Promethazine Particulates

Preparation of the Drug Layering Solution

Purified water, USP, (65 kg) was weighed in an appropriately sized container. A propeller mixer was started. While mixing, promethazine hydrochloride, USP 38 (9.38 kg) was added and mixed until a clear solution was obtained. While mixing the solution, hydroxypropyl methylcellulose (2.5 kg, Methocel E5 LV Premium) was slowly added and the mixing was continued until a clear solution was obtained (about 30 minutes).

Purified water, USP, (15.47 kg) was weighed in an appropriately sized container. A homogenizer was started. While mixing, talc (0.47 kg, Pharma 400 USP) was slowly added and the homogenizing was continued until the talc was uniformly dispersed. The homogenizer was replaced with an air mixer. While mixing the talc dispersion with the air mixer, low substituted hydroxypropyl cellulose NF (0.94 kg, LH-31) was slowly added and the mixing was continued until a uniform dispersion was obtained.

While mixing the promethazine/hydroxypropyl methylcellulose solution, the talc/L-HPC dispersion was slowly added. The mixture was then mixed for a minimum of 10 minutes. The weight of the promethazine solution/dispersion was recorded.

Preparation of the Top Coating Solution

Purified water, USP, (21.69 kg) was weighed in an appropriately sized container. A propeller mixer was started. While mixing, Opadry II Complete film coating system (3.83 kg, 85F18422 white powder) was slowly added and the mixing was continued for about 30 minutes. The weight of the top coating solution was recorded.

Spraying of Drug Layer Dispersion/Solution

A dip tube was secured to the side of the container and a gap was left between the bottom of the dip tube and the bottom of the container. Fluid bed with 18" Wurster insert with HS Collar was preheated for at least 10 minutes.

The Suglets® Sugar Sphere (25 kg, PF010 710/850 Suglets) were placed into the Fluid bed with 18" Wurster insert and spraying the drug layering dispersion/solution was started using the initial target processing conditions below:

| Inlet Temperature | 60 ± 30° C. |
|---|---|
| Inlet Air Dew Point | 10 ± 5° C. |
| Air Volume | 600-12000 CFM |
| Spray Rate | 100-300 ± 50 g/min |
| Atomization Air Pressure | 2.5 ± 1.0 bar |
| Product Temperature Range | 45 ± 10° C. |
| Shake Interval/Duration | 30 sec/5 sec |

Agglomeration was checked using Standard #18 mesh screen (or as appropriate). Upon completion of the spraying of the drug layering, Purified water, USP, (0.1 kg) was added to the drug layering solution container and the lines were purged using the same parameters used above. The drug layering solution line and dip tube were removed.

Spraying of the Top Coating Solution

The drug layering solution container was removed and replaced with the top coat solution container. A new dip tube was set up and connected to a spray wand. After the pellets were dried for not less than 1 minute, the top coating solution was sprayed using the initial target processing conditions below:

| Inlet Temperature | 60 ± 30° C. |
|---|---|
| Inlet Air Dew Point | 10 ± 5° C. |
| Air Volume | 600-12000 CFM |
| Atomization Air Pressure | 2.5 ± 1.0 bar |
| Product Temperature Range | 50 ± 10° C. |
| Shake Interval/Duration | 30 sec/5 sec |

Agglomeration was checked using Standard #14 mesh screen (or as appropriate). Upon completion of the spraying of the top coat layer, Purified water, USP, (0.1 kg) was added to the top coat solution container and the lines were purged using the same parameters used above and the pellet were dried for a minimum of 5 minutes.

Final Product

The finished product was discharged into a tared double polyethylene lined container. The final product was screened using Sweco U.S. Standard #14 mesh and Sweco U.S. Standard #20 mesh.

Example 3. Preparation of a Capsule Formulation

Sumatriptan particulates and promethazine particulates were generated as disclosed in Example 1 and Example 2, and then encapsulated together in a capsule. A list of ingredients is provided in Table 1 and Table 2.

TABLE 1

Uncoated Sumatriptan Particulates

| Ingredients | Percent (w/w) | Quantity (mg) |
|---|---|---|
| Sumatriptan succinate | 60 | 126 |
| Microcrystalline Cellulose | 40 | 84 |
| Total | 100 | 210 |

TABLE 2

Coated Promethazine Particulates

| Ingredients | Percent (w/w) | Quantity (mg) |
|---|---|---|
| Promethazine Hydrochloride | 22.3 | 25 |
| Sugar Sphere | 59.4 | 66.6 |
| Hydroxypropyl methylcellulose (HPMC) | 5.9 | 6.6 |
| Low substituted hydroxypropyl cellulose (L-HPC) | 2.2 | 2.5 |
| Talc | 1.1 | 1.2 |
| Opadry II (top coat) | 9.1 | 10.2 |
| Sterile Water for Irrigation, USP | qs | |
| Total | 100 | 112.1 |

Sumatriptan (potency 60%, Sieve Cut 40/140) particulates (210±5% mg) and promethazine HCl (potency 22.3%) coated particulates (112.1±5% mg) were encapsulated into Size 0 capsules (Coni-Snap, White Opaque). The capsules were packaged in opaque HDPE bottles. Formulation of capsules comprising sumatriptan and promethazine is as described in Table 3.

TABLE 3

Encapsulated Formulation

| Ingredient | Percent w/w | mg/capsule |
|---|---|---|
| Sumatriptan particulates | 65.2% | 210 |
| Promethazine particulates | 34.8% | 112.1 |

Example 4. Preparation of a Capsule Formulation

Sumatriptan particulates and promethazine particulates were generated as disclosed in Example 1 and Example 2, and then encapsulated together in a capsule. A list of ingredients is provided in Table 4 and Table 5.

TABLE 4

Uncoated Sumatriptan Particulates

| Ingredients | Percent (w/w) | Quantity (mg) |
|---|---|---|
| Sumatriptan succinate | 60 | 126 |
| Microcrystalline Cellulose | 40 | 84 |
| Total | 100 | 210 |

TABLE 5

Coated Promethazine Particulates

| Ingredients | Percent (w/w) | Quantity (mg) |
|---|---|---|
| Promethazine Hydrochloride | 22.3 | 50 |
| Sugar Sphere | 59.4 | 133.2 |
| Hydroxypropyl methylcellulose (HPMC) | 5.9 | 13.2 |
| Low substituted hydroxypropyl cellulose (L-HPC) | 2.2 | 5 |
| Talc | 1.1 | 2.4 |
| Opadry II (top coat) | 9.1 | 20.4 |
| Sterile Water for Irrigation, USP | qs | |
| Total | 100 | 224.2 |

Sumatriptan (potency 60%, Sieve Cut 40/140) particulates (210±5% mg) and promethazine HCl (potency 22.3%) coated particulates (224.2±5% mg) were encapsulated into Size 0 capsules (Coni-Snap, White Opaque). The capsules were packaged in opaque HDPE bottles. Formulation of capsules comprising sumatriptan and promethazine is as described in Table 6.

TABLE 6

Encapsulated Formulation

| Ingredient | Percent w/w | mg/capsule |
|---|---|---|
| Sumatriptan particulates | 48.3% | 210 |
| Promethazine particulates | 51.7% | 224.2 |

Example 5. Dissolution Measurements by USP Basket Method

Dissolution studies are conducted to measure the rates of dissolution of active ingredients using a USP Apparatus 1 (Basket Apparatus) with a dissolution fluid of 900 ml deaerated 0.01 N HCl (i.e., pH 2.0) at 37.0+/−0.5° C. Dissolution samples were analyzed by HPLC.

Dissolution medium of 0.01N HCl is prepared by mixing well approximately 5 ml of concentrated (12N) Hydrochloric Acid with 6 L of water. Stock promethazine HCl standard solution is prepared by adding approximately 30 ml of dissolution medium to 14.0 mg of dried Promethazine Hydrochloride USP reference standard in a 50 ml volumetric flask, diluted to volume with dissolution media, and mixed well. Working Standard Solution is prepared by first mixing well 14.0 mg of Sumatriptan Succinate USP reference standard with approximately 60 ml of dissolution medium and then pipetting 10.0 ml of Promethazine Hydrochloride stock solution into the prepared Sumatriptan Succinate solution. The resulting solution is diluted to volume with dissolution medium and mixed well. Nominal concentration for Sumatriptan was 0.10 mg/ml (as a free base) and Promethazine HCl is 0.028 mg/ml in the Sumatriptan Succinate and Promethazine HCl Working Standard A and B. The label claim for Sumatriptan is as a free base and therefore the final standard concentration is converted accordingly multiplying by the salt-to-base conversion factor: (295.40/413.49).

The dissolution apparatus used is USP Apparatus 1 (Basket) with a speed of 100 rpm at 37.0° C.±0.5° C. Dissolution medium (900 ml) was Helium sparged for at least 10 minutes. N=6 samples were tested, one per sinker and per vessel. At each time point of 5, 15, 30, and 45 minutes, a 5 ml aliquot from each dissolution vessel is filtered through a 0.45 μm Nylon membrane syringe filter before HPLC analysis.

HPLC conditions: Flow rate: 1.0 ml/min; Injection Volume: 5 µL; Column Temperature: 40° C.; Wavelengths: 254 nm; Run Time: 7 minutes; Mobile Phase A was 0.2% TFA in Water, which was prepared by mixing well 2.0 ml of trifluoroacetic acid with 1 L of water. Mobile Phase B: 0.2% TFA in Acetonitrile, which was prepared by mixing well 2.0 ml of trifluoroacetic acid to 1 L of acetonitrile; and Gradient used was as follows in Table 6.

TABLE 7

| Time (minutes) | % A (Buffer) | % B (ACN) |
| --- | --- | --- |
| Initial | 90 | 10 |
| 4.0 | 40 | 60 |
| 4.1 | 90 | 10 |
| 7.0 | 90 | 10 |

Approximate Retention Times for sumatriptan and promethazine are 2.8 minutes and 4.8 minutes respectively.

Calculation.

Calculations for percent release are conducted using the following formulas. Percent Release of Promethazine (Profile):

$$\% \text{ Released} = \left[\left(\frac{R_u}{R_s} \times C_{std} \times V_d\right) + \sum_{i=1}^{n-1}\left(\frac{R_i}{R_s} \times C_{std} \times V_i\right)\right] \times \left(\frac{1}{LC}\right) \times 100$$

Where:
$R_u$=Peak area of Promethazine in the sample preparation
$R_s$=Mean peak area of Promethazine in all Working Standard A injections
$C_{std}$=Working Standard A concentration of Promethazine Hydrochloride, adjusted for purity (µg/ml)
$V_d$=Volume of dissolution medium at the pull time (ml)
$R_i$=Peak area of Promethazine obtained from the sample preparation at the individual pull points
$V_i$=Volume of the sample removed from the vessel at the pull point (ml)
LC=Label claim (25 mg or 25000 µg)
100=Conversion to percent Percent Release of Sumatriptan (Profile):

$$\% \text{ Released} = \left[\left(\frac{R_u}{R_s} \times C_{std} \times V_d\right) + \sum_{i=1}^{n-1}\left(\frac{R_i}{R_s} \times C_{std} \times V_i\right)\right] \times \left(\frac{1}{LC}\right) \times 100$$

Where:
$R_u$=Peak area of Sumatriptan in the sample preparation
$R_s$=Mean peak area of Sumatriptan in all Working Standard A injections
$C_{std}$=Working Standard A concentration of Sumatriptan, succinate adjusted for purity and conversion to free base (µg/ml)
$V_d$=Volume of dissolution medium at the pull time (ml)
$R_i$=Peak area of Sumatriptan obtained from the sample preparation at the individual pull points
$V_i$=Volume of the sample removed from the vessel at the pull point (ml)
LC=Label claim (90 mg or 90000 µg)
100=Conversion to percent Example 6. Dissolution Measurement by USP Paddle Method Dissolution studies were conducted to measure the rates of dissolution of active ingredients using a USP Apparatus 2 (Paddle Apparatus) with a dissolution fluid of 500 ml deaerated 0.1 N HCl (i.e., pH 1.1) at 37.0+/−0.5° C. Dissolution samples were analyzed by HPLC.

Dissolution medium of 0.1N HCl was prepared by mixing approximately 85 ml of concentrated (12N) Hydrochloric Acid with 10 L of water. Stock promethazine HCl standard solution was prepared by adding approximately 30 ml of dissolution medium to 25.0 mg of dried Promethazine Hydrochloride USP reference standard in a 50 ml volumetric flash, diluted to volume with dissolution media, and mixed well. Working Standard Solution is prepared by first mixing well 25.2 mg of Sumatriptan Succinate USP reference standard with approximately 60 ml of dissolution medium and then pipetting 10.0 ml of Promethazine Hydrochloride stock solution into the prepared Sumatriptan Succinate solution. The resulting solution is diluted to volume with dissolution medium and mixed well. Nominal concentration for Sumatriptan succinate was 0.252 mg/ml and Promethazine HCl was 0.05 mg/ml.

The dissolution apparatus used is USP Apparatus 2 (Paddle Apparatus) with a speed of 50 rpm at 37.0° C.±0.5° C. Dissolution medium (500 ml) was Helium sparged for at least 10 minutes. N=6 samples were tested. Sample time point of 5, 10, 15, 20, 30, 45, 60, and 90 minutes (final time point at 250 rpm). Filters: QLA 10 µm in-line full flow porous filter or equivalent; chromafil 1.0 µm on-line glass fiber membrane filter or equivalent.

Dissolution Procedure

The dissolution apparatus was assembled and the paddle was positioned so that the distance between its lower edge and the lower inner surface of the vessel is within 25 mm±2 mm throughout the test. This step was repeated for each of the six vessels. The speed (50 rpm) and the temperature (37.0° C.±0.5° C.) were set. 500 mL of 0.1N HCl solution were placed into each of the six vessels, previously degassed via helium purge, degassed using degasser or other suitable means. The Dissolution medium was equilibrated to set temperature and the temperature of the dissolution medium was checked with a thermometer or thermocouple before starting the dissolution. Each of the six (6) capsules were accurately weighed and the weight was recorded. The dissolution test was started. Each capsule was dropped with sinker into vessels noting the station assigned to each recorded capsule weight. The shaft was rotated at 50 rpm. Samples were withdrawn by dissolution auttosampler at 5, 10, 15, 20, 30, 45, 60, and 90 minutes into HPLC vials, or were withdraw manually. Filters (QLA 10 µm in-line full flow porous filter or equivalent; chromafil 1.0 µm on-line glass fiber membrane filter or equivalent) were utilized, discarding at least the first 5 mL of the filtrate, and clear filtrate was transfered into HPLC vials. After withdrawing samples at the 60 minute time point, the paddle rotation speed was increased to 250 rpm until the next time point of 90 minutes.

HPLC conditions: Flow rate: 1.0 ml/min; Injection Volume: 10 µL; Column Temperature: 40° C.±2° C.; Wavelengths: 240 nm; Run Time: 7 minutes; Mobile Phase A was 0.2% TFA in Water, which was prepared by mixing well 2.0 ml of trifluoroacetic acid with 1 L of water. Mobile Phase B: 0.2% TFA in Acetonitrile, which was prepared by mixing well 2.0 ml of trifluoroacetic acid to 1 L of acetonitrile; and Gradient used was as follows in Table 8.

TABLE 8

| Time (minutes) | % A (Buffer) | % B (ACN) |
|---|---|---|
| Initial | 90 | 10 |
| 4.0 | 40 | 60 |
| 4.1 | 90 | 10 |
| 7.0 | 90 | 10 |

Approximate Retention Times for sumatriptan and promethazine are 2.6 minutes and 4.8 minutes respectively.
Calculation.

If a Water® dissolution autosampler was utilized, then the Empower Dissolution Software was used to calculate the profile. Calculation are performed using a validated excel spreadsheet. When the sample was performed manually, the volume correction was considered for the calculation. The amount of promethazine HCl and sumatriptan succinate dissolved at a given time point in the drug product were calculated as follow:

Calculation for the first sampling time point:

$$R_1 = \frac{A_{spl}}{A_{std}} \times C_{std} \times 500 \text{ mL}$$

$$\% R_1 = \frac{R_1}{LC} \times 100$$

Where:
$R_1$=Amount of promethazine HCl or sumatriptan succinate released/capsule for the first sampling point, in mg
$A_{spl}$=Peak area of promethazine HCl or sumatriptan succinate in the sample solution
$A_{std}$=Average peak area of promethazine HCl or sumatriptan succinate in all standard 1 bracketing injections
$C_{std}$=Concentration of Promethazine HCl or sumatriptan succinate, adjusted for purity (μg/ml) as follow
Promethazine HCl Standard:

$$C_{std} = \frac{W_{std} \times 10 \text{ mL}}{50 \text{ mL} \times 100 \text{ mL}} \times P_{std}$$

Sumatriptan succinate Standard:

$$C_{std} = \frac{W_{std}}{100 \text{ mL}} \times P_{std}$$

$W_{std}$=Weight of promethazine HCl or sumatriptan succinate taken from standard, in mg
$P_{std}$=Purity factor of promethazine HCl or sumatriptan succinate standard
% $R_1$=% release of promethazine HCl or sumatriptan succinate for the first time point
LC=Label claim of the sample (25 mg for promethazine HCl or 126 mg for sumatriptan succinate
Calculation for subsequent sampling time points:

$$R_n = \frac{A_{spl}}{A_{std}} \times C_{std} \times (500 \text{ mL} - (n-1) \times V) + R_{n-1} \times \frac{V}{500 \text{ mL} - (n-1-1) \times V} + R_{n-2} \times \frac{V}{500 \text{ mL} - (n-2-1) \times V} + \ldots$$

$$\% R_n = \frac{R_n}{LC} \times 100$$

Where:
$R_n$=Amount of promethazine HCl or sumatriptan succinate released/capsule at the $n^{th}$ time point, in mg
$A_{spl}$=Peak area of promethazine HCl or sumatriptan succinate in the sample solution
$A_{std}$=Average peak area of promethazine HCl or sumatriptan succinate in all standard 1 bracketing injections
$C_{std}$=Concentration of Promethazine HCl or sumatriptan succinate, adjusted for purity (μg/ml) as follow
Promethazine HCl Standard:

$$C_{std} = \frac{W_{std} \times 10 \text{ mL}}{50 \text{ mL} \times 100 \text{ mL}} \times P_{std}$$

Sumatriptan succinate Standard:

$$C_{std} = \frac{W_{std}}{100 \text{ mL}} \times P_{std}$$

$W_{std}$=Weight of promethazine HCl or sumatriptan succinate taken from standard, in mg
$P_{std}$=Purity factor of promethazine HCl or sumatriptan succinate standard
n=Sampling time point (integer 1, 2, 3, . . . )
V=Sample volume withdrawn, in mL
$R_{n-1}$=Amount of promethazine HCl or sumatriptan succinate released/capsule for the $(n-1)^{th}$ time point, in mg
$R_{n-2}$=Amount of promethazine HCl or sumatriptan succinate released/capsule for the $(n-2)^{th}$ time point, in mg
% $R_n$=% release of promethazine HCl or sumatriptan succinate for the $n^{th}$ time point
LC=Label claim of the sample (25 mg for promethazine HCl or 126 mg for sumatriptan succinate
Dissolution measurements for promethazine and sumatriptan pellets measured by USP Apparatus 2 (Paddles) are shown in Table 9.

TABLE 9

| API | 5 min | 10 min | 15 min | 20 min | 30 min | 45 min | 60 min | 90 min |
|---|---|---|---|---|---|---|---|---|
| Promethazine | 95% | — | 102% | 102% | 102% | 102% | 102% | 102% |
| Sumatriptan | 81% | 89% | 92% | 94% | — | — | — | — |

Dissolution measurements for promethazine and sumatriptan (content of capsule was used without shells) measured by USP Apparatus 2 (Paddles) are shown in Table 10.

TABLE 10

| API | 5 min | 10 min | 15 min | 20 min | 30 min | 45 min | 60 min | 90 min |
|---|---|---|---|---|---|---|---|---|
| Promethazine | 85% | 90% | 92% | 94% | 94% | 95% | 96% | 100% |
| Sumatriptan | 75% | 83% | 87% | 91% | 93% | 96% | 98% | 102% |

Dissolution measurements for promethazine and sumatriptan (in a capsule) measured by USP Apparatus 2 (Paddles) are shown in Table 11. Small batch.

TABLE 11

| API | 5 min | 10 min | 15 min | 20 min | 30 min | 45 min | 60 min | 90 min |
|---|---|---|---|---|---|---|---|---|
| Promethazine | 55% | 78% | 85% | 88% | 92% | 95% | 97% | 102% |
| Sumatriptan | 74% | 89% | 94% | 96% | 98% | 100% | 101% | 104% |

Dissolution measurements for promethazine and sumatriptan (in a capsule) measured by USP Apparatus 2 (Paddle Apparatus) are shown in Table 12. Large batch.

TABLE 12

| API | Time Point | Mean | Min. | Max. | % RSD |
|---|---|---|---|---|---|
| Sumatriptan | 5 min | 66 | 56 | 73 | 9.4 |
| | 10 min | 80 | 73 | 86 | 6.6 |
| | 15 min | 85 | 81 | 89 | 4.5 |
| | 20 min | 88 | 84 | 91 | 3.8 |
| | 30 min | 90 | 87 | 93 | 2.9 |
| | 45 min | 93 | 91 | 95 | 2.1 |
| | 60 min | 94 | 92 | 96 | 1.6 |
| | 90 min | 98 | 97 | 98 | 0.3 |
| Promethazine | 5 min | 47 | 32 | 63 | 27.8 |
| | 10 min | 69 | 53 | 87 | 18.2 |
| | 15 min | 78 | 63 | 92 | 13.4 |
| | 20 min | 82 | 71 | 95 | 10.7 |
| | 30 min | 87 | 79 | 97 | 8.0 |
| | 45 min | 92 | 85 | 99 | 6.1 |
| | 60 min | 94 | 88 | 101 | 5.1 |
| | 90 min | 102 | 101 | 105 | 1.4 |

Dissolution measurements for promethazine and sumatriptan (in a capsule) measured by USP Apparatus 2 (Paddle Apparatus) are shown in Table 13. Recorded after 1 month store at 40° C.

TABLE 13

| API | Time Point | Mean | Min. | Max. | % RSD |
|---|---|---|---|---|---|
| Sumatriptan | 5 min | 60 | 47 | 77 | 21.3 |
| | 10 min | 76 | 62 | 89 | 13.7 |
| | 15 min | 81 | 69 | 91 | 10.9 |
| | 20 min | 85 | 74 | 94 | 9.6 |
| | 30 min | 88 | 80 | 95 | 7.8 |
| | 45 min | 91 | 84 | 97 | 6.4 |
| | 60 min | 93 | 86 | 98 | 5.4 |
| | 90 min | 98 | 96 | 100 | 1.1 |
| Promethazine | 5 min | 43 | 35 | 56 | 21.2 |
| | 10 min | 64 | 54 | 77 | 13.9 |
| | 15 min | 73 | 63 | 83 | 10.1 |
| | 20 min | 79 | 68 | 88 | 9.4 |
| | 30 min | 84 | 74 | 92 | 8.4 |
| | 45 min | 89 | 80 | 96 | 7.2 |
| | 60 min | 92 | 84 | 98 | 6.1 |
| | 90 min | 102 | 99 | 103 | 1.5 |

Example 7. Impurity Profile (Related Substances)

The percentages of related substances were measured using an HPLC.

Stock promethazine HCl selectivity solution was prepared by accurately weighing about 2 mg of EP promethazine for peak identification CRS and transferring into 1 mL of diluent (prepared by mixing 750 mL of mobile phase A and 250 mL of acetonitrile), followed by vortexing to dissolve. Stock sumatriptan succinate selectivity solution is prepared by by accurately weighing about 2 mg of USP sumatriptan succinate relayed impurities RS and transferring into a 1 mL of diluent (prepared by mixing 750 mL of mobile phase A and 250 mL of acetonitrile), followed by vortexing to dissolve.

Sample Preparation

Ten capsules were randomly selected and weighed. The contents of the ten capsules were emptied into a 500 mL volumetric flask. 300 mL of diluent was added and the mixture was sonicated in an ice bath for 40 minutes or until completely disintegrated with intermittent swirling. The temperature was equilibrated to room temperature and more diluent was added to volume.

Promethazine HCl impurity sample solution: stock solution sample was filtered through a 0.45 µm PVDF membrane, syringe filter or a 0.45 µm PTFE w/GMF membrane, syringe filter discarding the first 5 mL and collecting approximately 20 mL into an appropriate glass container. Fill an HPLC vial with the filtrate Sumatriptan succinate impurity sample solution: 10 mL of filtrate was pipetted into a 100 mL volumetric flask and diluent was added to volume.

The retention time (RT) of sumatriptan in the sumatriptan succinate selectivity solution is between 5.4 and 6.6 minutes. The RT of the promethazine in the promethazine HCl selectivity solution is between 44.1 and 53.9. The relative retention times (RRT) of identified sumatriptan related impurities and identified promethazine related impurities are outlined in Table 14.

TABLE 14

| | Peak Name | Approximate RT (min) | Approximate RRT |
|---|---|---|---|
| Sumatriptan impurities | Sumatriptan didesmethyl (Imp E) | 4.8 | 0.80 |
| | Sumatriptan Rel. Comp. C | 5.5 | 0.91 |
| | Sumatriptan N-Oxide (Imp D) | 8.2 | 1.36 |
| | Sumatriptan Rel. Comp. A | 19.5 | 3.24 |
| | Sumatriptan | 6.0 | 1.00 |
| Promethazine impurities | Promethazine sulfoxide | 21.4 | 0.44 |
| | N-Desmethyl promethazine | 46.1 | 0.94 |
| | Isopromethazine | 50.8 | 1.04 |
| | Phenothiazine | 61.5 | 1.26 |
| | Promethazine | 49.0 | 1.00 |

HPLC conditions: Flow rate: 2.0 ml/min; Injection Volume: 15 µL; Column Temperature: 30° C.±2° C.; Wavelengths: 228 nm for sumatriptan succinate related compounds and 252 nm for promethazine HCl related compounds; Run Time: 73 minutes; Mobile Phase A was 0.2% TFA in Water, which was prepared by mixing well 2.0 ml of trifluoroacetic acid with 1 L of water. Mobile Phase B: 0.2% TFA in Acetonitrile, which was prepared by mixing well 2.0 ml of trifluoroacetic acid to 1 L of acetonitrile; and Gradient used was as follows in Table 15.

TABLE 15

| Time (minutes) | % A (Buffer) | % B (ACN) |
|---|---|---|
| Initial | 90 | 10 |
| 7.0 | 86 | 14 |
| 51.0 | 72 | 28 |
| 69.0 | 20 | 80 |
| 70.0 | 90 | 10 |
| 73.0 | 90 | 10 |

Approximate Retention Times for sumatriptan and promethazine are 6 minutes and 49 minutes respectively.

Calculation.

All known and unknown impurities were calculated via percent area as follow:

$$\% \text{ Area} = \frac{R_u}{R_t \times RRF} \times 100\%$$

Where:
$R_u$=Peak area of related substance in the sample solution
$R_t$=Sum of peak area of promethazine or sumatriptan and all related substances areas corresponding to respective peak in sample solution
RRF=Relative Response Factor for related substances Impurity profile for promethazine and sumatriptan (in a capsule) is shown in Table 16.

TABLE 16

| Related Substances | Impurity percentages |
|---|---|
| All sumatriptan related substances combined | 0.1% |
| All promethazine related substances combined | 0.3% |

Example 8. Stability Study

The formulation was examined for its stability after one month at 40° C. Calculations Assay—Percent Label Claim:

$$\% \, LC = \frac{A_{sample}}{A_{STD}} \times C_{STD} \times \frac{D}{LC \times N_C} \times 100$$

Where:
$A_{sample}$=Peak area of Promethazine or Sumatriptan in sample preparation
$A_{STD}$=Average peak area of Promethazine or Sumatriptan in all Standard A injections
$C_{STD}$=Concentration of Promethazine hydrochloride and Sumatriptan Standard A (µg/ml), including purity and conversion to free base (Sumatriptan only)
$N_C$=Number of capsules used
LC=Label Claim: 90 mg (Sumatriptan) or 25 mg (Promethazine Hydrochloride)
D=Dilution Factor
100=Conversion to percentage
% Area for Related Substances:

$$\% \text{ Area} = \frac{A_{RI}}{A_{Main} + A_{Sum\,RS}} \times 100 =$$

Where:
$A_{RS}$: Peak area of Related Substance in the sample preparation
$A_{Main}$: Peak area of Promethazine or Sumatriptan in sample preparation
$A_{Sum\,RI}$: Sum of all related Substances area ≥LOQ in sample preparation
100: Conversion to percentage Impurity profile for promethazine and sumatriptan (in a capsule) stored at 40° C. for 1 month is shown in Table 17.

TABLE 17

| Related Substances | Impurity percentages |
|---|---|
| All sumatriptan related substances combined | None Detected |
| All promethazine related substances combined | 0.2% |

Example 9. Clinical Study for Formulation

A clinical study will be conducted in order to assess the pharmacokinetics of the sumatriptan/promethazine Formulation. In order to obtain controlled results, the study will compare data from subjects treated with the sumatriptan/promethazine Formulation to data obtained from subjects treated with comparator products. Over the course of treatment, observations aside from pharmacokinetic analysis are to be considered. Categories for additional findings to be considered include, without limitation, safety, patient predisposition correlations (genetic or otherwise), and efficacy findings. The study will be for a single-dose, open-label, randomized, three-period, three-treatment crossover study in which healthy adult subjects receive a single dose of the sumatriptan/promethazine Formulation (90 mg sumatriptan succinate/50 mg promethazine HCl capsule) in one period, a separate single dose of IMITREX® (sumatriptan succinate) tablet 100 mg in one period, and a separate single dose of promethazine HCl tablet 50 mg in one period, under fasted conditions. More specifically, subjects will receive each of the treatments listed below in randomized fashion during the three treatment periods:

Treatment A: Test Formulation
    sumatriptan succinate/promethazine HCl
    90 mg/50 mg capsule
    Dose=1×90 mg/50 mg capsule
Treatment B: Comparator Product
    IMITREX® (sumatriptan succinate) tablet, 100 mg
    Dose=1×100 mg tablet
    GlaxoSmithKline
Treatment C: Comparator Product
    Promethazine HCl tablet, 50 mg
    Dose=1×50 mg tablet
    Zydus Pharmaceuticals
Treatment C may alternatively be administered in a single dose of multiple tablets, totaling 50 mg, e.g., 4×12.5 mg or 2×25 mg.

Each drug administration will be separated by a washout period of at least 7 days. Each dose will be orally administered along with approximately 240 ml (8 fl. oz.) of room temperature water following a 10-hour overnight fast. After dosing, no food will be allowed until 4 hours postdose. Except for the 240 ml of room temperature water provided with the dose, no water consumption will be allowed for 1 hour prior through 1 hour after dose. Meals will be the same and scheduled at approximately the same times relative to dose for each study period.

During each study period, 4 ml blood samples will be obtained prior to each dosing and following each dose at selected times through 48 hours postdose. Plasma pharmacokinetic samples will be analyzed for sumatriptan and promethazine using validated analytical methods. Appropriate pharmacokinetic parameters will be calculated for each formulation using non-compartmental methods. In addition, blood and urine will be collected for clinical laboratory testing at screening and at the end of the study.

Each subject dosed in this study will receive an assigned treatment sequence based on a randomization schedule prepared by the clinical site. Subjects will be randomized to receive either Treatment A, Treatment B, or Treatment C during the first study period. After a minimum washout of 7 days, each subject will cross over to receive an alternate treatment. After another minimum washout of 7 days, subjects will cross over to receive the final treatment. At the completion of the study, each subject will have received a single dose of Treatment A, a single dose of Treatment B, and a single dose of Treatment C.

Pharmakokinetic Analysis:

Plasma samples will be analyzed for sumatriptan and promethazine using validated assays. The samples from all evaluable subjects completing at least one study period will be analyzed. Pharmacokinetic parameters for sumatriptan and promethazine will be calculated using non-compartmental analysis with 10% adjustment for the 10 mg difference in the doses of sumatriptan. The following pharmacokinetic parameters will be determined.

Concentration-time data that are below the limit of quantification (BLQ) will be treated as zero in the data summarization and descriptive statistics. In the pharmacokinetic analysis, BLQ concentrations will be treated as zero from time-zero up to the time at which the first quantifiable concentration was observed; embedded and/or terminal BLQ concentrations will be treated as "missing." Actual sample times will be used in the calculation of pharmacokinetic parameters. The following pharmacokinetic parameters will be determined:

The maximum plasma concentration ($C_{max}$) and time to $C_{max}$ ($T_{max}$) will be taken directly from the data. The elimination rate constant, $\lambda z$, will be calculated as the negative of the slope of the terminal log-linear segment of the plasma concentration-time curve; the range of data to be used will be determined by visual inspection of a semilogarithmic plot of concentration vs. time. Elimination half-life ($T_{1/2}$) will be calculated according to the following equation: $T\frac{1}{2}=0.693/\lambda_z$.

Area under the curve to the final sample with a concentration greater than the limit of quantitation (LOQ), ($AUC_{last}$), will be calculated using the linear trapezoidal method and extrapolated to infinity using: $AUC_{inf}=AUC_{last}+C_{last}/\lambda_Z$ where $C_{last}$ is the final concentration $\geq$ LOQ. In addition, the following partial AUCs will be calculated for promethazine and sumatriptan: $AUC_{(0-0.25)}$, $AUC_{(0-0.5)}$, $AUC_{(0-0.75)}$, $AUC_{(0-1.0)}$, $AUC_{(0-1.5)}$, $AUC_{(0-2.0)}$, $AUC_{(0-3.0)}$, and $AUC_{(0-4.0)}$. In this crossover study, if a quantifiable pre-dose concentration is observed, the subject's data will be reviewed to assess the magnitude of the pre-dose concentration and potential impact on the pharmacokinetic parameters. If the pre-dose concentration is greater than 5% of the respective $C_{max}$ (in the study period in which the pre-dose concentration is observed), the concentration for the subject for the specific analyte will be excluded from the pharmacokinetic analysis, although the subject's data will be retained in the concentration-time listing of the report. If the pre-dose concentration is less than 5% of the respective $C_{max}$, the subject's data will be used in the pharmacokinetic analysis without adjustment; however, an analysis will also be provided excluding the specific analyte. Any exclusion based on pre-dose concentrations will be documented in the pharmacokinetic report.

If a subject experiences emesis during the study, the subject's data will be reviewed to assess the potential impact of the emesis episode on the pharmacokinetic parameters. The subject's data will not be considered evaluable for pharmacokinetic analysis if emesis occurs within 2 times the median $T_{max}$, for a given analyte and treatment. In this case, the concentration for the subject for the specific analyte will be excluded from the pharmacokinetic analysis, although the subject's data will be retained in the concentration-time listing of the report. If emesis occurs after 2 times the median Tmax, the subject's data will be used in the pharmacokinetic analysis. Any exclusion based on episodes of emesis will be documented in the pharmacokinetic report.

Concentration-time data and pharmacokinetic parameters will be summarized by treatment and analyte using descriptive statistics (n, mean, SD, CV %, minimum, median, and maximum). All evaluable subjects completing at least one study period will be included in the pharmacokinetic analysis. Pharmacokinetic calculations will be performed using appropriate software, e.g. Phoenix™ WinNonlin® (Version 6.3 or higher, Pharsight Corporation) and/or SAS® (Version 9.3 or higher, SAS Institute Inc.).

Statistical Analysis:

Comparison of the log-transformed pharmacokinetic parameters $C_{max}$, $AUC_{last}$, and $AUC_{inf}$ for sumatriptan and promethazine across treatments will be performed using an analysis of variance (ANOVA) model and the two one-sided t-tests procedure. Partial AUCs [$AUC_{(0-0.25)}$, $AUC_{(0-0.5)}$, $AUC_{(0-0.75)}$, $AUC_{(0-1.0)}$, $AUC_{(0-1.5)}$, $AUC_{(0-2.0)}$, $AUC_{(0-3.0)}$, and $AUC_{(0-4.0)}$] for sumatriptan and promethazine will be included in the analysis for comparisons of early systemic exposure across treatments. The ANOVA model will include factors for sequence, subject within sequence, treatment, and period. The ratios of the geometric means (test to reference) and 90% confidence intervals will be reported.

The $T_{max}$ values for sumatriptan and promethazine will be compared across treatments using the Wilcoxon signed rank test. The median and range of $T_{max}$ values for each treatment will be reported with a p-value for assessing potential differences between treatments for a given analyte. A significant difference will be defined a priori as p<0.05.

Two alternative analyses of $T_{max}$ for promethazine are also planned. To utilize the intrasubject sensitivity of the study's crossover design, the time to maximum concentration of promethazine will be compared within individual subjects using paired t-tests to determine the number and percentage of subjects for whom the $T_{max}$ (Test)<$T_{max}$ (Comparator), and a p-value will be provided. Non-transformed promethazine $T_{max}$ will also be compared across treatments using an ANOVA model with factors for sequence, subject within sequence, and treatment period; the ratios of the LS means (test to reference), 90% confidence intervals and p-value will be reported.

Statistical analyses will be performed using appropriate software, e.g. Phoenix™ WinNonlin® (Version 6.3 or higher, Pharsight Corporation) and/or SAS® (Version 9.3 or higher, SAS Institute Inc.).

While particular embodiments described herein have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition that comprises:
   a plurality of first particulates, wherein each first particulate comprises:

(i) about 100 mg to about 140 mg of sumatriptan succinate; and
(ii) about 50 mg to about 150 mg of microcrystalline cellulose; and
a plurality of second particulates, wherein each second particulate comprises:
(i) about 15 mg to about 35 mg of promethazine hydrochloride;
(ii) about 30 mg to about 150 mg of a sugar sphere;
(iii) about 2.5 mg to about 15 mg of hydroxypropyl methylcellulose (HPMC);
(iv) about 0.5 mg to about 10 mg of talc;
(v) about 0.5 mg to about 10 mg of low-substituted hydroxypropyl cellulose (L-HPC); and
(vi) about 5 mg to about 30 mg of a coating.

2. The pharmaceutical composition of claim 1, that comprises:
the plurality of first particulates, wherein each first particulate comprises:
(i) about 100 mg to about 140 mg of sumatriptan succinate; and
(ii) about 50 mg to about 150 mg of microcrystalline cellulose; and
the plurality of second particulates, wherein each second particulate comprises:
(i) about: 18, 18.5, 19, or 19.5 mg of promethazine hydrochloride;
(ii) about 30 mg to about 150 mg of a sugar sphere;
(iii) about 2.5 mg to about 15 mg of hydroxypropyl methylcellulose (HPMC);
(iv) about 0.5 mg to about 10 mg of talc;
(v) about 0.5 mg to about 10 mg of low-substituted hydroxypropyl cellulose (L-HPC); and
(vi) about 5 mg to about 30 mg of a coating.

3. A pharmaceutical composition that comprises:
a plurality of first particulates, wherein each first particulate comprises:
(i) about 100 mg to about 140 mg of sumatriptan succinate; and
(ii) about 50 mg to about 150 mg of microcrystalline cellulose; and
a plurality of second particulates, wherein each second particulate comprises:
(i) about 35 mg to about 55 mg of promethazine hydrochloride;
(ii) about 30 mg to about 150 mg of a sugar sphere;
(iii) about 2.5 mg to about 15 mg of hydroxypropyl methylcellulose (HPMC);
(iv) about 0.5 mg to about 10 mg of talc;
(v) about 0.5 mg to about 10 mg of low-substituted hydroxypropyl cellulose (L-HPC); and
(vi) about 5 mg to about 30 mg of a coating.

4. The pharmaceutical composition of claim 3, that comprises:
the plurality of first particulates, wherein each first particulate comprises:
(i) about 100 mg to about 140 mg of sumatriptan succinate; and
(ii) about 50 mg to about 150 mg of microcrystalline cellulose; and
the plurality of second particulates, wherein each second particulate comprises:
(i) about: 36, 37, 38, or 39 mg of promethazine hydrochloride;
(ii) about 30 mg to about 150 mg of a sugar sphere;
(iii) about 2.5 mg to about 15 mg of hydroxypropyl methylcellulose (HPMC);
(iv) about 0.5 mg to about 10 mg of talc;
(v) about 0.5 mg to about 10 mg of low-substituted hydroxypropyl cellulose (L-HPC); and
(vi) about 5 mg to about 30 mg of a coating.

* * * * *